(12) United States Patent  
Uckun et al.

(10) Patent No.: US 7,038,049 B2  
(45) Date of Patent: May 2, 2006

(54) HALOANILINO QUINAZOLINES AND THERAPEUTIC USE THEREOF

(75) Inventors: Fatih M. Uckun, White Bear Lake, MN (US); Xing-Ping Liu, Minneapolis, MN (US); Rama Krishna Narla, St. Paul, MN (US)

(73) Assignee: Parker Hughes Institute, Roseville, MN (US)

( * ) Notice: Subject to any disclaimer, the term of this patent is extended or adjusted under 35 U.S.C. 154(b) by 4 days.

(21) Appl. No.: 10/852,076

(22) Filed: May 24, 2004

(65) Prior Publication Data

US 2005/0075353 A1    Apr. 7, 2005

Related U.S. Application Data

(63) Continuation of application No. 10/454,960, filed on Jun. 5, 2003, now abandoned, which is a continuation of application No. 09/923,903, filed on Aug. 7, 2001, now Pat. No. 6,638,939, which is a continuation of application No. 09/779,809, filed on Feb. 8, 2001, now Pat. No. 6,358,962, which is a continuation of application No. 09/357,404, filed on Jul. 20, 1999, now Pat. No. 6,258,820.

(60) Provisional application No. 60/125,177, filed on Mar. 19, 1999, provisional application No. 60/125,338, filed on Mar. 19, 1999, provisional application No. 60/125,145, filed on Mar. 19, 1999.

(51) Int. Cl.
  *C07D 239/94*  (2006.01)
  *A61K 31/517* (2006.01)
  *A61P 35/00*  (2006.01)
  *A61P 35/02*  (2006.01)

(52) U.S. Cl. .................... 544/293; 514/266.4
(58) Field of Classification Search ............. 514/266.4; 544/293
  See application file for complete search history.

(56) References Cited

U.S. PATENT DOCUMENTS

| | | |
|---|---|---|
| 4,343,940 A | 8/1982 | Kreighbaum et al. |
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,457,105 A | 10/1995 | Barker |
| 5,480,883 A | 1/1996 | Spada et al. |
| 5,710,158 A | 1/1998 | Myers et al. |
| 5,712,395 A | 1/1998 | App et al. |
| 5,721,237 A | 2/1998 | Myers et al. |
| 5,747,498 A | 5/1998 | Schnur et al. |
| 5,773,476 A | 6/1998 | Chen et al. |
| 5,792,771 A | 8/1998 | App et al. |
| 5,821,246 A | 10/1998 | Brown et al. |
| 6,004,967 A * | 12/1999 | McMahon et al. ........ 514/266.4 |
| 6,184,225 B1 | 2/2001 | Thomas et al. |
| 6,258,820 B1 | 7/2001 | Uckun et al. |
| 6,358,962 B1 | 3/2002 | Uckun et al. |

FOREIGN PATENT DOCUMENTS

| | | |
|---|---|---|
| DE | 29 36 705 A1 | 3/1980 |
| EP | 0 566 226 A1 | 10/1993 |
| WO | WO 95/15758 | 6/1995 |
| WO | WO 95/21613 | 8/1995 |
| WO | WO 96/09294 | 3/1996 |
| WO | WO 96/15118 | 5/1996 |
| WO | WO 96/40648 | 12/1996 |
| WO | WO 97/30035 | 8/1997 |
| WO | WO 97/32856 | 9/1997 |
| WO | WO 98/10767 | 3/1998 |
| WO | WO 99/61428 | 12/1999 |

OTHER PUBLICATIONS

Bridge, Alexander J.; Zhou, Hairong; Cody, Donna R.; Rewcastle, Gordon W.; McMichael, Amy; Showalter, H. D. Hollis; Fry, David W.; Kraker, Alan J.; Denny, William A., J. Med. Chem., 39(1), 267-76 (English) 1996.*

Singh, P.; Kumar, R. Journal of Enzyme Inhibition, 13(2), 125-134 (English) 1998.*

(Continued)

*Primary Examiner*—Thomas C. McKenzie
(74) *Attorney, Agent, or Firm*—Merchant & Gould PC; Denise M. Kettleberger; John L. Haack

(57) ABSTRACT

The present disclosure includes compounds, for example a compound according to formula I

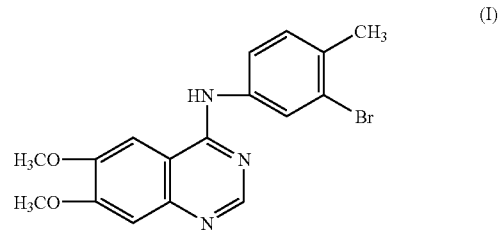

or a pharmaceutically acceptable salt thereof. The compounds of the present disclosure are useful in methods of treating cancerous conditions.

11 Claims, 18 Drawing Sheets

OTHER PUBLICATIONS

Gazit, Aviv; Chen, Jeffrey; App, Harald; McMahon, Gerald; Hirth, Peter; Chen, Irit; Levitzki, Alexander, Bioorganic & Medicinal Chemistry, 4(8), 1203-1207, 1996.*

Bridges, A. et al., "Tyrosine Kinase Inhibitors. 8. An Unusually Steep Structure-Activity Relationship for Analogues of 4-(3-Bromoanilino)-6, 7-dimethoxyquinazoline (PD 153035), a Potent Inhibitor of the Epidermal Growth Factor Receptor", *Journal of Medicinal Chemistry*, vol. 39, pp. 267-276 (Jan. 19, 1996).

Budesinsky, Z. et al., "A New Synthesis of the Quinazoline Nucleus", *Collection of Czechoslovak Chemical Communications*, vol. 37, No. 8, pp. 2779-2785 (Aug. 1972).

Fetter, J. et al., "Electron Deficient Heteroaromatic Ammonioamidates-XVI, The Synthesis and Photochemistry of Ethyl N-(2-Methyl-4-Methylene-6, 7-Methylenedioxy-3, 4-Dihydro-3-Quinazolinyl)-N-Phenylcarbamate", *Tetrahedron*, vol. 34, pp. 2557-2563 (1978).

Goodman, P. et al., "Role of Tyrosine Kinases in Induction of the c-jun Proto-oncogene in Irradiated B-lineage Lymphoid Cells", *The Journal of Biological Chemistry*, vol. 273, No. 28, pp. 17742-17748 (Jul. 10, 1998).

Hatva, E. et al., "Expression of Endothelial Cell-Specific Receptor Tyrosine Kinases and Growth Factors in Human Brain Tumors," *Amer. Journal of Pathology*, vol. 146, No. 2, pp. 368-378 (Feb. 1995).

Hennequin, L. et al., *Journal of Medicinal Chemistry*, vol. 42, No. 26, pp. 5369-5389 (1999).

Higashino, T. et al. "Reactions of the anion of quinazoline Reissert compound (3-benzoyl-3, 4-dihydro-4-quinazolinecarbon itrile) with electophiles", *Chemical & Pharmaceutical Bulletin*, vol. 33, No. 3, pp. 950-961 (Mar. 1985).

Ife, R. et al., "Reversible Inhibitors of the Gastric (H+/K+)-ATPase", *Journal of Medicinal Chemistry*, vol. 38, No. 14, pp. 2763-2773 (Jul. 7, 1995).

Kubo, K. et al., "A Novel Series of 4-Phenoxyquinolines: Potent and Highly Selective Inhibitors of PDGF Receptor Autophosphorylation", *Bioorganic & Medicinal Chemistry Letters*, vol. 7, No. 23, pp. 2935-1940 (Dec. 2, 1997).

Lempert-Sreter, M. et al., "Electron deficient heteroaromatic ammonioamidates," *Chem. Abstract*, vol. 93, entry 150203, 1 page (1980).

Malaviya, R et al., "Genetic and Biochemical Evidence for a Critical Role of Janus Kinase (JAK)-3 in Mast Cell-Mediated Type 1 Hypersensitivity Reactions", *Biochemical and Biophysical Research Communications*, vol. 257, No. 3, pp. 807-813 (Apr. 21, 1999).

Miyashita, A. et al., "Catalytic Action of Azolium Salts. II" Aroylation of 4-Chloroquinazolines with Aromatic Aldehydes Catalyzed by 1,3-Dimethylbenzimidazolium Iodide, *Chem. Pharm. Bull.* vol. 40, No. 1, pp. 43-48 (Jan. 1992).

Miyashita, A. et al., "An Approach to the Synthesis of a Papaverine Analogue Containing a Quinazoline Ring System," *Heterocycles*, vol. 40, No. 2 pp. 653-660 (1995).

Miyashita, A. et al., "Several approaches to cyanide ion-catalyzed synthesis of 4-aroyl-1-phenyl-1H-pyrazolo[3,4-d]pyrimidines," *Chem. Abstract*, vol. 128, entry 270579, 1 page (1998).

Myers, M. R. et al., "The Preparation and SAR of 4-(Anilino), 4-(Phenoxy), and 4-(Thiopenoxy)-Quinazolines: Inhibitors of p56 nd EGF-R Tyrosine Kinase Activity," *Bioorganic & Medicinal Chemistry Letters*, vol. 7, No. 4, pp. 417-420 (1997).

Narla, R. K. et al., "4-(3'-Bromo-4' hydroxylphenyl)-amino-6, 7-dimethoxyquinazoline: A Novel Quinazoline Derivative with Potent Cytotoxic Activity against Human Glioblastoma Cells," *Clinical Cancer Research*, vol. 4, pp. 1405-1414 (Jun. 1998).

Narla, R. K., et al., Inhibition of Human Glioblastoma Cell Adhesion and Invasion by 4-(4'-Hydroxylphenyl)-amino-6, 7-dimethoxyquinazoline (WHI-P131) and 4-(3'-Bromo-4'-hydroxylphenyl)-amino-6,7-dimethoxyquinazoline (WH1-P154), *Clinical Cancer Research*, vol. 4, No. 10, pp. 2463-2471 (Oct. 1998).

Nomoto, Y. et al., "Studies on Cardiotonic Agents. I. Synthesis of Some Quinazoline Derivatives," *Chem. Pharm. Bull.*, vol. 38, No. 6, pp. 1591-1595 (1990).

Porrizas, M. et al., *Endocrinology*, vol. 138, No. 4, pp. 1427-1433 (1997).

Suzuki, Y. et al., "Carbon-carbon bond cleavage of alpha -hydroxybenzylheteroarenes catalyzed," *Chem. Abstract*, vol. 128, entry 230337, 5 pages (1998).

Taylor, E. C. et al., "General procedure for the syntheisis of epoxyalkylated and acylated heterocycles," *Chem. Abstract*, vol. 93, entry 47718, 2 pages (1974).

Zagzag, D. "Angiogenic Growth Factors in Neural Embryogenesis and Neoplasia," *Amer. Journal of Pathology*, vol. 146, No. 2, pp. 293-309 (Feb. 1995).

* cited by examiner

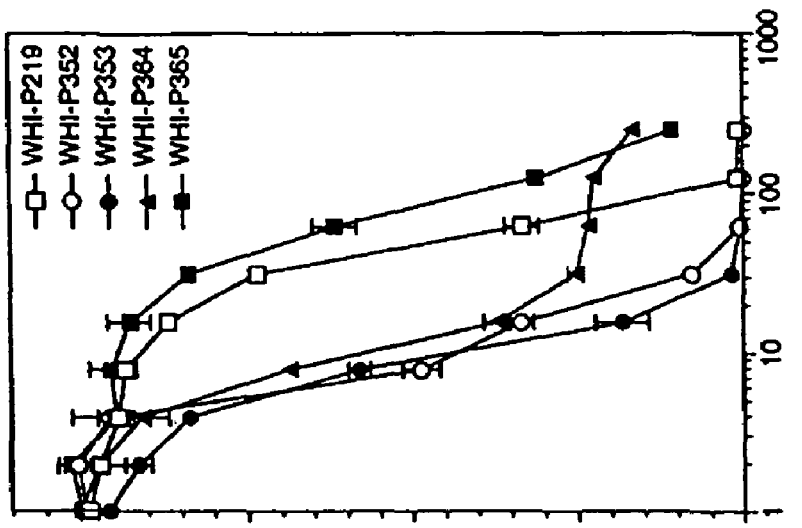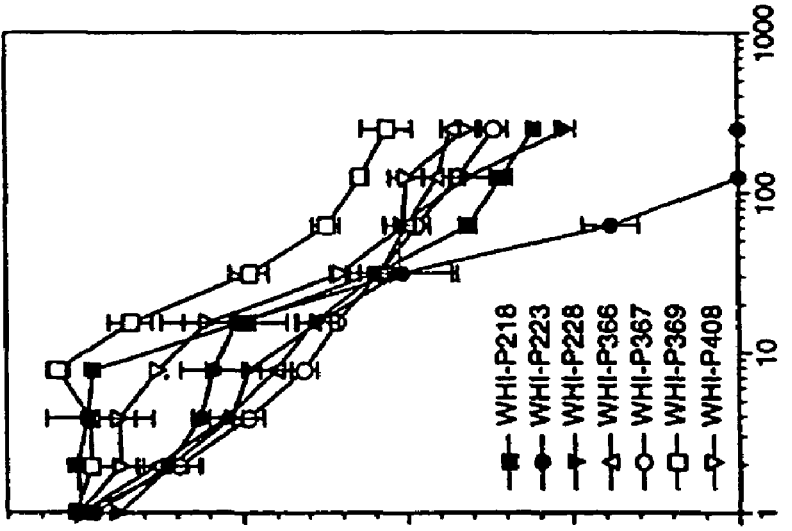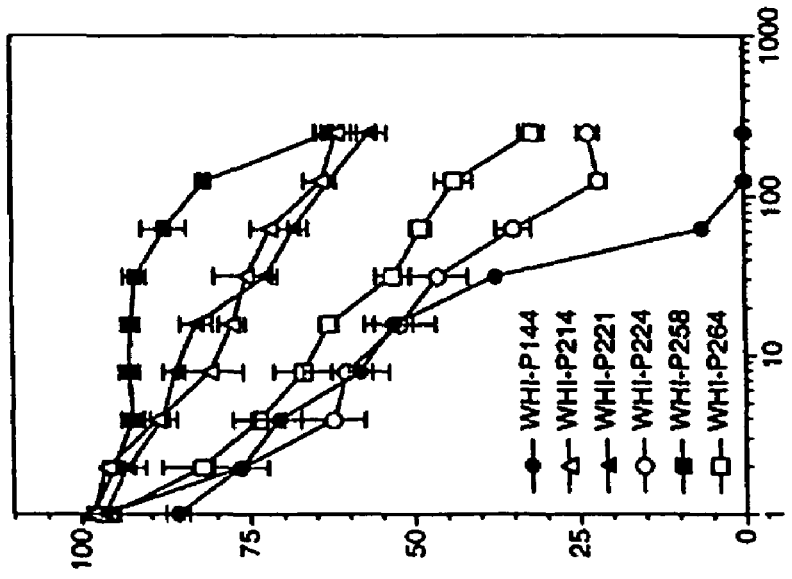

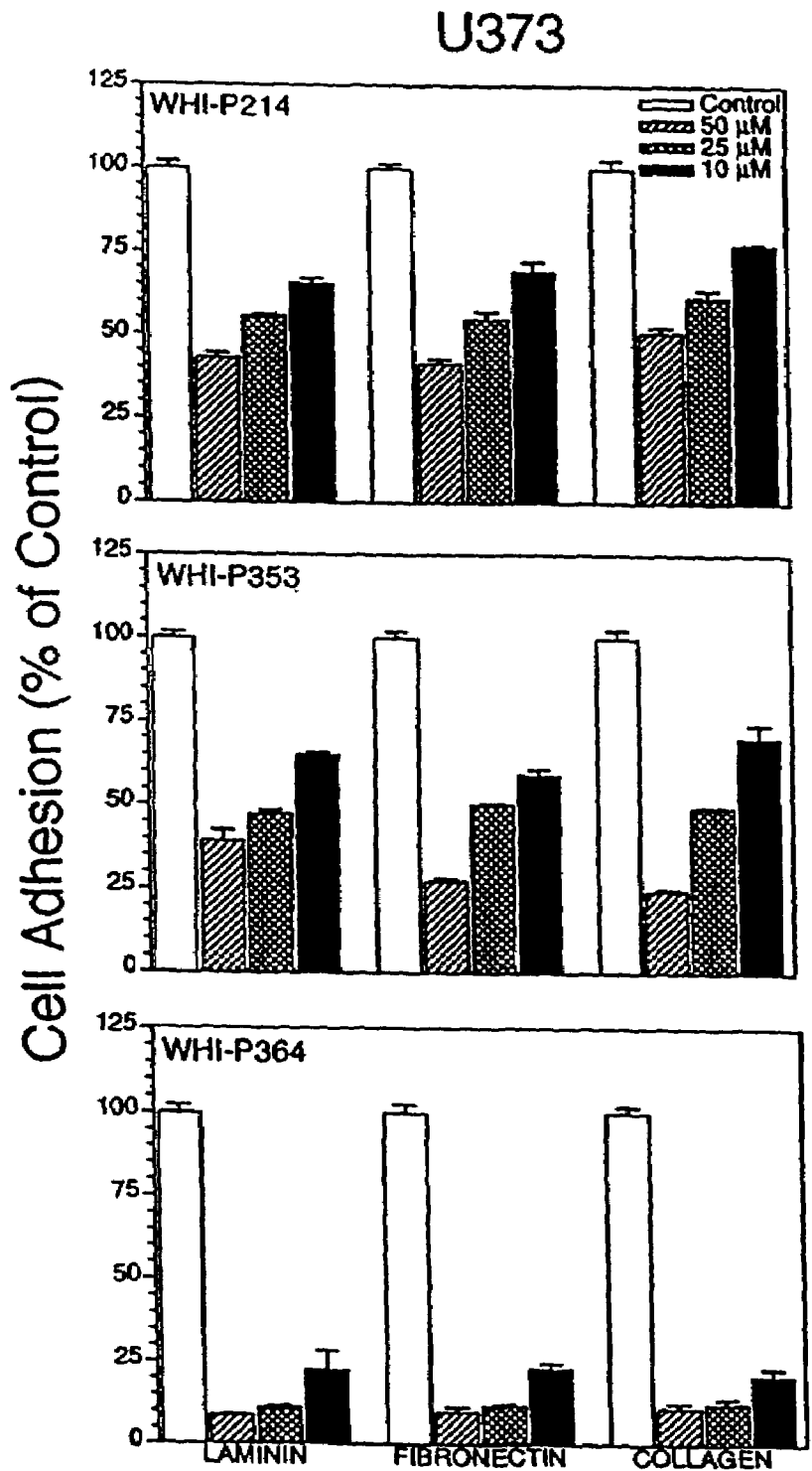
Fig.5A-C
F-dmQ inhibit adhesion

Fig. 5D-F

F-dmQ inhibit adhesion

MDA-MB-231

FIG. 6A CON
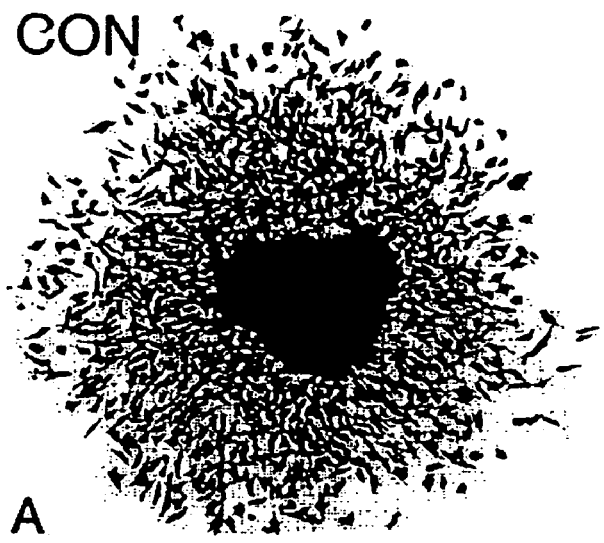
A
FIG. 6B WHI-P353:1 μM
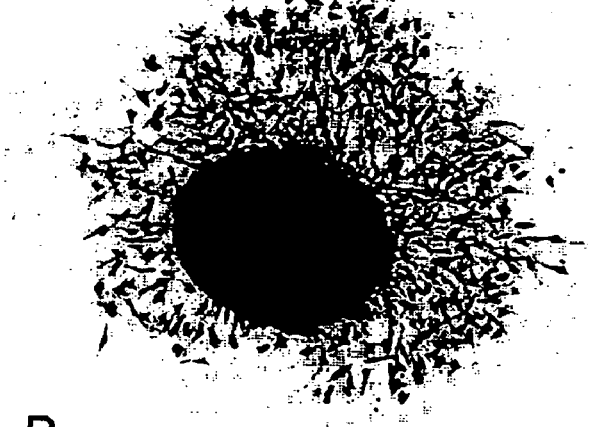
B
FIG. 6C WHI-P353:2 μM
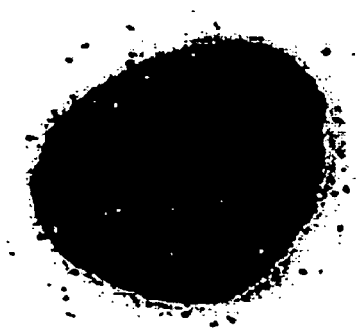
C
F-dmQ inhibits glioblastoma cell migration FIG. 6D  WHI-P364: 0.5 μM
D
FIG. 6E  WHI-P364: 1 μM
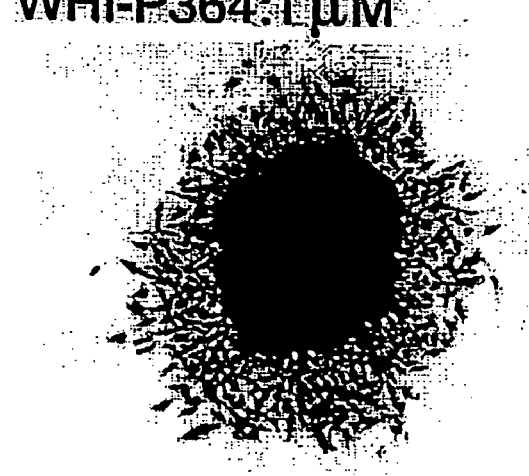
E
FIG. 6F  WHI-P364: 2 μM
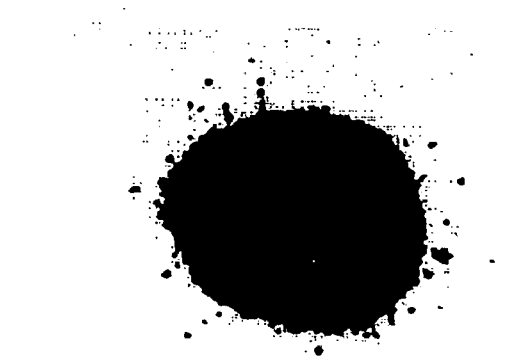
F
F - dmQ inhibits glioblastoma cell migration Cell Invasion (% of Control)

HALOANILINO QUINAZOLINES AND THERAPEUTIC USE THEREOF

CROSS-REFERENCE TO RELATED APPLICATIONS

This application is a continuation of application Ser. No. 10/454,960, filed Jun. 5, 2003, now abandoned, which is a continuation of Ser. No. 09/923,903, filed Aug. 7, 2001, now U.S. Pat. No. 6,638,939, which is a continuation of application Ser. No. 09/779,809, filed Feb. 8, 2001, now U.S. Pat. No. 6,358,962 B2, which is a continuation of application Ser. No. 09/357,404, filed Jul. 20, 1999, now U.S. Pat. No. 6,258,820 B1, which claims benefit under U.S.C. §119 of application Ser. Nos. 60/125,177, 60/125,338, 60/125,145 filed Mar. 19, 1999, which application(s) are incorporated herein by reference.

FIELD OF THE INVENTION

This application relates to quinazoline compounds, compositions and therapeutic methods for the treatment of cancers and treatment of allergic disorders by administering quinazoline compounds.

BACKGROUND OF THE INVENTION

Quinazoline compounds have been suggested as useful compounds in the treatment of cell growth and differentiation characterized by activity of the human epidermal growth factor receptor type2 (HER2). See, for example, Myers et al., U.S. Pat. No. 5,721,237. Some quinazoline derivatives have been suggested as useful as anti cancer agents for the treatment of specific receptor tyrosine kinase-expressing cancers, especially those expressing epithelial growth factor (EGF) receptor tyrosine kinase. See, for example, Barker et al., U.S. Pat. No. 5,457,105. It is generally taught that quinazolines exert their anti-tumor effects via tyrosine kinase inhibition. However, while some quinazoline compounds inhibit the growth of brain tumor cells, others with equally potent tyrosine kinase inhibitory activity fail to do so (Naria et al., 1998, *Clin. Cancer Res.* 4:1405–1414; Naria et al., 1998, *Clin. Cancer Res.* 4:2463–2471).

Several tumors expressing EGF receptors are not killed by quinazoline compounds, whereas some tumors not expressing EGF receptors are. Thus, the cytotoxic activity of quinazoline compounds cannot be attributed to the compound's tyrosine kinase inhibitory activity, and particularly not to the compound's ability to inhibit EGF receptor tyrosine kinase. A chemical structure-activity relationship determining the anti-cancer activity of quinazoline derivatives has not been established.

Novel quinazoline compounds may provide potent new therapeutic molecules for the treatment of disorders such as cancers. Methods of using both known and novel quinazoline compounds that employ an understanding of structure-function relationships are needed.

SUMMARY OF THE INVENTION

A series of quinazoline compounds were synthesized and analyzed for therapeutic activities, including anti-cancer activities, particularly against EGR receptor-negative leukemias. Specific quinazoline compounds of the invention were found to possess potent and specific tyrosine kinase inhibitory activities affecting cell proliferation and survival. Quinazoline compounds of the invention are demonstrated as useful for the treatment of specific tumors, including breast tumors, brain tumors, and leukemias, particularly EGF receptor-negative leukemias, and to be particularly useful in the treatment of multi-drug resistant leukemias.

The invention provides novel quinazoline compounds of formula I, as disclosed below, as well as therapeutic methods utilizing these compounds.

BRIEF DESCRIPTION OF THE DRAWINGS

FIGS. 1A–1C are graphs showing cytotoxic activity of fluoro-substituted dimethoxy quinazoline compounds (F-dmQ) against leukemic NALM-6 cells.

FIGS. 5A–5F are bar graphs showing the effect of F-dmQ on cancer cell-adhesion to extracelular matrix (ECM) proteins.

FIGS. 6A–6F are photographs showing the effects of HI-P353 and HI-P364 on glioblastoma cell migration from spheroids.

DETAILED DESCRIPTION OF THE INVENTION

Definitions

Figure 2A:
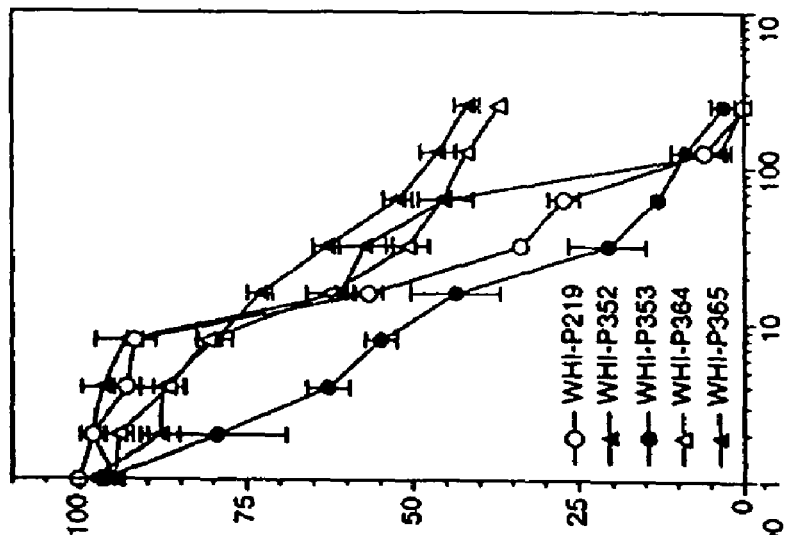
FIGS. 2A–2C are graphs showing cytotoxic activity of F-dmQ on breast cancer BT-20 cells.
Figure 2B:
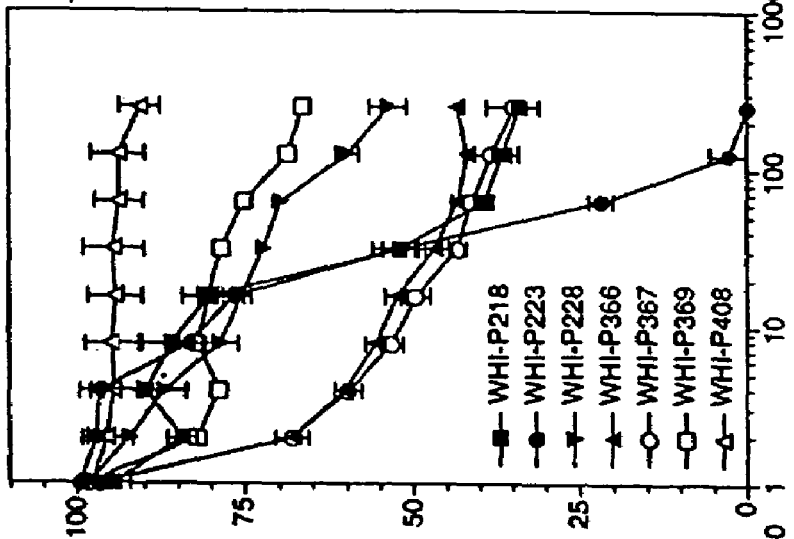
Figure 2C:
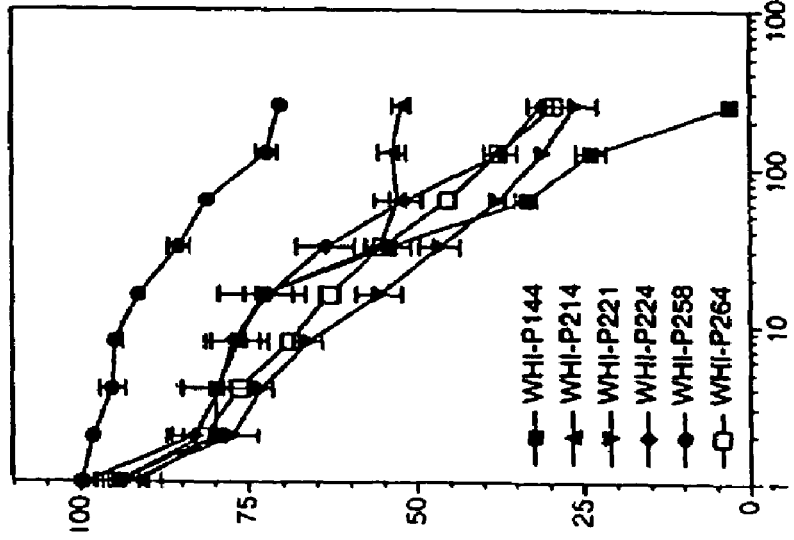

The terms "quinazoline", "quinazoline compound", and "quinazoline derivative" are used interchangeably in this application to mean compounds of formula I. All scientific and technical terms used in this application have meanings commonly used in the art unless otherwise specified. As used in this application, the following words or phrases have the meanings specified.

Halo is fluoro, chloro, bromo, or iodo. Alkyl, alkanoyl, etc., denote both straight and branched groups; but reference to an individual radical such as "propyl" embraces only the straight chain radical, a branched chain isomer such as "isopropyl" being specifically referred to. $(C_1–C_4)$alkyl includes methyl, propyl, isopropyl, butyl, iso-butyl, and sec-butyl; $(C_1–C_4)$alkoxy includes methoxy, ethoxy, propoxy, isopropoxy, butoxy, iso-butoxy, and sec-butoxy;, and (C1–C4)alkanoyl includes acetyl, propanoyl and butanoyl.

As used herein, "pharmaceutically acceptable carrier" means any material which, when combined with the compound of the invention, allows the compound to retain biological activity, such as the ability to potentiate antibacterial activity of mast cells and macrophages. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The term "conjugate" means a compound formed as a composite between two or more molecules. More specifically, in the present invention, the quinazoline derivative is bonded, for example, covalently bonded, to cell-specific targeting moieties forming a conjugate compound for efficient and specific delivery of the agent to a cell of interest.

The phrase "targeting moiety" means a molecule which serves to deliver the compound of the invention to a specific site for the desired activity. Targeting moieties include, for example, molecules that specifically bind molecules on a specific cell surface. Such targeting moieties useful in the invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

The term "prodrug moiety" is a substitution group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolyzed in vivo.

"inhibit" means to reduce by a measurable amount, or to prevent entirely.

"to treat" means to inhibit or block at least one symptom that characterizes a pathologic condition, in a mammal threatened by, or afflicted with, the condition.

Compounds of the Invention

Compounds of the invention include quinazolines having the formula:

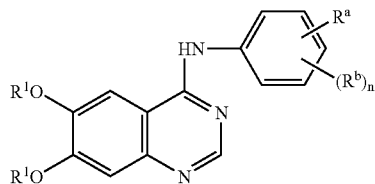

where:

$R^a$ is iodo; $(C_1-C_4)$hydroxyalkyl, methylenedioxy, ethylenedioxy, benzyloxy, $OCF_3$, $SCF_3$, $SO_3H$, $SO_2F$, $SO_2NR^2R^3$ in which $R^2$ is hydrogen or $(C_1-C_4)$alkyl and $R^3$ is hydrogen, $(C_1-C_4)$alkyl, or phenyl, $NR^2R^4$ in which $R^2$ is as defined above and $R^4$ is phenyl, or $R^a$ a group of the formula

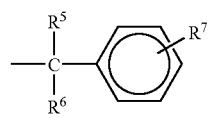

in which $R^5$ and $R^6$ are each, independently, hydrogen, $(C_1-C_4)$alkyl, or $(C_1-C_4)$perfluoroalkyl, and $R^7$ is hydrogen, halo, hydroxy, $(C_1-C_4)$alkyl, $(C_1-C_4)$alkoxy, $(C_1-C_4)$hydroxyalkyl, or $N(R^2)_2$ in which $R^2$ is as defined above;

n is an integer of 1–4;

$R^b$ is each, independently, hydrogen; halo; hydroxy, mercapto; $(C_1-C_4)$alkyl, $(C_1-C_4)$alkoxy, $(C_1-C_4)$thioalkyl, $(C_1-C_4)$hydroxyalkyl, nitro, cyano, methylenedioxy, ethylenedioxy, $COCH_3$, $CF_3$;, $OCF_3$;, $SCF_3$; COOH; $SO_3H$; $SO_2F$; phenyl or phenyl substituted by a group selected from halo, hydroxy, mercapto, $(C_1C_4)$alkyl, $(C_1-C_4)$alkoxy, $(C_1-C_4)$thioaklyl, $(C_1-C_4)$hydroxyalkyl, amino, nitro, cyano, $CF_3$, COOH, $SO_3H$, $SO_2NR^2R^3$ in which $R^2$ and $R^3$ are as defined below, and $SO_2F$. $R^a$ can also be benzyloxy or benzyloxy substituted on the phenyl portion by a group defined above, $NR^2R^3$ in which $R^2$ is H or $(C_1-C_4)$alkyl and $R^3$ is H, $(C_1-C_4)$alkyl, phenyl or phenyl substituted by a group as defined above;

$R^1$ is $(C_1-C_4)$alkyl, preferably methyl, or a pharmaceutically acceptable salt thereof, such as an acid addition salt.

Preferably, $R^a$ is a member selected from the group consisting of I, $NHC_6H_5$, $—OCH_2CH_2O—$, $—OCH_2O—$, $OCF_3$, $SCF_3$, $CH_2OH$, $C_2H_4OH$, $SO_3H$, $SO_2NH_2$, and $SO_2F$; and more preferably $R^a$ is I, $OCF_3$ or $SO_2F$. Most preferably, $R^a$ is I or $R^a$ is $OCF_3$.

In an alternative preferred compound, n is 1 and $R^a$ is a group of the formula:

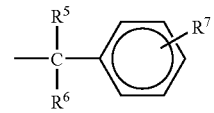

Preferably, $R^5$ and $R^6$ are each, independently, H, $CH_3$ or $CF_3$, and most preferably, $R^5$ and $R^6$ are $CF_3$ and $R^7$ is $NH_2$.

In another preferred compound, $R^b$ is at least one member selected from the group consisting of F, Cl, Br, I, OH, $NH_2$, $NO_2$, CN, COOH, $CH_3$, and $CF_3$, and more preferably $R^b$ is at least one member selected from the group consisting of F, Cl, Br, OH, and $CF_3$.

Additional preferred quinazoline compounds useful in the treatment of tumors are described more fully below and particularly in the Examples. These include:

4-(3',5'-dibromo-4'-methylphenyl)amino-6,7-dimethoxyquinazoline;

4-(2',4',6'-tribromophenyl)amino-6,7-dimethoxyquinazoline;

4-(2',3',5',6'-tetrafluoro-5'-bromophenyl)amino-6,7-dimethoxyquinazoline;

4-(4'-fluorophenyl)amino-6,7-dimethoxyquinazoline;

4-(4'-fluoromethylphenyl)amino-6,7-dimethoxyquinazoline; and 4-(3',5'-bis-fluoromethylphenyl)amino-6,7-dimethoxyquinazoline.

Methods of Treatment

The compounds of the invention are useful for the treatment of animals, including humans. In particular, the compounds of the invention have been found to be potent inhibitors of tumor cell proliferation and survival and effective to induce apoptosis of malignant cells.

Compounds of the invention have surprisingly been found to be effective for inducing apoptosis and/or cytotoxicity of leukemia cells. In particular, 4-(4'-hydroxyphenyl)amino-6, 7-dimethoxyquinazoline compounds of the invention have been found to effectively induce apoptosis in multi-drug resistant leukemia. A preferred compound for the treatment of multi-drug resistant leukemia is 4-(3'-bromo-4'-hydroxyphenyl)amino-6,7-dimethoxyquinazoline.

Compounds of the invention that are particularly useful for treating leukemia include:
4-(3',5'-dibromo-4'-methylphenyl)amino-6,7-dimethoxyquinazoline,
4-(2',4',6'-tribromophenyl)amino-6,7-dimethoxyquinazoline,
4-(2',3',5',6'-tetrafluoro-4'-bromophenyl)amino-6,7-dimethoxyquinazoline,
4-(4'-fluorophenyl)amino-6,7-dimethoxyquinazoline,
4-(3'-fluorophenyl)amino-6,7-dimethoxyquinazoline,
4-(2'-fluorophenyl)amino-6,7-dimethoxyquinazoline,
4-(4'-trifluoromethylphenyl)amino-6,7-dimethoxyquinazoline,
4-(2'-trifluoromethylphenyl)amino-6,7-dimethoxyquinazoline, and
4-(3',5'-bis-trifluoromethylphenyl)amino-6,7-dimethoxyquinazoline.

Compounds of the invention that are particularly useful for treating breast tumors include:
4-(3'-bromophenyl)amino-6,7-dimethoxyquinazoline,
4-(3',5'-dibromo-4'-hydroxyphenyl)amino-6,7-dimethoxyquinazoline,
4-(3'-chloro-4'-hydroxyphenyl)amino-6,7-dimethoxyquinazoline,
4-(3',5'-bis-trifluoromethylphenyl)amino-6,7-dimethoxyquinazoline,
4-(2',3',5',6'-tetrafluoro-4'-bromophenyl)amino-6,7-dimethoxyquinazoline,
4-(4'-fluorophenyl)amino-6,7-dimethoxyquinazoline,
4-(3'-fluorophenyl)amino-6,7-dimethoxyquinazoline, and
4-(2'-fluorophenyl)amino-6,7-dimethoxyquinazoline.

Compositions

The compounds of the invention are useful as pharmaceutical compositions prepared with a therapeutically effective amount of a compound of claim 1 and a pharmaceutically acceptable carrier or diluent.

The quinazoline compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, quinazoline compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the quinazoline compounds may be combined with one or more excipients and used in the form of ingestible tablets, buccal tablets, troches, capsules, elixirs, suspensions, syrups, wafers, and the like. The quinazoline compounds may be combined with a fine inert powdered carrier and inhaled by the subject or insufflated. Such compositions and preparations should contain at least 0.1% quinazoline compounds. The percentage of the compositions and preparations may, of course, be varied and may conveniently be between about 2 to about 60% of the weight of a given unit dosage form. The amount of quinazoline compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the quinazoline compounds may be incorporated into sustained-release preparations and devices.

The quinazoline compounds may also be administered intravenously or intraperitoneally by infusion or injection. Solutions of the quinazoline compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the quinazoline compounds which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the quinazoline compounds in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile filtered solutions.

For topical administration, the quinazoline compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water-alcohol/glycol blends, in which the quinazoline compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the quinazoline compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the quinazoline compounds in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the quinazoline compounds required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The quinazoline compounds are conveniently administered in unit dosage form; for example, containing 5 to 1000 mg, conveniently 10 to 750 mg, most conveniently, 50 to 500 mg of active ingredient per unit dosage form.

Ideally, the quinazoline compounds should be administered to achieve peak plasma concentrations of from about 0.5 to about 75 µM, preferably, about 1 to 50 µM, most preferably, about 2 to about 30 µM. This may be achieved, for example, by the intravenous injection of a 0.05 to 5% solution of the quinazoline compounds, optionally in saline, or orally administered as a bolus containing about 1–100 mg of the quinazoline compounds. Desirable blood levels may be maintained by continuous infusion to provide about 0.01–5.0 mg/kg/hr or by intermittent infusions containing about 0.4–15 mg/kg of the quinazoline compounds.

The quinazoline compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Targeting Quinazolines to Cells

In a preferred embodiment, the quinazoline compound is targeted to cells where treatment is desired, for example, to leukemia cells, to breast cells, or to other tumor cells. The compound is targeted to the desired cell by conjugation to a targeting moiety that specifically binds the desired cell, thereby directing administration of a conjugated molecule. Useful targeting moieties are ligands which specifically bind cell antigens or cell surface ligands, for example, antibodies against the B cell antigen, CD19 (such as B43) and the like.

To form the conjugates of the invention, targeting moieties are covalently bonded to sites on the quinazoline compound. The targeting moiety, which is often a polypeptide molecule, is bound to compounds of the invention at reactive sites, including $NH_2$, SH, CHO, COOH, and the like. Specific linking agents are used to join the compounds. Preferred linking agents are chosen according to the reactive site to which the targeting moiety is to be attached.

Methods for selecting an appropriate linking agent and reactive site for attachment of the targeting moiety to the compound of the invention are known, and are described, for example, in Hermanson, et al., *Bioconjugate Techniques*, Academic Press, 1996; Hermanson, et al., *Immobilized Affinity Ligand Techniques*, Academic Press, 1992; and *Pierce Catalog and Handbook*, 1996, pp. T155–T201.

Administration of Quinazolines

According to the invention, quinazoline compounds may be administered prophylactically, i.e., prior to onset the pathological condition, or the quinazoline compounds may be administered after onset of the reaction, or at both times.

EXAMPLES

The invention may be further clarified by reference to the following Examples, which serve to exemplify some of the preferred embodiments, and not to limit the invention in any way.

Example 1

Synthesis of Quinazoline Derivatives

All chemicals were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under a nitrogen atmosphere.

The key starting material, 4-chloro-6,7-dimethoxyquinazoline, was prepared according to published procedures (Nomoto, et al., 1990, *Chem. Pharm. Bull.,* 38:1591–1595; Thomas C. L., 1970, IN:*Catalyc Processes and Proven Catalysts*, Academic Press, New York, N.Y.) as outlined below in Scheme 1. Specifically, 4.5-dimethoxy-2-nitrobenzoic acid (compound 1) was treated with thionyl chloride to form acid chloride, followed by reacting with ammonia to yield 4,5-dimethoxy-2-nitrobenzamide (compound 2). Compound 2 was reduced with sodium borohydride in the presence of catalytic amounts of copper sulphate to give 4,5-dimethoxy-2-aminobenzamide (compound 3), which was directly refluxed with formic acid to yield 6,7-dimethoxyquinazoline-4(3H)-one (compound 4). Compound 4 was refluxed with phosphorus oxytrichloride to give 4-chloro-6,7-dimethoxyquinazoline (compound 5) in good yield.

Substituted quinazoline derivatives were prepared by the condensation of 4-chloro-6,7-dimethoxyquinazoline with substituted anilines as outlined below in Scheme 2:

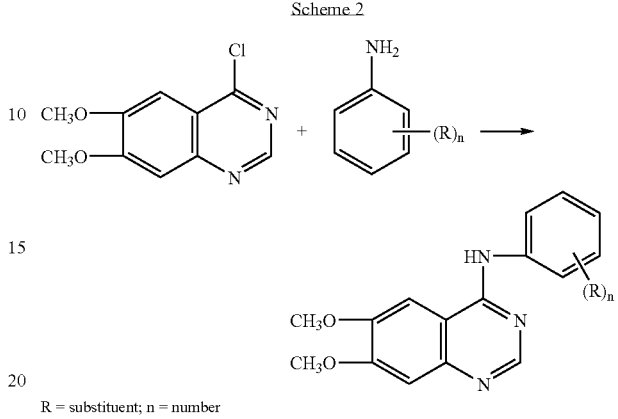

R = substituent; n = number

Specifically, a mixture of 4-chloro-6,7-dimethoxyquinazoline (448 mg, 2 mmols) and the substituted aniline (2.5 mmols) in EtOH (20 ml) was heated to reflux. After refluxing for 4–24 hours, an excess amount of $Et_3N$ was added, and the solvent was concentrated to give the crude product which was recrystalized from DMF.

As discussed above, the novel hydroxy-substituted quinazoline derivatives of the invention were created by reacting the appropriate substituted anilines with the key starting material, 4chloro-6,7-dimethoxyquinazoline.

Physical Characteristics

Melting points are uncorrected. $^1$H NMR spectra were recorded using a Varian Mercury 300 spectrometer in DMSO-$d_6$ or $CDCl_3$. Chemical shifts are reported in parts per million (ppm) with tetramethylsilane (TMS) as an internal standard at zero ppm. Coupling constants (J) are given in hertz and the abbreviations s, d, t, q, and m refer to singlet, doublet, triplet, quartet and multiplet, respectively. Intrared spectra were recorded on a Nicolet PROTEGE 460-IR spectrometer. Mass spectroscopy data were recorded on a FINNIGAN MAT 95, VG 7070E-HF G.C. system with an HP 5973 Mass Selection Detector. UV spectra were recorded on BECKMAN DU 7400 and using MeOH as the solvent. TLC was performed on a precoated silica gel plate (Silica Gel KGF; Whitman Inc). Silica gel (200–400 mesh, Whitman Inc.) was used for all column chromatography separations. All chemicals were reagent grade and were purchased from Aldrich Chemical Company (Milwaukee, Wis.) or Sigma Chemical Company (St Louis, Mo.).

Example 2

Bromine Substituted Quinazoline Compounds

Bromine substituted quinazoline derivatives were synthesized and characterized as discussed above in Example 1. The structures and physical data are shown below:

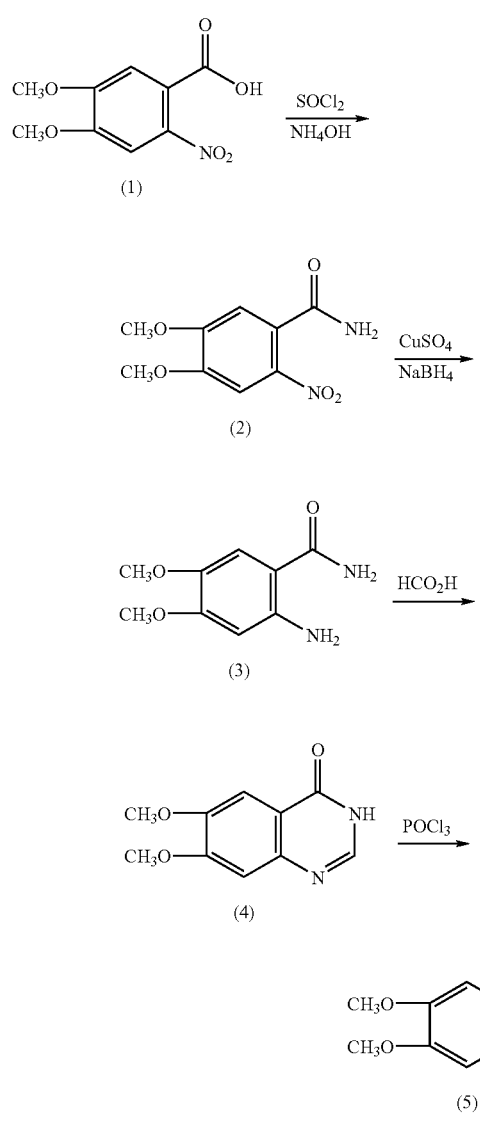

| | | Bromine Substituted Quinazoline Compounds | | |
|---|---|---|---|---|
| No | Name | Structure | Formula | MW |
| 1 | P-79 | | $C_{16}H_{14}BrN_3O_2$ | 360 |
| 2 | P-88 | | $C_{17}H_{14}BrN_3O_4$ | 404 |
| 3 | P-97 | | $C_{16}H_{13}Br_2N_3O_3$ | 455 |
| 4 | P-111 | | $C_{17}H_{16}BrN_3O_2$ | 374 |
| 5 | P-112 | | $C_{16}H_{13}Br_2N_3O_2$ | 439 |
| 6 | P-154 | | $C_{16}H_{14}BrN_3O_3$ | 376 |

-continued

Bromine Substituted Quinazoline Compounds

| No | Name | Structure | Formula | MW |
|----|------|-----------|---------|-----|
| 7 | P-160 | 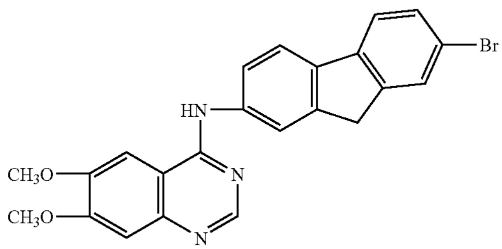 | $C_{23}H_{18}BrN_3O_2$ | 448 |
| 8 | P-164 | 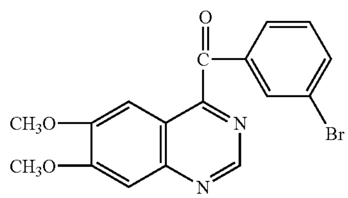 | $C_{17}H_{13}BrN_2O_3$ | 373 |
| 9 | P-190 | 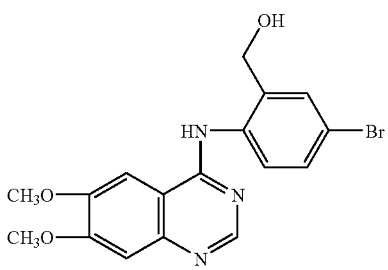 | $C_{17}H_{16}BrN_3O_3$ | 389 |
| 10 | P-210 | 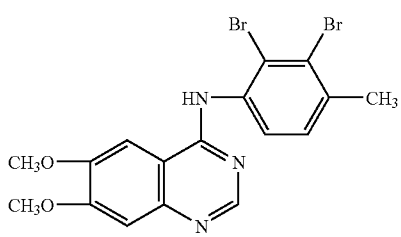 | $C_{17}H_{15}Br_2N_3O_2$ | 453 |
| 11 | P-211 | 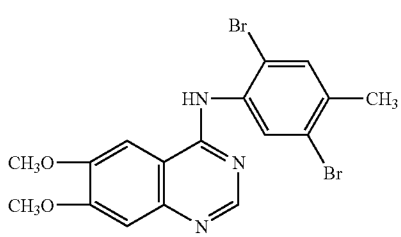 | $C_{17}H_{15}Br_2N_3O_2$ | 453 |
| 12 | P-212 | 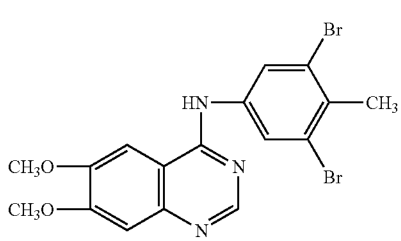 | $C_{17}H_{15}Br_2N_3O_2$ | 453 |

-continued
Bromine Substituted Quinazoline Compounds
| No | Name | Structure | Formula | MW |
|---|---|---|---|---|
| 13 | P-214 | 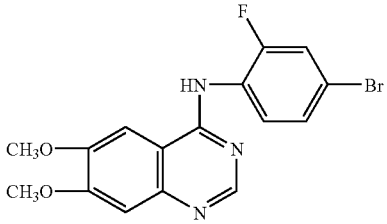 | C$_{16}$H$_{13}$BrFN$_3$O$_2$ | 378 |
| 14 | P-222 | 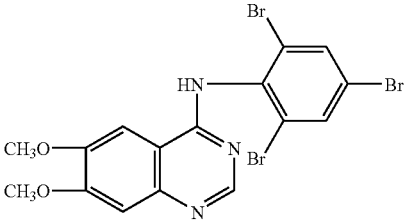 | C$_{16}$H$_{12}$Br$_3$N$_3$O$_2$ | 518 |
| 15 | P-234 | 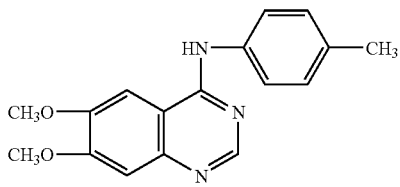 | C$_{17}$H$_{17}$N$_3$O$_2$ | 295 |
| 16 | P-241 | 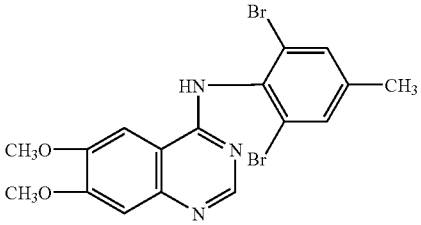 | C$_{17}$H$_{15}$Br$_2$N$_3$O$_2$ | 453 |
| 17 | P-258 | 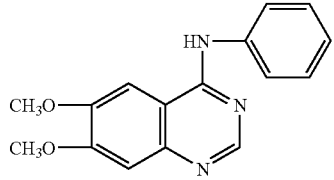 | C$_{16}$H$_{15}$N$_3$O$_2$ | 281 |
| 18 | P-260 | 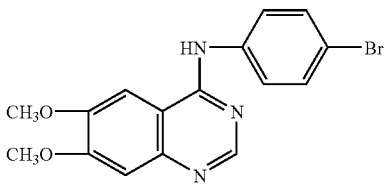 | C$_{16}$H$_{14}$BrN$_3$O$_2$ | 360 |
| 19 | P-261 | 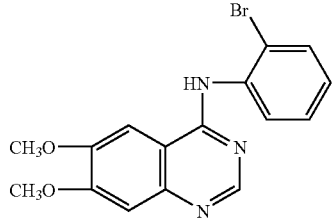 | C$_{16}$H$_{14}$BrN$_3$O$_2$ | 360 |

Bromine Substituted Quinazoline Compounds

| No | Name | Structure | Formula | MW |
|---|---|---|---|---|
| 20 | P-262 | 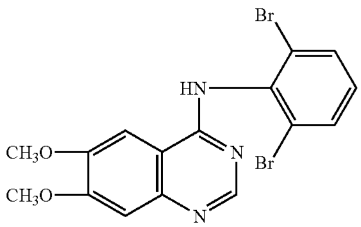 | $C_{16}H_{13}Br_2N_3O_2$ | 439 |
| 21 | P-263 | 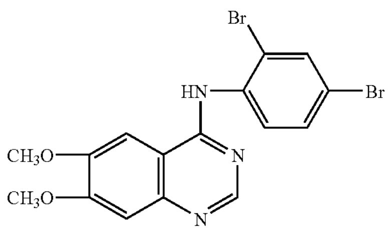 | $C_{16}H_{13}Br_2N_3O_2$ | 439 |

4-(3'-Bromophenyl)-amino-6,7-dimethoxyquinazoline(HI-P79)Yield 84.17%; m.p.246.0–249.0° C. $^1$H NMR(DMSO-$d_6$): δ 10.42(br, s, 1H, NH), 8.68(s, 1H, 2-H), 8.07–7.36(m, 5H,5,2',4',5', 6'—H), 7.24(s, 1H, 8H), 3.98(s, 3H, —OCH$_3$), 3.73(s, 3H, —OCH$_3$); IR(KBr)$\upsilon_{max}$: 3409, 2836, 1632, 1512, 1443, 1243, 1068 cm$^{-1}$; GC/MS m/z 361(M$^+$+1, 61.8), 360(M$^+$, 100.0), 359(M$^+$-1, 63.5), 344(11.3), 222(10.9), 140(13.7). Anal.($C_{16}H_{14}BrN_3O_2$ HCl) C, H, N.
4-(4'-Bromo-2'-caboxylphenyl)-amino-6,7-dimethoxyquinazoline(HI-P88)Yield 92.82%; m.p.>300.0° C. $^1$H NMR(DMSO-$d_6$ + CF$_3$CO$_2$H): δ 9.95(d, 1H), 8.74(d, 1H, Ar—H), 8.30, 8.28(2d, 2H), 7.95(d, 1H), 7.83(s, 1H), 4.21(s, 3H, —OCH$_3$), 4.15(s, 3H, —OCH$_3$); UV(MeOH): 205, 229.0 nm. IR(KBr)$\upsilon_{max}$: 3444(br), 2737, 1592, 1504, 1443, 1273, 1070 cm$^{-1}$. GC/MS m/z 388(M$^{30}$ + 1 – OH, 18.08), 387(M$^+$ – OH, 100.00), 386(M$^+$ – 1 – OH, 30.84), 385(97.52), 299(4.78). Anal.($C_{16}H_{14}BrN_3O_2$ HCl) C, H, N.
4-(3',5'-Dibromo-4'-hydroxylphenyl)-amino-6,7-dimethoxyquinazoline(HI-P97). Yield 72.80%; m.p.>300.0° C. $^1$H NMR(DMSO-$d_6$): δ 9.71(s, 1H, —NH), 9.39(s, 1H, —OH), 8.48(s, 1d, 2-H), 8.07(s, 2H, 2', 6'-H), 7.76(s, 1H, 5-H), 7.17(s, 1H, 8-H), 3.94(s, 3H, —OCH$_3$); 3.91(s, 3H, —OCH$_3$). UV(MeOH): 208.0, 210.0, 245.0, 320.0 nm. IR(KBr)$\upsilon_{max}$: 3504(br), 3419, 2868, 1627, 1512, 1425, 1250, 1155 cm$^{-1}$; GC/MS m/z 456(M$^+$ + 1, 54.40), 455(M$^+$, 100.00), 454(M$^+$ – 1, 78.01), 439(M$^+$ —OH, 7.96), 376(M$^+$ + 1-Br, 9.76), 375(M$^+$ —Br, 10.91), 360(5.23). Anal.($C_{16}H_{13}Br_2N_3O_3$) C, H, N.
4-(3'-Bromo-4'-methylphenyl)-amino-6,7-dimethoxyquinazoline (HI-P111): Yield 82.22%; m.p. 225.0–228° C. $^1$H NMR(DMSO-$d_6$): δ 10.23(s, 1H, —NH), 8.06(d, 1H, $J_{2',6'}$ = 2.1 Hz, 2'-H), 7.89(s, 1H, 5-H), 7.71(dd, 1H, $J_{5',6'}$ = 8.7 Hz, $J_{2',6'}$ = 2.1 Hz, 6'-H), 7.37(d, 1H, $J_{5',6'}$ = 8.7 Hz, 5'-H), 7.21 (s, 1H, 8-H), 3.96(s, 3H, —OCH$_3$), 3.93(s, 3H, —OCH$_3$). UV(MeOH): 204.0, 228.0, 255.0, 320.0 nm. IR(KBr)$\upsilon_{max}$: 3431, 3248, 2835, 1633, 1517, 1441, 1281, 1155 cm$^{-1}$. GC/MS m/z 375(M$^+$ + 1, 76.76), 374(M$^+$, 100.00), 373(M$^+$ –1, 76.91), 358(M$^+$ + 1-OH, 11.15), 357(1.42), 356(6.31). Anal. ($C_{17}H_{16}BrN_3O_2$.HCl) C, H, N.
4-(2',5'-Dibromophenyl)-amino-6,7-dimethoxyquinazoline (HI-P112): Yield 70.05%; m.p. >300.0° C. $^1$H NMR(DMSO-$d_6$): δ 11.51(s, 1H, —NH), 8.76(s, 1H, 2-H), 8.21(s, 1H, 5-H), 7.81(d, 1H, $J_{4',6'}$ = 2.4 Hz, 6'-H), 7.75(d, 1H, $J_{3',4'}$ = 8.7 Hz, 3'-H), 7.55(dd, 1H, $J_{4',6'}$ = 2.4 Hz, $J_{3',4'}$ = 8.7 Hz, 4'-H), 7.33 (s, 1H, 8-H), 3.98(s, 3H, —OCH$_3$), 3.97(s, 3H, —OCH$_3$). UV(MeOH): 208.0, 238.0, 330.0 nm. IR(KBr)$\upsilon_{max}$: 3444, 2836, 1628, 1510, 1431, 1277, 1070 cm$^{-1}$. GC/MS m/z 440(M$^+$+1, 10.12), 439(M$^+$, 7.0), 438 (M$^+$ –1, 3.63), 360(M$^+$ + 1-Br, 99.42), 359(M$^+$ -Br, 20.45), 358(M$^+$ –1-Br, 100.00), 343(20.80), 299 (8.62). Anal. ($C_{16}H_{13}Br_2N_3O_2$.HCl) C, H, N.
4-[(3'-Bromo-9'-fluorenone)-2'-]amino-6,7-dimethoxyquinazoline (HI-P119): Yield 75.23%; m.p. 255.0–257.0° C. $^1$H NMR(DMSO-$d_6$): δ 8.77(s, 1H, —NH), 8.33(s, 1H, 2-H), 7.89(s, 1H, 5-H), 7.40(s, 1H, 8-H), 7.74–7.26(m, 6H, Ar—H), 4.12(s, 3H, —OCH$_3$), 4.11(s, 3H, OCH$_3$). UV(MeOH): 205, 229.0, 251.0, 320.0 nm. IR(KBr)$\upsilon_{max}$: 3444, 2836, 1628, 1510, 1477, 1070 cm$^{-1}$. GC/MS m/z 464(M$^+$ +2, 40.81), 463(M$^+$+1, 7.56), 462(M$^+$, 27.26), 384(M$^+$ +2-Br, 69.56), 383(M$^+$ +1-Br, 35.50), 382(M$^+$ —Br, 100.00), 352(10.85), 206(26.73), 191(11.31). Anal. ($C_{23}H_{16}BrN_3O_3$ HCl) C, H, N.
4-(2',3',5',6'-Tetrafluoro-4'-bromolphenyl)-amino-6,7-dime-thoxyquinazoline (HI-P144): Yield 78.24%; m.p. 180.0–182.0° C. $^1$H NMR(DMSO-$d_6$): δ 7.78(s, 1H, 2-H), 7.53(s, 1H, 5-H), 6.79(s, 1H, 8-H), 3.81 (s, 3H, —OCH$_3$), 3.3.79(s, 3H, —OCH$_3$), Anal. ($C_{16}H_{10}BrF_4N_3O_2$.HCl) C, H, N.
4-(3'-Bromo-4'-hydroxylphenyl)-amino-6,7-dimethoxyquinazoline(HI-P154): Yield 89.90%; m.p. 233.0–233.5° C. $^1$H NMR(DMSO-$d_6$): δ 10.08(s, 1H, —NH), 9.38(s, 1H, —OH), 8.40(s, 1H, 2-H), 7.89 (d, 1H, $J_{2',6'}$ = 2.7 Hz, 2'-H), 7.75(s, 1H, 5-H), 7.55(dd, 1H, $J_{5',6'}$ = 9.0 Hz, $J_{2',6'}$ = 2.7 Hz, 6'-H), 7.14(s, 1H, 8-H), 6.97(d, 1H, $J_{5',6'}$ = 9.0 Hz, 5'-H), 3.92(s, 3H, —OCH$_3$), 3.90(s, 3H, —OCH$_3$). UV(MeOH): 203.0, 222.0, 250.0, 335.0 nm. IR(KBr)$\upsilon_{max}$: 3431(br), 2841, 1624, 1498, 1423, 1244 cm$^{-1}$. GC/MS m/z 378(M$^+$+2, 90.68), 377(M$^+$+1, 37.49), 376(M$^+$, 100.00), 360(M$^+$, 3.63), 298(18.86), 282(6.65). Anal.($C_{16}H_{14}BrN_3O_3$.HCl) C, H, N.
4-[(7'-Bromofluorene)-2']-amino-6,7-dimethoxyquinazoline (HI-P160): Yield 73.21%; m.p. 254.0–256.0° C. $^1$H NMR(DMSO-$d_6$): δ 9.69(br, s, 1H, —NH), 8.52(s, 1H, 2-H), 8.12–7.20(m, 9H, 5, 8, 1', 3', 4', 5', 6', 8', 9'-H), 3.99(s, 3H, —OCH$_3$), 3.94(s, 3H, —OCH$_3$). UV(MeOH): 208.0, 223.0, 348.0 nm. IR(KBr) $\upsilon_{max}$: 3421, 2820, 1624, 1516, 1431, 1294, 1223 cm$^{+1}$. GC/MS m/z 450(M$^+$+2, 100), 449(M$^+$+1, 35), 448(M$^+$, 95), 311(25). Anal.($C_{23}H_{18}BrN_3O_2$.HCl) C, H, N.

Bromine Substituted Quinazoline Compounds

| No | Name | Structure | Formula | MW |
|---|---|---|---|---|

4-(3'-Bromobenzoyl)-6,7-dimethoxyquinazoline (HI-P164): Yield 81.20%, m.p.258.0–263.0° C. $^1$H NMR (DMSO-d$_6$): δ 9.25(s, 1H, 2-H), 8.14(s, 1H, 5-H), 7.92–7.43(m, 4H , 2', 4', 5', 6'-H), 7.40(s, 1H, 8-H), 4.11(s, 3H, -OCH$_3$), 4.00(s, 3H, —OCH$_3$). UV(MeOH): 203.0, 220.0, 238.0 nm. IR(KBr) $υ_{max}$: 3432, 1664, 1504, 1431, 1230 cm$^{-1}$. GC/MS m/z 374(M$^+$+1, 48.96), 373(M$^+$, 34.93), 372(M$^+$−1, 47.67), 357 (58.74), 343(100.00), 293(M$^+$—Br, 31.48), 189(26.27). Anal. (C$_{17}$H$_{13}$BrN$_2$O$_3$) C, H, Br, N.

4-(4'-Bromo-6'-hydroxymethylphenyl)-amino-6,7-dimethoxyquinazoline (HI-P190): Yield 73.08%; m.p. 222.0–223.0° C., $^1$H NMR(DMSO-d$_6$): δ 11.30(s, 1H, —OH), 8.22(s, 1H, —NH), 7.77–7.23(m, 5H, 5, 8, 2', 3', 5'-H), 4.49(s, 2H, PhCH$_2$—H), 4.01(s, 3H, —OCH$_3$), 3.90(s, 3H, —OCH$_3$). UV(MeOH): 207.0, 250.0, 332.0 nm. IR(KBr)$υ_{max}$: 3446, 2829, 2752, 1652, 1371, 1365, 1280 cm$^{-1}$. GC/MS m/z 391(M$^+$+1, 29.33), 389(M$^+$, 29.82), 360(M$^+$—CH$_2$OH, 50.76), 358(52.39), 311(18.33), 280(43.20), 206(62.80), 191(100.00). Anal.(C$_{17}$H$_{16}$BrN$_3$O$_3$.HCl) C, H, N.

4-(2',3'-Dibromo-4'-methylphenyl)-amino-6,7-dimethoxyquinazoline (HI-P210): Yield 81.24%, mp 233.0–236.0° C., $^1$H NMR(DMSO-d$_4$): δ 8.55(s, 1H, —NH), 8.08(s, 1H, 2-H), 7.33–7.17(m, 4H, 5,8,5', 6'-H), 3.89(s, 6H, —OCH$_3$), 2.35(s, 3H, —OCH$_3$). UV(MeOH): 207.0, 232.0, 247.0, 330.0 nm. IR $υ_{max}$ (KBr): 3448, 2840, 1629, 1580, 1525, 1420, 1281 cm$^{-1}$. GC/MS m/z 454(M$^+$+1, 4.45), 453(M$^+$, 11.31), 452(M$^+$+1, 4.45), 375(20.36), 374(97.59), 373( 23.55), 372(100.00), 358(19.61), 356(18.43). Anal. (C$_{17}$H$_{15}$Br$_2$N$_3$O$_2$HCl) C, H, N.

4-(2',5'-Dibromo-4'-methylphenyl)-amino-6,7-dimethoxyquinazoline (HI-P211): Yield 83.50%; m.p. 282.0–284.0° C. $^1$H NMR-D$_6$): δ 11.30(s, H1, —NH), 8.58(s, 1H, 2-H), 8.00(s, 1H, 5-H), 7.65(s, 1H, 6'-H), 7.60(s, 1H, 3'-H), 7.13(s, 1H, 8-H), 3.79(s, 3H, —OCH$_3$), 3.78(s, 3H, —OCH$_3$), 2.29(s, 3H, —OCH$_3$). UV(MeOH): 207.0, 239.0, 330.0 nm. IR(KBr)$υ_{max}$: 3442, 2620, 1631, 1580, 1514, 1380, 1280 cm$^{-1}$. GC/MS m/z 454(M$^+$+1, 5.86), 453(M$^+$, 16.16), 452(M$^+$−1, 5.35), 374(92.12), 373(23.66), 372(100.00), 358(17.68), 356(17.35). Anal.(C$_{17}$H$_{15}$Br$_2$N$_3$O$_2$.HCl) C, H, N.

4-(3',5'-Dibromo-4'-methylphenyl)-amino-6,7-dimethoxyquinazoline (HI-P212): Yield 83.47%; m.p. 275.0–279.0° C. $^1$H NMR(DMSO-d$_6$): δ 11.30(s, 1H, —NH), 8.58(s, 1H, 2-H), 8.35(s, 1H, 5-H), 7.24(s, 2H, 2', 6'-H), 7.13(s, 1H, 8-H), 3.91(s, 3H, —OCH$_3$), 3.88(s, 3H, —OCH$_3$), 2.31(s, 3H, —CH$_3$). UV(MeOH): 237.0, 307.0, 319.0 nm. IR(KBr)$υ_{max}$: 3471, 3434, 2640, 1633, 1580, 1504, 1420, 1281 cm$^{-1}$. GC/MS m/z 454(M$^+$+1, 5.34), 453(M$^+$, 16.05), 452(M$^+$−1, 5.87), 374(99.02), 373(26.20), 372 (100.00), 358(20.39), 356(19.98), 32(8.29), 314(8.49), 206(19.02). Anal. (C$_{17}$H$_{15}$Br$_2$N$_3$O$_2$HCl) C, H, N.

4-(2'-Fluoro-4'-bromophenyl)-amino-6,7-dimethoxyquinazoline (HI-P214): Yield 77.21%; m.p. 243.0–245.0° C. $^1$H NMR(DMSO-d$_6$): δ 8.57(s, 1H, 2-H), 7.91(s, 1H, 5-H), 7.57(d, 1H, 3'-H), 7.34 (m, 2H, 5',6'-H), 7.07(s, 1H, 8-H), 3.78(s, 3H, —OCH$_3$), 3.77(s, 3H, —OCH$_3$). UV(MeOH): 204.0, 215.0, 250.0, 330.0 nm. IR(KBr)$υ_{max}$: 3431, 2629, 1633, 1580, 1511, 1420, 1278 cm$^{-1}$. GC/MS m/z 379(M$^+$+ 1, 34.39), 378(M$^+$, 21.33), 377(M$^+$−1, 39.08), 360(62.05), 359(31.58), 358(62.57), 357(19.81), 299(19.31), 298(100.00), 282(17.88), 240(28.76). Anal.(C$_{16}$H$_{13}$BrFN$_3$O$_2$.HCl) C, H, N.

4-(2', 4', 6'-Tribromophenyl)amino-6,7-dimethoxyquinazoline (HI-P222): Yield 54.86%; m.p. 250.0–255.0° C. $^1$H NMR(DMSO-d$_6$): δ 8.00(s, 1H, 2-H), 7.89(s, 2H, 3',5'-H), 7.74(s, 1H, 5-H), 7.01(s, 1H, 8-H), 3.87(s, 3H, —OCH$_3$), 3.86(s, 3H, —OCH$_3$). UV(MeOH): 209.0, 236.0, 333.0 nm. IR(KBr) $υ_{max}$: 3417, 2838, 1625, 1514, 1429, 1276, 1073 cm$^{-1}$. GC/MS m/z 519(M$^+$+1, 18.12), 518(M$^+$, 17.30), 517(M$^+$−1, 16.63), 439(M$^+$+1-Br, 99.42), 438(M$^+$-Br, 95.45), 437(M$^+$-1-Br, 100.00), 359(20.80), 358 (18.62), 357(19.32), 281(88.98), 207(15.42). Anal. (C$_{16}$H$_{12}$Br$_3$N$_3$O$_2$HCl) C, H, N.

4-(2',6'-Dibromo-4'-methylphenyl)-amino-6,7-dimethoxyquinazoline (HI-P241): Yield 79.47%, m.p. 235.0–237.0° C. $^1$H NMR(DMSO-d$_6$): δ 9.77(s, 1H, -HN), 8.20 (s, 1H, 2-H), 7.87(s, 1H, 8-H), 7.61(s, 2H, 3', 5'-H), 7.15(s, 1H, 5-H), 3.93(s, 6H, —OCH$_3$). UV(MeOH): 208.0, 245.0, 318.0, 339.0 nm. IR(KBr)$υ_{max}$: 3241, 2839, 2783, 1635, 1580, 1514, 1420, 1360, 1281 cm$^{-1}$. GC/MS m/z 454(M$^+$+1, 7.86), 453(M$^+$, 56.16), 452(M$^+$−1, 15.30), 374(95.12), 373(18.66), 372(100.00), 358(29.64). 356(19.36). Anal. (C$_{17}$H$_{15}$Br$_2$N$_3$O$_2$HCl) C, H, N.

4-(4'-Bromophenyl)-amino-6,7-dimethoxyquinazoline (HI-P260): Yield 75.28%. m.p.270.0–272.0° C. $^1$H NMR(DMSO-d$_6$) : δ 11.30(s, 1H, —NH), 8.85(s, 1H, 2-H), 8.27(s, 1H, 5-H), 7.70(s, 4H, 2',3',5',6'-H), 7.32(s, 1H, 8H), 4.02(s, 3H, —OCH$_3$), 4.00(s, 3H, —OCH$_3$). UV(MeOH):204.0, 218.0, 252.0, 335.0 nm. IR(KBr)$υ_{max}$: 3431, 3034, 2636, 1635, 1589, 1514, 1435, 1284 cm$^{-1}$. GC/MS m/z 361 (M$^+$+1, 74.00), 360(M$^+$, 100.00), 359(M$^+$−1, 72.00), 358(M$^+$−2, 95.00), 329(3.20), 301(13.0), 281(21.0), 207 (38.0). Anal. (C$_{16}$H$_{14}$BrN$_3$O$_2$.HCl) C, H, N.

4-(2'-Bromophenyl)-amino-6,7-dimethoxyquinazoline (HI-P261): Yield 71.94%; m.p.241.0–243.0° C. $^1$H NMR(DMSO-d$_6$): δ 11.67 (d, 1H, —NH), 8.79(s, 1H, 2-H), 8.32(s, 1H, 5-H), 7.86–7.38(m, 4H, 3', 4', 5',6'-H), 7.40(s, 1H, 8H), 4.01(s, 6H, —OCH$_3$). UV(MeOH): 204.0, 226.0, 248.0, 330.0 nm. IR(KBr) $υ_{max}$: 3454, 3032, 2638, 1630, 1589, 1514, 1430, 1281 cm$^{-1}$. GC/MS m/z 361 (M$^+$+1, 7.00), 360(M$^+$, 5.00), 359(M$^+$−1, 6.00), 358(M$^+$−2, 5.00), 301(13.0), 281(21.0), 280(100.00), 207(25.00). Anal. (C$_{16}$H$_{14}$BrN$_3$O$_2$.HCl) C, H, N.

4-(2',6'-Dibromophenyl)-amino-6,7-dimethoxyquinazoline (HI-P262): Yield 69.45%, mp 243.0–246.0° C, $^1$H NMR(DMSO-d$_6$): δ 11.91(d, 1H, —NH), 8.80(s, 1H, 2-H), 8.43(s, 1H, 5-H), 7.86(d, 2H, J=8.4 Hz, 3', 5'-H), 7.49(s, 1H, 8H), 7.35(t, 1H, J=8.4 Hz, 4'-H), 4.02(s, 3H, —OCH$_3$), 4.01(s, 3H, —OCH$_3$). UV(MeOH): 208.0, 227.0, 245.0, 330.0 nm. IR(KBr) $υ_{max}$: 3454, 3032, 2638, 1630, 1589, 1514, 1430, 1281 cm$^{-1}$.

4-(2',4'-Dibromophenyl)-amino-6,7-dimethoxyquinazoline (HI-P263): Yield 70.62%; m.p. 257.0–262.0° C. $^1$H NMR(DMSO-d$_6$): δ 11.91(d, 1H, —NH), 8.79(s, 1H, 2-H), 8.21(s, 1H, 5-H), 8.12–7.51(m, 3H, 3',5',6'-H), 7.35(s, 1H, 8-H), 4.01(s, 3H, —OCH$_3$), 3.99(s, 3H, —OCH$_3$). UV(MeOH):208.0, 210.0, 248.0, 330.0 nm. IR(KBr)$υ_{max}$: 3458, 3028, 2641, 1633, 1594, 1511, 1435, 1277 cm$^{-1}$.

Example 3

Chlorine Substituted Quinazoline Compounds

Chlorine substituted quinazoline derivatives were synthesized and characterized as discussed above in Example 1. The structures and physical data are shown below:

| No | Name | Structure | Formula | MW |
|---|---|---|---|---|
| 1 | P-87 | 4-(3-chlorophenylamino)-6,7-dimethoxyquinazoline | $C_{16}H_{14}ClN_3O_2$ | 316 |
| 2 | P-93 | 4-(2-hydroxy-5-chlorophenylamino)-6,7-dimethoxyquinazoline | $C_{16}H_{14}ClN_3O_3$ | 331 |
| 3 | P-189 | 4-(3,5-dichloro-4-hydroxyphenylamino)-6,7-dimethoxyquinazoline | $C_{16}H_{13}Cl_2N_3O_3$ | 365 |
| 4 | P-197 | 4-(3-chloro-4-hydroxyphenylamino)-6,7-dimethoxyquinazoline | $C_{16}H_{14}ClN_3O_3$ | 331 |
| 5 | P-268 | 4-(2-chlorophenylamino)-6,7-dimethoxyquinazoline | $C_{16}H_{14}ClN_3O_2$ | 316 |
| 6 | P-269 | 4-(4-chlorophenylamino)-6,7-dimethoxyquinazoline | $C_{16}H_{14}ClN_3O_2$ | 316 |

| No | Name | Structure | Formula | MW |
|---|---|---|---|---|
| 7 | P-278 | (structure: 4-(2-chloro-4-hydroxyphenyl)amino-6,7-dimethoxyquinazoline) | C₁₆H₁₄ClN₃O₃ | 331 |
| 8 | P-415 | (structure: 4-(4-chloronaphthalen-1-yl)amino-6,7-dimethoxyquinazoline) | C₂₀H₁₆ClN₃O₂ | 365 |

4-(3'-Chlorophenyl)-amino-6,7-dimethoxyquinazoline(HI-P87). Yield 76.98%; m.p. 242.0–245.0° C. ¹H NMR(DMSO-d₆): δ 10.47(br, s, 1H, NH), 8.69(s, 1H, 2-H), 8.06(s, 1H, 5-H), 7.95–7.23(m, 4H, 2', 4', 5'. 6'-H), 7.24(s, 1H, 8-H), 3.98(s, eH, —OCH₃), 3.35 (s, 3H, 0OCH₃). UV(MeOH): 228.0, 251.0, 332.0 nm. IR(KBr)υₘₐₓ: 3406, 2839, 1632, 1516, 1443, 1278, 1068 cm⁻¹. GC/MS m/z 316(M⁺-1, 68.34), 314(M⁺-2, 100.00, 344 (11.34), 222(4.35), 140(9.86). Found: C, 54.62; H, 4.68; N, 11.93; Cl, 19.23. C₁₆H₁₄ClN₃O₂. HCl requires: C, 54.70; H, 4.28; N, 11.96; Cl, 19.96%.

4-(c'-Chloroo-6'-hydroxyphenyl)amino-6,7-dimethoxyquinazoline(HI-P93) Yield 83.08%; m.p. 295.0° C.(dec). ¹H NMR9DMSO-d₆: δ 10.14(s, 1H, —OH), 8.37(s, 1H, 2-H), 7.78 (s, 1H, 5H), 7.57(d, 1H, J₂',₄'=2.4 Hz, 2'-H),), 7.16(s, 1H, 8-H), 7.07(dd, 1H, J₂',₄'=2.4Hz, J₄',₅'=8.7Hz, 4'-H), 6.92(d, 1H, J₄',₅'=8.7Hz, 5'-H), 3.93(s, 3H, —OCH₃). 3.92(s, 3H, —OCH₃). UV(MeOH): 205, 229.0, 251.0, 320.0 nm. IR(KBr)υₘₐₓ: 3500(br), 3430, 2835, 1622, 1512, 1432, 1259 cm⁻¹. GC/MS m/z 333(M⁺+2, 13.41), 332(M⁺+1, 9.73, 331(M⁺, 39.47), 314(M⁺—OH, 100.00), 298(7.64). Found: C, 52.25; H, 4.07; N, 11.39. C₁₆H₁₄ClN₃O₃.HCl requires: C, 52.32; H, 4.09; N. 11.44%.

4-(4'-Hydroxyl-3',5'-dichlorophenyl)amino-6,7-dimethoxyquinazoline(HI-P189) Yield 79.45%; m.p. 293.0–295.0° C. ¹HNMR-DMSO-d₆): δ 11.32(s, 1H, —NH), 10.34(s, 1H, —OH), 8.87(s, 1H, 2-H), 8.29(s, 1H, 5-H), 7.90(s, 2H, 2', 6'-H), 7.32(s, 1H, 8-H), 4.01(s, 3H, —OCH₃), 3.99(s, 3H, —OCH₃). UV(MeOH): 213.0, 232.0, 250.0, 335.0 nm. IR(KBr)υₘₐₓ: 3479, 2564, 1641, 1579, 1429, 1282, 1147 cm⁻¹. GC/MS m/z 367(M⁺=2, 66.57), 366(M⁺=1, 75.91), 365(M⁺, 100.00), 364(M⁺-1, 94.08), 349(M⁺—OH, 11.16). Anal. (C₁₆H₁₃Cl₂N₃O₃) C, H, N. Found: C, 48.93; H, 4.51; N, 10.00. C₁₇₀H₁₇Cl₂N₃O₃. Hcl requires: C, 48.80; H, 4.31; N, 10.04. %.

4-(3'-Chloro-4'-hydroxylphenyl)-amino-6,7-dimethoxyquinazoline(HI-P197). Yield 84.14%; m.p. 245.0° C.(dcc). ¹H NMR(DMSO-d₆): δ 10.00(s, 1H, —NH), 9.37(s, 1H, —OH), 8.41(s, 1H, 2-H), 7.78(s, 1H, 5-H), 7.49(d, 1H, J₂',₅=2.7Hz, 2'-H), 7.55(dd, 1H, J₅',₆=9.0Hz, J₂',₆=2.7Hz, 6'-H), 7.16(s, 1H, 8-H), 6.97(d, 1H, J₅',₆=9.0Hz, 5'-H), 3.93(s, 3H, —OCH₃), 3.91(s, 3H, —OCH₃). UV(MeOH): 209.0, 224.0, 249.0, 330.0 nm. IR(KBr)υₘₐₓ: 3448, 2842, 1623, 1506, 1423, 1241 cm⁻¹. GC/MX m/z: 341(M⁺, 100.00), 326(M⁺—CH₃, 98.50), 310(M⁺—OCH₃, 12.5), 295(9.0.), 189(13.5), 155(13.8). Found: C, 521.35; H, 4.16; Cl, 19.15; N, 11.39. C₁₆H₁₄ClN₃O₃. HCl requires: C, 52.32; H, 4.09; Cl, 19.07; N, 11.44%.

4-(2'-Chlorophenyl)-amino-6,7-dimethoxyquinazoline(HI-P268) Yield 87.28%; m.p. 247.0–279.5° C. ¹H NMR(DMSO-d₆): δ 11.71(s, 1H, -NH), 8.78(s, 1H, 2-H), 8.33(s, 1H, 5-H), 7.67(s, 1H, 8H), 7.68–7.42(m, 4H, 3',4,5,6'-H), 4.00(s, 3H —OCH₃), 3.99(s, 3H, —OCH₃). UV(MeOH): 213.0, 234.0, 251.0, 331.0 mn. IR(KBr)υₘₐₓ: 3479, 2566, 1643, 1577, 1429, 1282, 1147 cm⁻¹. GC/MX m/z 317(M⁺+1, 6.60), 316(M⁺, 6.60), 315(M⁺-1, 18.52), 314(M⁺-2, 11.11), 281(21.22), 280(M⁺—Cl, 100.00), 264(29.62). Found: C, 54.51; H, 4.41; N, 11.81. C₁₆H₁₄ClN₃O₂. HCl requires: C, 54.45; H, 4.26; N, 11.93%.

4-(4'-Chlorophenyl)-amino-6,7-dimethoxyquinazoline(HI-P269) Yield 94.94%. m.p. 248.0–250.0° C. ¹H NMR(DMSO-d₆): δ 11.62(s, 1H, -NH), 8.85(s, 1H, 2-H), 8.42(s, 1H, 5-H), 7.88(d, 2H, J=8.7Hz, 3',5',-H), 7.54(d, 2H, J=8.7Hz, 2',6',-H), 7.38(s, 1H, 8-H0, 4.02(s, 3H, —OCH₃), 3.99(s, 3H, —OCH₃). UV(MeOH): 215.0, 230.0, 253.0, mn. IR(KBr)υₘₐₓ: 3477, 2563, 1640, 1578 cm⁻¹. GC/MX m/z 317(M⁺1, 18.18), 316(M⁺, 29.55), 315(M⁺-1, 48.85), 314(M⁺-2, 61.36), 281(32., 95), 207(100.00). Found: C, 54.65; H, 4.38; N, 11.92. C₁₆H₁₄ClN₃O₂. HCl requires: C, 54.55; H, 4.26; N, 11.93%.

-continued

| No | Name | Structure | Formula | MW |
|---|---|---|---|---|

4-(4'-Hydroxyl-2'-chlorophenyl)-amino-6,7-dimethoxy-quinazoline(HI-P278) Yield 81.44%; m.p. 245.0–247.0° C. $^1$H NMR(DMSO-$d_6$): δ 11.39(s, 1H, —NH), 10.30(s, 1H, —OH), 8.75(s, 1H, 2-H), 8.24(s, 1H, 5-H), 7.38–6.85(m, 3H, 3',5',6'-H), 7.37(s, 1H, 8H), 3.98(s, 3H, —OCH$_3$), 3.96(s, 3H, —OCH$_3$). UV(MeOH): 222.0, 234.0, 239.0, 245.0, 254.0, 348.0 nm. IR(KBr)$\upsilon_{max}$: 3448, 3242, 3144, 3025, 2917, 2834, 1638, 1591, 1514, 1437, 1365, 1277, 1209 cm$^{-1}$. GC/MS m/z: 332(M$^+$+1, 5.00), 331(M$^+$, 17.00), 330(M$^+$−1, 5.00), 297(17.00), 296(100.00), 281(18.00), 280(29.00), 253(9.00). Found: C, 52.17; H, 4.06; N, 11.32. C$_{16}$H$_{14}$ClN$_3$O$_3$. HCl requires: C, 52.32; H, 4.01; N, 11.44%.

4-(4'-Chloronaphthy-1')-amino-6,7-dimethoxyquinazoline(HI-P415) Yield, 85.07%. m.p. 245.0–248.0°C. $^1$H NMR(DMSO-$d_6$): δ 11.91(s, 1H, —NH), 8.66(s, 1H, 2-H), 8.45(s, 1H, 5-H), 8.30–7.62(m, 6H, 2', 3', 5', 6', 7', 8'-H), 7.38(s, 1H, 8-H), 4.03(s, 3H, —OCH$_3$), 4.01(s, 3H, —OCH$_3$). UV(MeOH): 211.0, 233.0, 250.0, mn. IR(KBr)$\upsilon_{max}$: 3481, 2567, 1645, 1579 cm$^{-1}$. Found: C, 59.32; H, 4.27; N, 10.24. C$_{20}$H$_{16}$ClN$_3$O$_2$. HCl. requires: C, 59.70; H, 4.23; N, 10.48%.

Example 4

Iodine Substituted Quinazoline Compounds

Iodine substituted quinazoline derivatives were synthesized as discussed above in Example 1, and analyzed. The structures and physical data are shown below:

| No | Name | Structure | Formula | MW |
|---|---|---|---|---|
| 1 | P-270 | 4-(2'-iodophenyl)amino-6,7-dimethoxyquinazoline | C$_{16}$H$_{14}$IN$_3$O$_2$ | 407 |
| 2 | P-271 | 4-(3'-iodophenyl)amino-6,7-dimethoxyquinazoline | C$_{16}$H$_{14}$IN$_3$O$_2$ | 407 |
| 3 | P-300 | 4-(4'-iodophenyl)amino-6,7-dimethoxyquinazoline | C$_{16}$H$_{14}$IN$_3$O$_2$ | 407 |
| 4 | P-294 | 4-(3',5'-diiodo-4'-hydroxyphenyl)amino-6,7-dimethoxyquinazoline | C$_{16}$H$_{13}$I$_2$N$_3$O$_3$ | 549 |

-continued

Iodine Substituted Quinazoline Compounds

| No | Name | Structure | Formula | MW |
|----|------|-----------|---------|-----|
| 5 | P-299 | (structure) | $C_{16}H_{14}IN_3O_3$ | 423 |

4-(2'-Iodophenyl)-amino-6,7-dimethoxyquinazoline(P-270): Yield 75.37%; m.p. 225.0–230.0° C. $^1$H NMR(DMSO-d$_6$): δ 11.74(s, 1H, —NH), 8.79(s, 1H, 2-H), 8.33(s, 1H, 5-H), 8.05–7.13(m, 4H, 3',4,5,6'-H), 7.44(s, 1H, 8H), 4.01(s, 6H, —OCH$_3$). UV(MeOH): 219.0, 222.0, 253.0, 342.0 nm. IR(KBr)υ$_{max}$: 3165, 3027, 2827, 1639, 1572, 1501, 1434, 1275, 1070 cm$^{-1}$. GC/MS m/z 408(M$^+$+1, 3.47), 407(M$^+$, 15.28), 406(M$^+$-1, 3.47), 281(33.33), 280(M$^+$-1, 100.00), 264(50.00), 207(34.72). Found: C, 43.62; H, 3.60; N, 9.42. $C_{16}H_{14}IN_3O_2$. HCl requires: C, 43.34; H, 3.38; N, 9.48%.

4-(3'-Iodophenyl)-amino-6,7-dimethoxyquinazoline(HI-P271): Yield 79.85%; m.p. 235.0–242.0° C. $^1$H NMR(DMSO-d$_6$): δ 11.43(s, 1H, —NH), 8.88(s, 1H, 2-H), 8.33(s, 1H, 5-H), 8.13(s, 1H, 2'-H), 7.80–7.26(m, 3H, 4',5',6'-H), 7.35(s, 1H, 8H), 4.02(s, 3H, —OCH$_3$), 4.00(s, 3H, —OCH$_3$). UV(MeOH):.203.0, 210.0, 228.0, 251.0, 331.0 nm. (KBr)υ$_{max}$: 3191, 3022, 2940, 2836, 2576, 1629, 1516, 1444, 1276, 1153, 1060 cm$^1$. GC/MS m/z 406(M$^+$, 1.52), 405(M$^+$-1, 6.22), 281(35.33), 207(100.00). Found: C, 43.55; H, 3.43; N, 9.32. $C_{16}H_{14}IN_3O_2$. HCl requires: C, 43.34; H, 3.38; N, 9.48%.

4-(4'-Hydroxy-3,5-diiodophenyl)-amino-6,7-dimethoxy-quinazoline(HI-P294: Yield 77.47%; m.p. 259.0–260.0° C. $^1$H NMR(DMSO-d$_6$): δ 11.13(s, 1H, NH), 9.73(s, 1H, —OH), 8.87(s, 1H, 2-H), 8.16(s, 1H, 5-H), 8.09(s, 2H, 2', 6'-H), 7.28(s, 1H, 8H), 3.98(s, 6H, —OCH$_3$). UV(MeOH)λ$_{max}$(ε):. 217.0, 227.0, 252.0 nm. IR(KBr)υ$_{max}$: 3457, 3201, 2934, 2832, 2566, 1629, 1562, 1521, 1439, 1275, 1075 cm$^{-1}$. GC/MS m/z: GC/MS m/z 422(M$^+$-I, 33.53), 405(7.50), 281(86.67), 221(51.80), 207(91.30). Found: C, 32.60; H, 2.50; N, 6.92. $C_{16}H_{13}I_2N_3O_3$. HCl requires: C, 32.82; H, 2.39; N, 7.18%.

4-(4'-Hydroxy-3'-iodophenyl)-amino-6,7-dimethoxyquinazoline(HI-P299) Yield 71.59%; m.p. 248.0–250.0° C. $^1$H NMR(DMSO-d$_6$): δ 11.32(d, 1H, NH), 10.62(s, 1H, —OH, 8.79 (s, 1H, 2-H), 8.26(s, 1H, 5-H), 7.98 – 6.98(m, 3H, 2',3',6'-H), 7.32(s, 1H, 8H), 3.98(s, 3H, —OCH$_3$), 3.97(s, 3H, —OCH$_3$). UV(MeOH)λ$_{max}$(ε): 217.0, 227.0, 252.0 nm. IR(KBr)υ$_{max}$: 3411, 2975, 2730, 2366, 1634, 1573, 1501, 1429, 1229, 1075 cm$^{-1}$. GC/MS m/z: 406(M$^+$-1, 3.33), 405(M$^+$-2, 7.50), 281(M$^+$-1-I, 26.67), 253(11.80), 207 (100.00). Found: C, 41.96; H, 3.40; N, 8.98. $C_{16}H_{14}IN_3O_3$. HCl requires: C, 41.83; H, 3.26; N, 9.15%.

4-(4'-Iodophenyl)-amino-6,7-dimethoxyquinazoline(HI-P300): Yield 85.24%; m.p. 240.0–242.0° C. $^1$H NMR(DMSO-d$_6$): δ 11.51(s, 1H, NH), 8.82(s, 1H, 2-H), 8.37(s, 1H, 5-H), 7.81(d, 2H, J=8.4Hz, 2', 6'-H), 7.55(d, 2H, J=8.4Hz, 3', 5'-H), 7.35(s, 1H, 8H), 4.01 (s, 3H, —OCH$_3$), 3.98(s, 3H, —OCH$_3$). UV(MeOH):. 217.0, 227.0, 252.0 nm. IR(KBr) υ$_{max}$: 3211, 3032, 2832, 2720, 1629, 1573, 1501, 1434, 1235, 1153, 1070 cm$^{-1}$. GC/MS m/z 406(M$^+$-1, 3.33), 405(M$^+$-2, 7.50), 281(M$^+$-1 -I, 26.67), 253(11.80), 207(100.00). Found: C, 43.40; H, 3.39; N, 9.36. $C_{16}H_{14}IN_3O_2$.HCl. requires: C, 43.34; H, 3.38; N, 9.48%.

Example 5

OH Group Substituted Quinazoline Compounds

OH group substituted quinazoline derivatives were synthesized and characterized as discussed above for Example 1. The structures and physical data are shown below:

| No | Name | Structure | Formula | MW |
|----|------|-----------|---------|-----|
| 1 | P-93 | (structure) | $C_{16}H_{14}ClN_3O_3$ | 331 |

| No | Name | Structure | Formula | MW |
|---|---|---|---|---|
| 2 | P-97 | 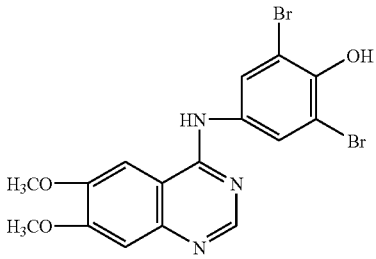 | $C_{16}H_{13}Br_2N_3O_3$ | 455 |
| 3 | P-131 | 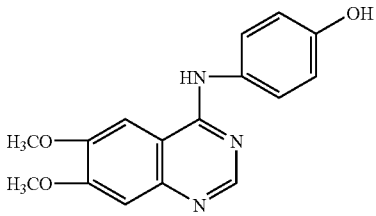 | $C_{16}H_{15}N_3O_3$ | 297 |
| 4 | P-132 | 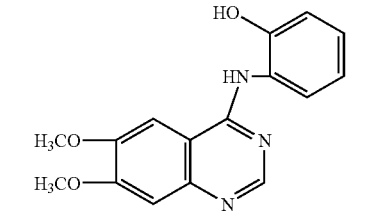 | $C_{16}H_{15}N_3O_3$ | 297 |
| 5 | P-133 | 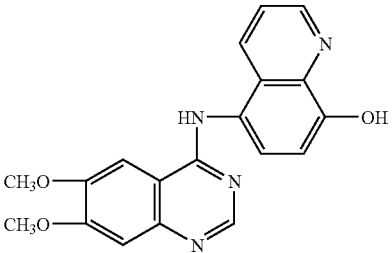 | $C_{19}H_{16}N_4O_3$ | 348 |
| 6 | P-150 | 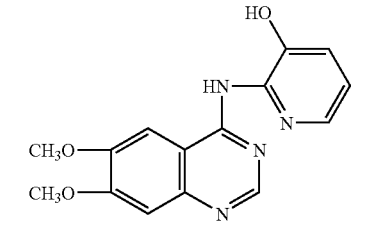 | $C_{15}H_{14}N_4O_3$ | 298 |
| 7 | P-154 | 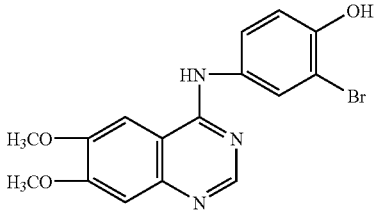 | $C_{16}H_{14}BrN_3O_3$ | 376 |

-continued

| No | Name | Structure | Formula | MW |
|---|---|---|---|---|
| 8 | P-180 | 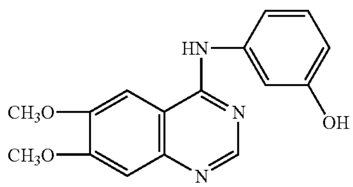 | $C_{16}H_{15}N_3O_3$ | 297 |
| 9 | P-182 | 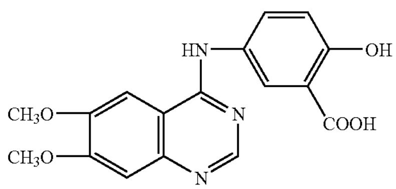 | $C_{17}H_{15}N_3O_5$ | 341 |
| 10 | P-189 | 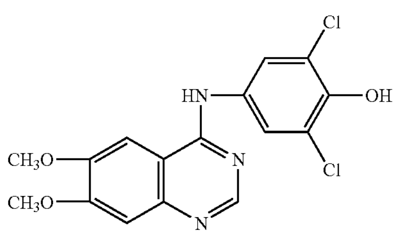 | $C_{16}H_{13}Cl_2N_3O_3$ | 365 |
| 11 | P-190 | 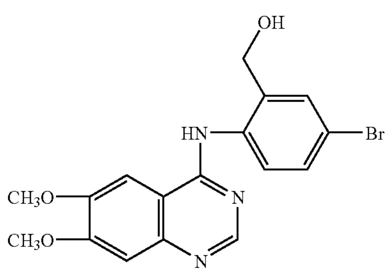 | $C_{17}H_{16}BrN_3O_3$ | 389 |
| 12 | P-191 | 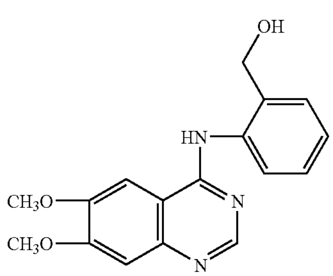 | $C_{17}H_{17}N_3O_3$ | 311 |
| 13 | P-192 | 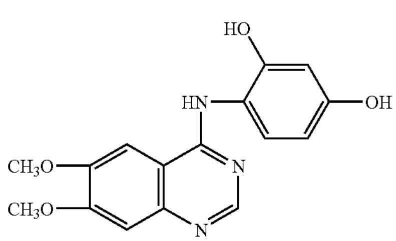 | $C_{16}H_{15}N_3O_4$ | 313 |

-continued

| No | Name | Structure | Formula | MW |
|---|---|---|---|---|
| 14 | P-197 | 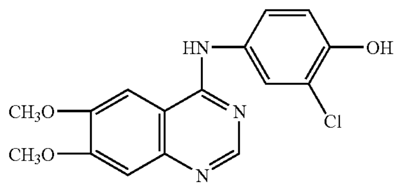 | C₁₆H₁₄ClN₃O₃ | 331 |
| 15 | P-215 | 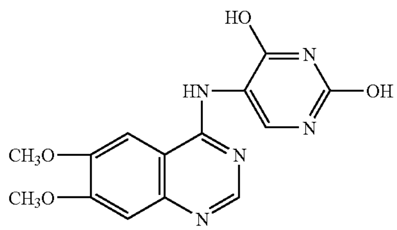 | C₁₄H₁₃N₅O₄ | 315 |
| 16 | P-259 | 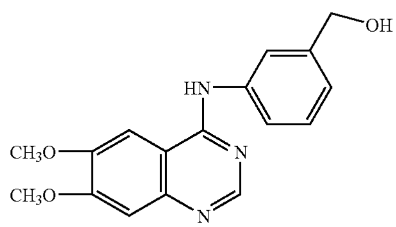 | C₁₇H₁₇N₃O₃ | 311 |
| 17 | P-265 | 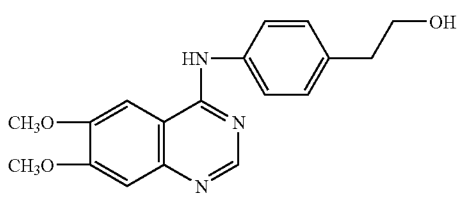 | C₁₈H₁₉N₃O₃ | 325 |
| 18 | P-266 | 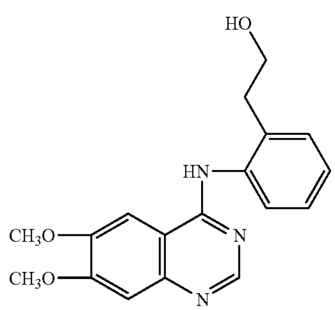 | C₁₈H₁₉N₃O₃ | 325 |
| 19 | P-274 | 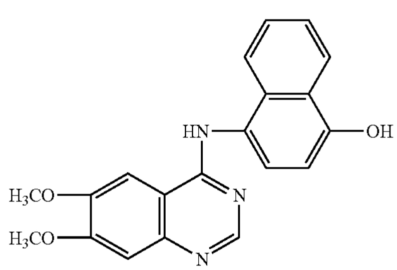 | C₂₀H₁₇N₃O₃ | 347 |

-continued

| No | Name | Structure | Formula | MW |
|---|---|---|---|---|
| 20 | P-275 | 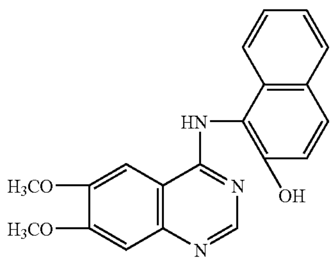 | $C_{20}H_{17}N_3O_3$ | 347 |
| 21 | P-276 | 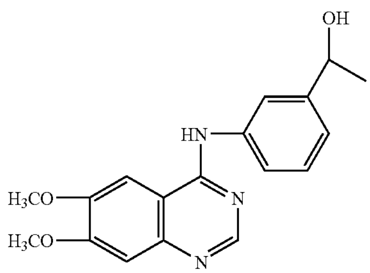 | $C_{18}H_{19}N_3O_3$ | 325 |
| 22 | P-277 | 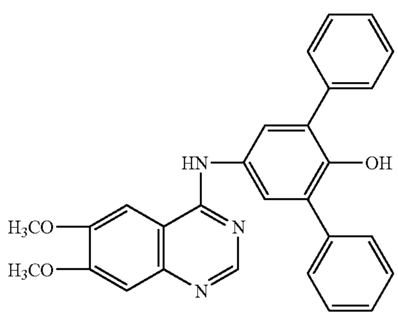 | $C_{28}H_{23}N_3O_3$ | 449 |
| 23 | P-278 | 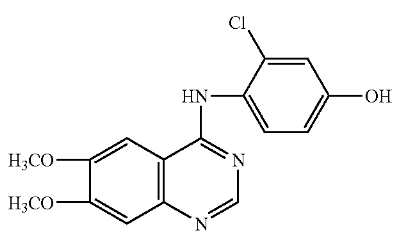 | $C_{16}H_{14}ClN_3O_3$ | 331 |
| 24 | P-289 | 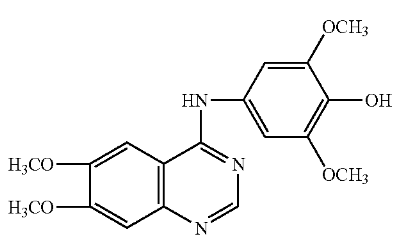 | $C_{18}H_{19}N_3O_5$ | 357 |
| 25 | P-292 | 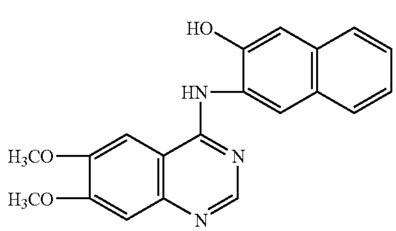 | $C_{20}H_{17}N_3O_3$ | 341 |

-continued

| No | Name | Structure | Formula | MW |
|---|---|---|---|---|
| 26 | P-293 | 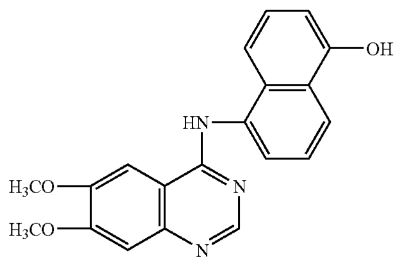 | C₂₀H₁₇N₃O₃ | 341 |
| 27 | P-294 | 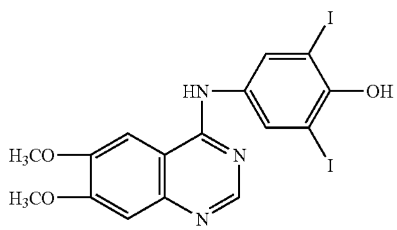 | C₁₆H₁₃I₂N₃O₃ | 549 |
| 28 | P-229 | 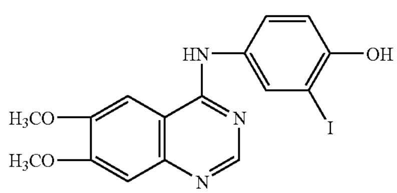 | C₁₆H₁₄IN₃O₃ | 423 |
| 29 | P-312 | 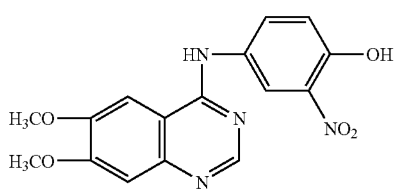 | C₁₆H₁₄N₄O₅ | 342 |
| 30 | P-313 | 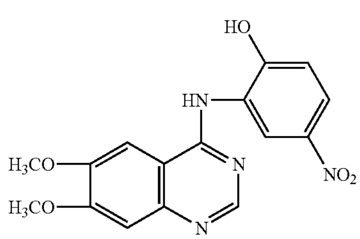 | C₁₆H₁₄N₄O₅ | 342 |
| 31 | P-315 | 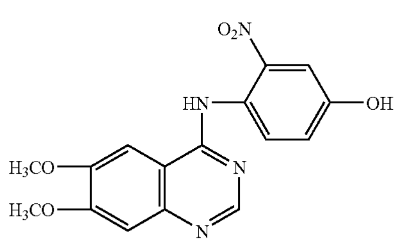 | C₁₆H₁₄N₄O₅ | 342 |

-continued

| No | Name | Structure | Formula | MW |
|----|------|-----------|---------|-----|
| 32 | P-323 | 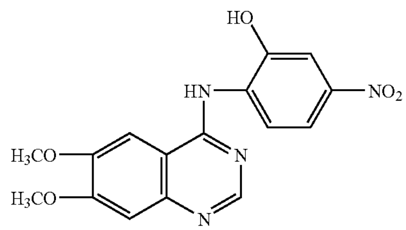 | $C_{16}H_{14}N_4O_5$ | 342 |

4-(3'-Chlooro-6'-hydroxylphenyl)amino-6,7-dimethoxyquinazoline(HI-P93) yield 93.08%; m.p. 295.0° C.(dec). $^1$H NMR-DMSO-$d_6$: δ 10.14(s, 1H, —NH), 9.16(s, 1H, —OH), 8.37(s, 1H, 2-h), 7.78(s, 1H, 5H), 7.57(d. 1H, J$_{2',2'}$=2.4Hz, 2'-H),), 7.16(s, 1H, 8-H), 7.07(dd. 1H, J$_{2',2'}$=2.4Hz, J$_{4', 5'}$=8.7Hz, 4'-H), 6.92(d, 1H, J$_{4',5'}$=8.7Hz, 5'-H), 3.93(s, 3H, —OCH$_3$). 3.92(s, 3H, —OCH$_3$. UV(MeOH): 205, 229.0, 251.0, 320.0 nm. IR(KBr)$\upsilon_{max}$: 3500(br), 3430, 2835, 1622, 1512, 1432, 1259 cm$^{-1}$. GC/MS m/z 333(M$^-$=2, 13.41), 332(M$^-$=1, 9.73), 331(M$^+$, 39.47), 314(M$^+$-OH, 100.00). 298(7.64). Found: C, 52.25; H, 4.07; N, 11.39, $C_{16}H_{14}ClN_3O_3$, HCl requires: C, 52.32; H, 4.09; N, 11.44%.

4-(3',5'-Dibromo-4'-hydroxylphenyl)-amino-6,7-dimethoxyquinazoline-(HI-P97). Yield 72.80%; m.p.>300.0° C. $^1$H NMR(DMSO-$d_6$): δ 9.71(s, 1H, —NH), 9.39(s, 1H, —OH), 8.48(s, 1H, 2-h), 8.07(s, 2H, 2', 6'-H), 7.76(s, 1H, 5-H), 7.17(s, 1H, 8-H), 3.94(s, 3H, —OCH$_3$, 3.91(s, 3H, —OCH$_3$). UV(MeOH): 208.0, 210.0, 245.0, 320.0 nm; IR(KBr)$\upsilon_{max}$: 3504(br), 3419, 2868, 1627, 1512, 1425, 1250, 1155 cm$^{-1}$; GC/MS m/z 456(M$^1$=1, 54.40), 455(M$^-$, 100.00), 454(M$^-$, 78.01), 439(M$^-$—OH, 7.96), 376(M$^-$+1-Br, 9.76), 375(M$^-$Br, 10.91), 360(5.23). Anal. ($C_{16}H_{13}Br_2N_3O_3$) C, H, N.

4-(4'-Hydroxylphenyl)-amino-6,7-dimethoxyquinazoline(HI-P131): yield 84.29%; m.p. 245.0–248.0° C. IR(KBr)$\upsilon_{max}$: 3428, 2836, 1635, 1516, 1443, 1234 cm: $^1$H NMR(DMSO-$d_6$): δ 11.21(s, 1H, —NH), 9.70(s, 1H, —OH), 8.74(s, 1H, 2-h), 8.22(s, 1H, 5-H), 7.40(4, 2H, J=8.9Hz, 2', 6'-H), 7.29(s, 1H, 8-H), 6.85(d, 2H, J=8.9Hz, 3', 5'-H), 3.98(s, 3H, —OCH$_3$, 3.97(s, 3H, —OCH$_2$). GC/MS m/z 298 (M$^-$=1, 100.00), 297(M$^-$, 26.6), 296(M$^+$-1, 12.5). Anal. ($C_{16}H_{15}N_3O_3$HCl) Cl, H, N.

4-(2'-Hydroxylphenyl)-amino-6,7-dimethoxyquinazoline(HI-P132): yield 82.49%; m.p. 255.0–258.0° C. IR(KBr)$\upsilon_{max}$: 3500(br), 3425, 2833, 1625, 1512, 1456, 1251, 1068 cm$^{-1}$. $^1$H NMR(DMSO-$d_6$): δ 9.78(s, 1H, —NH), 9.29(s, 1H, —OH), 8.33(s, 1H, 2-h), 7.85(s, 1H, 5-H), 7.41–6.83(m, 4H, 3',4',5',6'-H), 7.16(s, 1H, 8-H), 3.93(s, 3H, —OCH$_3$, 3.92(s, 3H, —OCH$_3$), 280 (M$^+$—OH, 10.0). Anal. ($C_{16}H_{15}N_3O_3$, HCl) C, H, N.

4-[(8'-Hydroxyquiline)-5'-Jamino-6,7-dimethoxyquinazoline(HI-P133) yield 83.51%; m.p. 238.0–239.0° C. $_1$H NME(DMSO-$d_6$): δ 10.12(br, s, 1H, —NH), 8.93–7.09 M, 8H, 2, 5, 2, 2', 3', 4',6', 7'-H), 4.04(s, 3H, —OCH$_3$), 3.96(s, 3H, —OCH$_3$). UV(MeOH): 204.0, 245.0, 332.0 nm. IR(KBr)$\upsilon_{max}$: 3425(br), 2935, 1632, 1510, 1437, 1273 cm$^{-1}$. GC/MS m/z 349(M$^-$=1, 100.00), 348 (m+, 26.56), 307(38.50), 289(21.00).

4-[(3'-Hydroxylpyridine)-2']-amino-6,7-dimethoxyquinazoline(HI-P150) Yield 78.65%; m.p. 185.0–187.0° C. $^1$H NMR(DMSO-$d_6$): δ 10.08(br, s, 1H, —NH), 8.52(s, 1H, 2-H), 7.88–7.86(m, 1H, 6'-H), 7.60(s, 1H, 5-H), 7.39–7.35(m, 1H, 4'-H), 7.32(s, 1H, 8-H), 6.63–6.58(m, 1H, 5'-H), 5.96(s, 1H, —OH), 3.97(s, 3H, —OCH$_3$), 3.94(s, 3H, —OCH$_3$). UV(MeOH): 204.0, 238.0, 321.0 nm. IR(KBr)$\upsilon_{max}$: 3500, 3446, 2960, 1475, 1236, 1375, 1182 cm$^{-1}$. GC/MS m/z 299(M$^-$=1, 100), 298(M$^+$, 34), 289(11), 291(9). Found: C, 60.26; H, 4.81; N, 18.68. $C_{15}H_{14}N_4O_5$, requires: C, 60.26; H, 4.81; N, 18.68%.

4-(3'-Bromo-4'-hydroxylphenyl)-amino-6,7-dimethoxyquinazoline(HI-P154); yield 89.90%; m.p. 233.0–233.5° C. $^1$H NMR(DMSO-$d_6$): 10.08(s, 1h, —NH), 9.38(s, 1H, —OH), 8.40(s, 1H 2-H), 7.89(d, 1H, J$_{2',6'}$=2.7Hz, 2'-H), 7.75(s, 1H, 5-h), 7.55(dd, 1H, J$_{5',6'}$=9.0Hz, J$_{2',6'}$=2.7Hz, 6'-H), 7.14 (s, 1H, 8-H), 6.97(d, 1H, J$_{5',5'}$=9.0Hz, 5'-H), 3.92(s, 3H, OCH$_3$), 3.90(s, 3H, —OCH$_3$). UV(MeOH): 203.0, 222.0, 25.0, 335.0 nm. IR(KBr)$\upsilon_{max}$: 3431(br), 2841, 1624, 1498, 1423, 1244 cm$^1$. GC/MS m/z 378(M$^+$=2, 90.68), 377(M$^+$=1, 37.49), 376(M$^+$, 100.00), 360(MK$^+$, 3.63) 298 (28.86), 282(6.65). Anal. ($C_{16}H_{14}BrN_3O_3$,HCl) C, H, N.

4-(3'-Hydroxyphenyl)-amino-6,7-dimethoxyquinazoline(HI-P180) Yield 71.55%; m.p. 256.0–258.0° C. IR(KBr)$\upsilon_{max}$: 3394, 2836, 1626, 1508, 1429, 1251 cm$^{-1}$. $^1$H NMR(DMSO-$d_6$): 9.41(s, 1H, —NH), 9.36(s, 1H, —OH), 8.46(s, 1H, 2-H), 7.84(s, 1H, 5-H), 7.84–6.50(m, 4H, 2', 4', 5', 6'-H), 7.20(s, 1H, 8-H), 3.96(s, 3H, —OCH$^3$), 3.93(s, 3H —OCH$_3$). GC/MS m/z: ($C_{16}H_{15}N_3O_3$.HCl) C, H, N.

4-(4'-Hydroxyl-3'-Carboxyphenyl)-amino-6,7-dimethoxyquinazoline(HI-P182) Yield 79.25%; m.p.>300.0° C. $^1$H NMR(DMSO-$d_6$)I: δ 10.53(s, 1H, —NH), 8.53(s, 1H, 2-H), 8.10–78.2(m, o3H, 2', 5', 6', —H), 7.26(s, 1H, 5-H), 6.9(s, 1H, 80H), 4.01(s, 3H, —OCH$_3$), 3.99(s, 3H, —OCH$_3$). UV(MeOH): 210.0, 239.0, 335.0 nm. IR(KBr)$\upsilon_{max}$ 3421, 2839, 1686, 1631, 1508, 1491, 1280 cm$^{-1}$. GC/MS m/z 341(M$^+$, 7.91), 323(M$^+$—OH, 12.19), 297(M$^+$—COOH, 12.35), 296(M$^+$—COOH -1.1760), 295(M$^+$—COOH-2, 28.65), 206(11.28).

4-(4'-Hydroxyl-3',5'-dicholophenyl)-6,7-dimethoxyquinazoline(HI-P189) Yield 79.45%; m.p. 293.0–295.0° C. $^1$H NMR(DMSO-$d_6$): 11.32(s, 1H, —NH), 10.34(a, 1H, —OH), 8.87(s, 1H, 2-H), 8.29(s, 1H, 5-H), 7.90(s, 2H, 2', 6'-H), 7.32(s, 1H, 8-H), 4.01(s, 3H, —OCH$_3$), 3.99(s, 3H, —OCH$_3$). UV(MeOH): 213.0, 232.0, 250.0, 335.0 nm. IR(KBr)$\upsilon_{max}$: 3479, 2564, 1641, 1579, 1429, 1282, 1147 cm$^{-1}$. GC/MS m/z 367(M$^+$+2; 66.57), 366(M$^+$+1, 75.91), 365(M$^+$, 100.00), 364 (M$^+$-1, 94.08), 349(M$^-$OH, 11.16). Anal. ($C_{16}H_{13}Cl_2N_3O_3$) C, H, N. Found: C, 48.93; H, 4.51; N, 10.00. —H$_1$—Cl$_2$N$_3$O$_3$. HCl requires: C, 48.80; H, 4.31; N, 10.04%.

-continued

| No | Name | Structure | Formula | MW |
|----|------|-----------|---------|-----|

4-(4'-Bromo-6'-hydroxymethylphenyl)-amino-6,7-dimethoxyquinazoline(HI-P190) Yield 7o3.08%; m.p. 222.0–223.0° C. $^1$H NMR(DMSO-d$_6$): δ 11.30(s, 1H, —OH), 8.22(s, 1H, —NH)O, 7.77.7.23 (m, 5H, 5, 8, 2', 3', 5'-H), 4.49(s, 2H, PhCH$_2$-H), 4.01(s, 3H, —OCH$_3$), 3.90(s, 3H, —OCH$_3$). UV(MeOH): 207.0, 250.0, 332.0 nm. IR(KBr)$\upsilon_{max}$: 3446, 2829, 2752, 1652, 1560, 1471, 1365, 1280 cm$^{-1}$. GC/MS m/z 391(M$^-$=1, 29.33), 389(M$^-$, 29.82), 360(M$^-$CH$^2$OH, 50.76), 358(52.39), 311(18.33). 280(43.20), 206(62.80), 191(100.00). Anal. (C$^{17}$H$^{16}$BrN$_3$O$_3$.HCl) C, H, N.

4-(6'-Hydroxymethylphenyl)-amino-6,7-dimethosyquinazoline(HI-P191) Yield 78.45%; m.p. 215.0–218.0° C. $^1$H NMR(DMSO-d$_6$): δ 11.54(s, 1H, —NH)O, 8.70(s, 1H, 2-H), 8.34(s, 1H, 5-H), 7.62–7.33(m, 4H, 3', 4', 5', 6'-H), 7.39(s, 1H, 8-H), 4.49(s, 2H, PhCH$_2$OH), 3.99(s, 3H, —OCH$_3$), 3.98(s, 3H, —OCH$_3$). UV9MeOH): 209.0, 224.0, 246.0, 335.0 nm. IR(KBr)$\upsilon_{max}$: 3421, 2941, 1675, 2606, 128, 1508, 1437o, 1244 cm$^{-1}$. GC/MS m/z 311(M$^-$, 38.07), 310(M$^-$-1, 27.04), 2800 (M$^+$CH$_2$OH, 100.00), 206(17.24), 191(51.34).

4-(2',4'-Dihydroxyphenyl)-amino-6,7-dimethoxyquinazoline (HI-P192) Yield 86.25%; m.p. 240.0° C.(dec). $^1$H NMR(DMSO-d$_6$): 10.92(s, 1H, —NH), 976(s, 1H, —OH), 9.59(s, 1H, —OH), 8.67(s, 1H, 20H), 81.9(s, 1H, 8-H), 7.36(s, 1H, 50H), 705(d, 1H, J – 8.7Hz, 1'-H), 6.51(s, 1H, 5'-H), 6.31 (d, 1H, J = 8.7Hz, 3'-H), 3.98(s, 6H, —OCH$_3$). UV(MeOH): 206.0, 209.0, 223.0, 250.0, 342.0, 486 nm. IR(KBR)$\upsilon_{max}$: 3391, 3139, 2938, 2850, 1633, 1607, 1567, 1509, 1447, 1359, 1220, 1189, 1055 cm$^{-1}$. GC/MS m/z 314 (M$^-$=1, 13.00), 313(m$^-$, 72.80), 312(m$^+$-1, 10.20), 296(5.24), 206 (17.50).

4-(2',3'-Dihydroxyphenyl)-amino-6,7-dimethoxyquinazoline (HI-P192) Yield 86.25%; m.p 240.0° C.(dec). $^1$H NMR(DMSO-d$_6$): 10.00(s, 1H, —NH), 9.37(s, 1H, —OH), 8.41(s, 1H, 2-H), 7.78(s, 1H, 5-H), 7.49(d, 1H, J$_{2',3}$=2.7Hz, 2'-H), 7.55(dd, 1H, J$_{5',6}$=9.0Hz, J$_{2',6}$2.7Hz, 6'-H), 7.16(s, 1H, 8-H), 6.97(d, 1H, J$_{5',6}$=9.0Hz, 5'-h), 3.93(s, 3H, —OCH$_3$), 3.91(s, 3H, —OCH$_3$). UV9MeOH): 209.0, 224.0, 249.0, 330.0 nm. IR(KBr)$\upsilon_{max}$: 3448, 2842, 1623, 1506, 1423, 1241 cm$^{-1}$. GC/MS m/z: 341(M$^+$, 100.00), 326(M$^-$CH$_3$, 98.50), 310(M$^+$—OCH$_3$, 12.5), 295(9.0), 189(13.5), 155(13.8). Found: C, 52.35; H, 4.16; Cl, 19.15; N, 11.39. C$_{16}$H$_{14}$ClN$_3$O$_3$HCl requires: C, 52.32; H, 4.09; Cl, 19.07; N, 11.44%.

4-(2',4'-Dihydroxyl-1',3'-diazine-5')-amino-6,7-dime-thoxyquinazoline (HI-P215) (Yield 89.23%, m.p.>300.0° C) $^1$H NMR(DMSO-d$_6$): δ 8.59(s, 1H, 2-H), 7.89(s, 1H, 5-H), 7.60 (d, 1H, 6'-H), 7.09 (s, 1H, 8-H), 3.78(s, 3H, —OCH$_3$), 3.76(s, 3H, —OCH$_3$). UV(MeOH): 222.0, 246.0, 331.0 nm. IR(KBr)$\upsilon_{max}$: 3446, 3212, 3057, 1750, 1682, 1620, 1590, 1511, 1420, 1265 cm$^{-1}$. GC/MS m/z: 315(M$^-$.57.52), 206(46.50), 191(18.21), 127(100.00).

4-(3'-Hydroxymethylphenyl)-amino-6,7-dimethoxyquina-zoline(HI-P259) Yield 74.28%; m.p. 230.0–232.0° C. $^1$H NMR(DMSO-d$_6$): δ 11.29(s, 1H, —NH), 8.83(s, 1H, 2-H)I, 8.28(s, 1H, 5-H), 7.61–7.25(m, 4H, 2',4',5',6'-H), 7.36(s, 1H, 8H)O, 4.57(s, 2H, —CH$_2$OH), 4.02(s, 3H, —OCH$_3$), 4.00(s, 3H, —OC$_3$). UV(MeOH): 207.0, 224.0, 251.0, 334.0 nm. IR(KBr)$\upsilon_{max}$: 3500, 3029, 1639, 1589, 1514, 1456, 1284 cm$^{-1}$. GC/MS m/z: 281(M-+-CH$_2$OH, 54.00), 280(M$^-$CH2OH, 100.00). Found: C, 58.68; H;, 5.30; N, 12.02. C$_{16}$H$_{15}$N$_3$O$_2$. HCl requires: C, 58.79; H, 5.19; N, 12.10%.

4-[4'-(2''-Hydroxyethylphenyl)]-amino-6,7-dimethoxyqui-nazoline (HI-P265) Yield 92.30%; m.p. 235.0–240.0° C. $^1$H NMR(DMSO-d$_6$): δ 11.44(s, 1H, —NH), 8.79(s, 1H, 2-H), 8.34(s, 1H, 5-h)I, 7.56(d, 2H, J=8.1Hz, 2',6'-H), 7.34(d, 2H, J-8.1Hz, 3',5'-H), 7.31(s, 1H, 8H), 4.00(s, 3H, —OCH$_3$), 3.99(s, 3H, —OCH$_3$), 3.64(t, 2H, J=6.9Hz, 1''-H)I, 2.77(t, 2H, J=6.9Hz, 2''-H). UV(MeOH): 204.0, 226.0, 251.0, 335.0 m. IR(KBr)$\upsilon_{max}$: 3361, 3015, 27o6o7, 1628, 1581, 1514, 1432, 1282 cm$^{-1}$. GC/MS m/z: 281(17.00), 253(10.00), 207(100.00).

4-[2'-(2''-Hydroxylethylphenyl)]-amino-6,7-dimethoxyqui-nazoline(HI P266) Yield 87.69%; m.p/ 228.0–230.0° C. $^1$H NMR-DMSO-d$_6$): δ 11.32(s, 1H, —NH), 8.74(s, 1H, 2'-H), 8.13(s, 1H, 5-H), 7.46–7.34(m, 4H, 3',4',5,6'-H), 7.32(s, 1H, 8H), 4.00(s, 3H, —OCH$_3$), 3.99(s, eH, —OCH$_3$), 3.58(t, 2H, J-7.2Hz, 1''-H), 2.75(t, 2H, J=7.2Hz, 2''-H). UV(MeOH): 210.0, 226.0, 249.0, 332.0 nm. IR(KBr)$\upsilon_{max}$: 3366, 3226, 3056, 2917o, 2685, 21638, 1571, 1514, 1467, 1277 cm$^{-1}$. GC/MS m/z: 281(20.00), 253(9.00), 207(100.00).

4-(1'-Naphthol-4')-amino-6,7-edimethoxyquinazoline(HI-P274) Yield 79.26; m.p. 205.0–208.0° C. $^1$H NMR-DMSO-d$_6$): δ 11.64(s, 1H, —NH), 10.61(s, 1H, —OH), 8.59(s, 1H, 2-h), 8.41(s, 1H, 5-H), 8.22–6.98(m, 5H, 3',5',6',7,8'-H), 7.40(s, 1H, 8H), 4.00(s, 3H, —OCH$_3$), 3.99(s, 3H, —OCH$_3$). UV(MeOH): 208.0, 215.0, 225.0, 240.0, 330.0 nm. IR(KBr)$\upsilon_{max}$: 3438, 3211, 3061, 2932, 2834, 1633, 1576, 1509, 1437, 1380, 1276, 1215 cm$^{-1}$. GC/MS m/z: 281(51.00), 253(22.00), 207(88.00). Found: C, 62.26; H, 4.87; N, 10.77. C$_{20}$H$_{17}$N$_3$O$_3$.HCl requires: C, 62.66; H, 4.70; N, 10.96%.

4-(2'-Naphthol-1')-amino-6,7-dimethoxyquinazoline(HI-P275) Yield 83.17%; m.p 218.0–220.0° C. $^1$H NMR(DMSO-d$_6$): δ 11.33(s, 1H, —NH), 10.22(s, 1H, —OH), 8.62(s, 1H, 2-H), 8.40(s, 1H, 5-H), 7.98–7.31(m, 6H, 3',4',5',6',7''8'-H), 7.41(s, 1H, 8H), 4.02(s, 3H, OCH$_2$), 4.00(s, 3H, —OCH$_3$),. UV(MeOH): 206.0, 210, 219.0, 225.0, 230.0, 340.0 nm. IR(KBr)$\upsilon_{max}$: 3391, 3165, 3051, 2938, 2840, 1628, 1576, 1504, 1437, 1281, 1215 cm$^{-1}$. GC/MS m/z: 348(M$^-$+1, 7.00), 347 (M$^-$, 100.00), 346(M$^-$1.22.00), 331(15.00), 330(12.00), 281(23.00), 253(12.00), 207(49.00). Found: C, 62.91; H, 4.76; N, 10.75. C$_{20}$H$_1$N$_3$O$_3$.HCl requires: C, 62.66; H, 4,70; N, 10.96%.

4-[3'-(1''-Hydroxyethyl)]-amino-6,7-dimethoxyquinazoline (HI-P276) Yield 79.21%; m.p. 215.0–218.0° C. $^1$H NMR(DMSO-d$_6$): δ 11.40(s, 1H, —NH), 8.81(s, 1H, 20H), 8.31(s, 1H, 5-H)O, 7.60–7.26(m, 4H, 2',4',5,6'-H), 7.41(s, 1H, 8H), 4.65(q, 1H, J=6.6Hz, —CH(OH)CH$_3$), 4.00(s, 3H, —OCH$_3$), 3.98(s, 3H, —OCH$_3$), 1.350(d, 3H, J=6.6Hz, —CH$_3$). UV9MeOH): 204.0, 216.0, 220.0, 224.0, 250.0, 348.0 nm. IR(KBr)$\upsilon_{max}$: 3407, 3030, 2977, 2840, 1643, 1591 1514, 1463, 1370, 1282, 1230 cm$^{-1}$. GC/MS m/z: 325(M$^-$+1, 67.00), 324(M$^-$, 100.00), 323(M$^-$1.22.00), 308(17.00), 307(56.00), 306(21.00), 281(2.00), 280(8.00), 264(6.00).

4-(4'-Hydroxy-3',5'-diphenylphenyl)-amino-6,7-dime-hoxyquinazoline (HI-P277) Yield 76.11%; m.p. 255.0–257.0° C. $^1$H NMR__DMSO-d$_6$): δ 11.50(s, 1H, —NH), 8.80(d, d, 2H, 2',6'-H), 8.58(s, 1H, 5-H), 7.60–7.30(m, 10H, 3', 5', Ph-H), 7.39(s, 1H, 8H), 4.00(s, 3H, —OCH$_3$), 3.97(s, 3H, —OCH$_3$), 1.350(d, eH, J=6.6Hz, —CH$_3$). UV(MeOH): 210.0, 214.0, 229.0, 239.0, 345.0, 248.0, 352.0 nm. IR(KBr)$\upsilon_{max}$: 3520, 3218, 3023, 2935, 1630, 1562, 1518, 1457, 1281, 1234 cm$^{-1}$. GC/MS m/z 281(35.00), 267(6.00), 253(10.00), 207(100.00).

-continued 4-(4'-Hydroxyl-2'-chlorophenyl)-amino-6,7-dimethoxy-quinazoline(HI-P2878) Yield 81.44%; m.p. 245.0–247.0° C. $^1$H NMR(DMSO-d$_6$): δ 11.39(s, 1H, —NH)O, 10.30(s, 1H, —OH); 8.75(s, 1H, 2-H), 8.24(s, 1H, 5-H), 7.38–6.85(m, 3H, 3',5',6'-H), 7.37(s, 1H, 8H), 3.98(s, 3H, —OCH$_3$), 3.96(s, H3, —OCH). UV(MeOH): 222.0, 234.0, 239.0, 245.0, 254.0 348.0 nm. IR(KBr)υ$_{max}$: 3448, 3242, 3144, 3025, 2917, 2834, 1638, 1591, 1514, 1437, 1365, 1277, 1209 cm$^{-1}$. GC/MS m/z: 332(M$^-$+1, 5.00), 331(M$^-$, 17.00), 330(M$^-$–1, 5.00), 297(17.00), 296(100.00), 281(18.00), 280o(29.00), 253 (9.00).

4-(2'-Hydroxy-naphthyl-3')-amino-6,7-dimethoxyquinazolin(HI-P292) Yield 87.41%; m.p. 277.0–279.0° C. $^1$H NMR(DMSO-d$_6$): δ 11.38(s, 1H, —NH)O, 10.35(s, 1H, —OH), 8.73(s, 1H, 2-H), 8.25(s, 1H, 5-H), 7.93–7.30(m, 6H, 1', 4', 5', 6', 7', 8'-H), 7.37(s, 1H, 8H)O, 4.00(s, 6H, —OCH$_3$). UV(MeOH): 204.0, 221.0, 224.0, 230.0, 256.0, 344.0 nm. IR(KBr)υ$_{max}$: 3479, 3386, 3036, 2901, 1632, 1581, 1504, 1437, 1281 cm$^{-1}$. GC/MS m/z: 281(41.00), 253(11.00), 207(100.00). Found: C, 62.87; H;, 4.83; N, 100.78. C$_{20}$H$_1$N$_3$O$_3$. HCl requires: C, 62.66; H, 4.70, N, 10.96%.

4-(1'-Hydroxy-naphthyl-5')-amino-6,7-dimethoxyquina-zoline(HI-P293) Yield 87.21%; m.p. 204.0–205.0° C. $^1$H NMR(DMSO-d$_6$): δ 11.73(s, 1H, —NH) 10.43(s, 1H, —OH), 8.65(s, 1H, 2-H, 8.38(s, 1H, 5-H), 8.21–6.95(m, 6H, 2', 3', 4', 6', 7', 8'-H), 7.33(s, 1H, 8H)O, 4.00(s, 6H, —OCH$_3$). UV9MeOH): 204.0, 214.0, 224.0, 229.0, 235.0 348 nm. IR(KBr)υ$_{max}$: 3449, 3335, 3102, 2927o, 1633, 1571, 1509, 1437, 1287 cm$^{-1}$. Found: C, 62.23; H, 4.96; N, 10.89. C$_{20}$H$_{17}$N$_3$O$_3$.HCl requires. C, 62.66; H, 4.70; N, 10.96%.

4-(4'-Hydroxy-3.5-diiodophenyl)-amino-6,7-dimethoxy-quinazoline(HI-P294) Yield 77.47 &; m.p. 259.0–260.0° C. $^1$H NMR(DMSO-d$_6$): δ 11.13(s, 1H, NH), 9.73(s, 1H, —OH), 8.87(s, 1H, 2-H), 8.16(s, 1H, 5-H), 8.09(s, 2H, 1', 6'-H), 7.28(s, 1H, 8H), 3.98(s, 6H, —OCH$_3$). UV(MeOH)λ$_{max}$:. 217.0, 227.0, 252.00 nm. IR(KBrυ$_{max}$: 3457, 3201, 2934, 2832, 2566, 1629, 1562, 1521, 1439, 1275, 1075 cm$^{-1}$. GC/MS m/z: GC/MS m/z 422(M$^-$I.33.53), 405(7.50), 281(86.67), 221(51.80), 207(91.30). Found: C, 32.60; H, 2.50; N, 6.92. C$_{16}$H$_{13}$I$_2$N$_3$O$_3$.HCl requires: C. 32/82.'J. 2.39; N, 7.18%.

4-(4'-Hydroxy-3'-iodophenyl)-amino-6,7-dimethoxyquinazoline(HI-P299) Yield 71.59%; m.p. 248.0–250.0° C. $^1$H NMR(DMSO-d$_6$): δ 11.32(d, 1H, NHO), 10.62(s, 1H, —OH, 8.79(s, 1H, 2-H), 8.26(s, 1H, 5-H), 7.98 – 6.98(m, 3H, 2',3',6'-H), 7.32(s, 1H, 8H), 3.98(s, 3H, —OCH$_3$), 3.97(s, 3H, —OCH$_3$). UV(MeOH)λ$_{max}$(ε):. 217.0, 227.0, 252.0 nm. IR(KBr)υ$_{max}$: 3411, 2975, 2730, 2366, 1634, 1573, 1501, 1429, 1229, 1075 cm$^{-1}$. GC/MS m/z: 406(M$^-$1.3.33), 405(M$^-$2, 7.50), 281(M$^+$– 1-I, 26.67), 253(11.80), 207(100.00). Found: C, 41.96; H, 3.40; N, 8.98. C$_{16}$H$_{14}$IN$_3$O$_3$.HCl requires: C, 41.83; H, 3.26; N, 9.15%.

TABLE 5

Fluoroquinazoline Derivatives

| (HI-P352) No | R | (HI-P353) Formular | MW |
|---|---|---|---|
| HI-P144 | 2-F, 3-F, 5-F, 6-F, 4-Br | C$_{16}$H$_{10}$BrF$_4$N$_3$O$_2$ | 432 |
| HI-P214 | 2-F, 4-Br | C$_{16}$H$_{13}$BrFN$_3$O$_2$ | 378 |
| HI-P218 | 3-CF$_3$ | C$_{17}$H$_{14}$F$_3$N$_3$O$_2$ | 349 |
| HI-P219 | 4-OCF$_3$ | C$_{17}$H$_{14}$F$_3$N$_3$O$_3$ | 365 |
| HI-P221 | 4-F | C$_{16}$H$_{14}$FN$_3$O$_2$ | 299 |
| HI-P223 | 4-CF$_3$ | C$_{17}$H$_{14}$F$_3$N$_3$O$_2$ | 349 |
| HI-P224 | 3-F | C$_{16}$H$_{14}$FN$_3$O$_2$ | 299 |
| HI-P228 | 2-CF$_3$ | C$_{17}$H$_{14}$F$_3$N$_3$O$_2$ | 349 |
| HI-P232 | 4-SO$_2$F | C$_{16}$H$_{14}$FN$_3$O$_4$S | 363 |
| HI-P264 | 2-F | C$_{16}$H$_{14}$FN$_3$O$_2$ | 299 |
| HI-P352 | * | C$_{25}$H$_{20}$F$_6$N$_4$O$_2$ | 522 |
| HI-P353 | * | C$_{25}$H$_{20}$F$_6$N$_4$O$_2$ | 522 |
| HI-P364 | 3-OCF$_3$ | C$_{17}$H$_{14}$F$_3$N$_3$O$_3$ | 365 |
| HI-P365 | 2-OCF$_3$ | C$_{17}$H$_{14}$F$_3$N$_3$O$_3$ | 365 |
| HI-P366 | 3-CF$_3$, 5-CF$_3$, | C$_{18}$H$_{13}$F$_6$N$_3$O$_2$ | 417 |
| HI-P367 | 2-CF$_3$, 5-CF$_3$, | C$_{18}$H$_{13}$F$_6$N$_3$O$_2$ | 417 |
| HI-P369 | 3-F, 4-OH | C$_{16}$H$_{14}$FN$_3$O$_3$ | 315 |
| HI-P408 | 3-F, 5-F, 4-OH | C$_{16}$H$_{13}$F$_2$N$_3$O$_3$ | 333 |

HI-P352

HI-P353

Example 6

Fluorine Substituted Quinazoline Compounds

Fluorine substituted quinazoline derivatives were synthesized and characterized as discussed above for Example 1. The structures and physical data are shown below:

| No | Name | Structure | Formula | MW |
|----|------|-----------|---------|-----|
| 1 | P-144 | 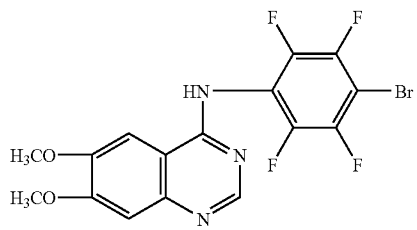 | $C_{16}H_{10}BrF_4N_3O_2$ | 432 |
| 2 | P-214 | 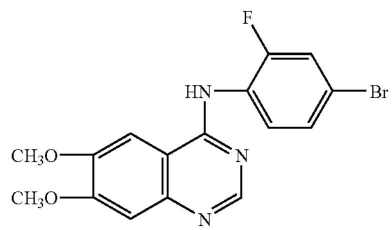 | $C_{16}H_{13}BrFN_3O_2$ | 378 |
| 3 | P-218 | 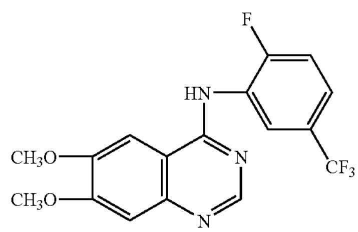 | $C_{17}H_{13}F_4N_3O_2$ | 367 |
| 4 | P-219 | 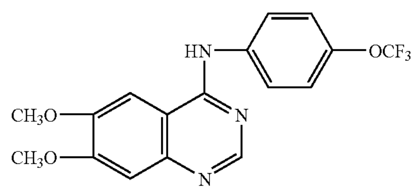 | $C_{16}H_{14}F_3N_3O_3$ | 365 |
| 5 | P-221 | 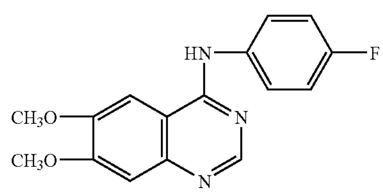 | $C_{16}H_{14}FN_3O_2$ | 299 |
| 6 | P-223 | 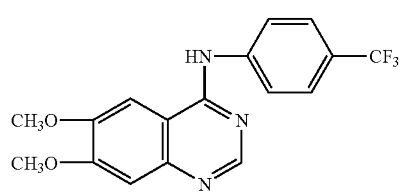 | $C_{17}H_{14}F_3N_3O_2$ | 349 |
| 7 | P-224 | 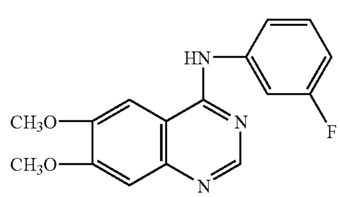 | $C_{16}H_{14}FN_3O_2$ | 299 |

-continued

| No | Name | Structure | Formula | MW |
|---|---|---|---|---|
| 8 | P-228 | 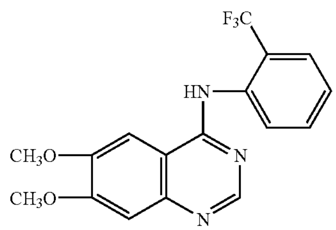 | $C_{17}H_{14}F_3N_3O_2$ | 349 |
| 9 | P-232 | 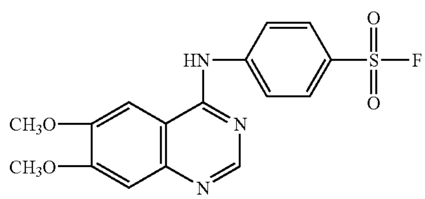 | $C_{16}H_{14}F_2SN_3O_4$ | 363 |
| 10 | P-264 | 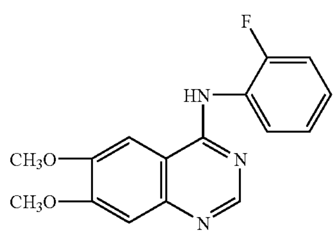 | $C_{16}H_{14}FN_3O_2$ | 299 |
| 11 | P-352 | 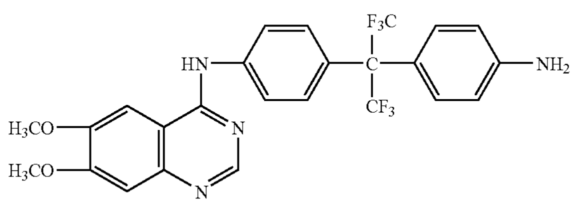 | $C_{25}H_{20}F_6N_4O_2$ | 522 |
| 12 | P-353 | 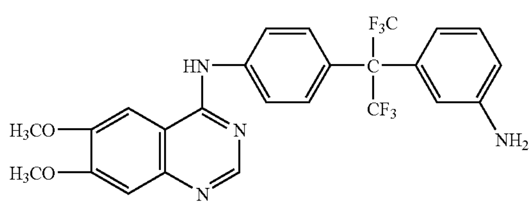 | $C_{25}H_{20}F_6N_4O_2$ | 522 |
| 13 | P-364 | 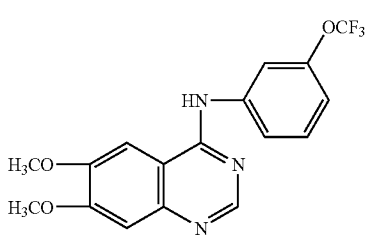 | $C_{17}H_{14}F_3N_3O_3$ | 365 |
| 14 | P-365 | 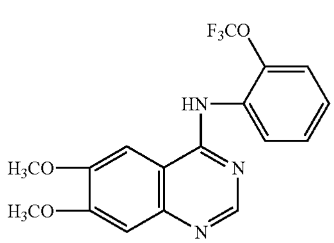 | $C_{17}H_{14}F_3N_3O_3$ | 365 |

-continued

| No | Name | Structure | Formula | MW |
|---|---|---|---|---|
| 15 | P-366 | 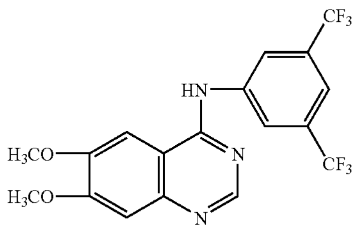 | $C_{18}H_{13}F_6N_3O_2$ | 417 |
| 16 | P-367 | 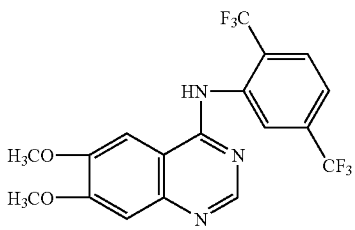 | $C_{18}H_{13}F_6N_3O_2$ | 417 |
| 17 | P-369 | 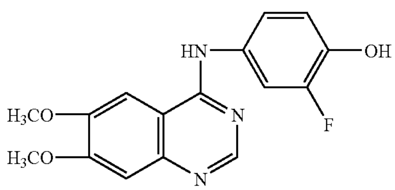 | $C_{16}H_{14}FN_3O_3$ | 315 |
| 18 | P-408 | 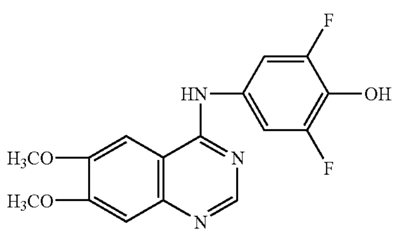 | $C_{16}H_{13}F_2N_3O_3$ | 333 |

4-(2',3',5',6'-Terrafluoro-4'-bromophenyl)-amino-6,7-dime-thoxyquinazoline (HI-P144) The yield 78.24%: m.p. 180.0–182.0 0° C. $^1$H NMR (DMSO-d_): δ 7.78(s. 1H. 2-H), 7.53(s. 1H, 5-H), 6.79(s. 1H, 8-H), 3.81(s. 3H, —OCH$_3$), 3.3.79(s. 3H, —OCH$_3$). Found: C, 41.12; H, 2.41: N, 9.89, $C_{10}H_{10}BrF_{-}N_3O_2$.HCl. requires: C, 41.11; H, 2.36; N, 9.93%.

4-(2'-Fluoro-4'-bromophenyl)-amino-6,7-dimethoxyquina-zoline (HI-P214) The yield 77.21%; m.p. 247.0–252.0 0° C. $^1$H NMR(DMSO-d$_6$) : δ 8.57(s. 1H. 2-H), 7.91(s. 1H, 5-H), 7.57(d. 1H, 3'-H), 7.34(m, 2H, 5',6'-H), 7.07(s, 1H, 8'-H), 3.78(s, 3H, —OCH$_3$), 3.77(s, 3H, —OCH$_3$). UV(MeOH):.204.0, 215.0, 250.0, 330.0 nm. IR(KBr)υ$_{max}$: 3431, 2629, 1633, 1580, 1511, 1420, 1278 cm$^{-1}$. GC/MS m/z 379(M$^+$+1, 34.39), 378(M$^-$, 31.33). 377(M$^-$–1, 39.08), 360(62.05), 359(31.58), 358(62.57), 357(19.81), 299(19.31), 298(100.00), 282(17.88), 240(28.76).

4-(3'-Trifluoromethylphenyl)-amino-6,7-dimethoxyquinazo-line (HI-P218) The yield 85.61%: m.p. 242.0–245.0 0° C. $^1$H NMR(DMSO-d$_6$): δ 11.09(s. 1H. —NH). 8.67(s. 1H. 2-H), 8.03(s, 1H, 5-H), 7.92–7.43(m, 4H, 2'4'5',6'-H), 7.10(s, 1H, 8-H). 3.81(s, 3H, —OCH$_3$), 3.79(s, 3H, —OCH$_3$). UV(MeOH):. 206.0, 276.0, 349.0 nm. IR υ$_{max}$ (KBr): 3372, 3257, 2935, 1626, 1512, 1380, 1225 cm$^{-1}$. GC/MS m/z 350(M$^+$+1, 10.5), 249(M$^-$, 85.5). 173(M$^-$–1, 100.0), 332(10.5), 290(8.8).

4-(4'-Trifluoromethoxylphenyl)-amino-6,7-dimethoxyqui-nazoline (HI-P219) The yield 83.14%; m.p. 228.0–230.0 0° C. $^1$H NMR(DMSO-d$_6$): δ 11.39(s, 1H, —HN), 8.63(s, 1H, 2-H), 8.18(s, 1H, 5-H), 7.63(t, 2H, 3',5'-H), 7.27(t, 2H, 2', 6'-H), 7.15(s, 1H, 8-H), 3.81(s, 3H, —OCH$_3$), 3.78(s, 3H, —OCH$_3$). UV(MeOH):. 209.0, 216.0, 251.0, 332.0 nm. IR(KBr)υ$_{max}$: 3207, 2839, 2762, 1633, 1508, 1480, 1276 cm$^{-1}$. GC/MS m/z 366(M$^+$+1, 12.50). 365 (M$^-$, 75.00), 364(M$^-$–1, 100.00), 348(17.50), 319(19), 306(8.00), 207(15.00).

4-(4'-Fluorophenyl)-amino-6,7-dimethoxyquinazoline(HI-P221) The yield 84.25%:. $^1$H NMR(DMSO-d$_6$): δ 11.19 (s, 1H, —HN), 8.60(s, 1H, 2-H), 8.08(s, 1H, 5-H)). 7.50(t, 2H, 3'-H), 7.13(s, 1H, 8-H), 7.12(t, 2H, 2', 6'-H), 3.79 (s, 3H, —OCH$_3$), 3.78(s, 3H, —OCH$_3$). UV(MeOH):. 225.0, 251.0, 333.0 nm. IR(KBr)υ$_{max}$: 3205, 3007, 2837, 1633, 1580, 1508, 1470, 1220 cm$^{-1}$. GC/MS m/z 300(M$^+$+1, 10.76), 299(m$^-$, 76.92), 398(M$^-$–1, 100.00), 282 (20.00).. 253(13.08), 207(3.80). Found: C, 57.17; H, 4.37; N, 12.47, $C_{16}H_{14}FN_3O_2$.HCl requires C. 57, 31: H, 4.48; N, 12.54%.

4-(4'-Trifluoromethylphenyl)-amino-6,7-dimethoxyquinazoline (HI-P223) The yield 91.70%: m.p. 243.0–245.0 0° C. $^1$H NMR(DMSO-d$_6$): δ 11.47(s, 1H, —NH), 8.67(s, 1H, 2-H), 8.23(s, 1H, 5-H). 7.79(d, 2H, J = 8.4Hz, 3'5'-H). 7.61(d, 2H, J = 8.4Hz, 2'6'-H), 7.17(s, 1H, 8-H), 3.82(s, 3H, —OCH$_3$), 3.78(s, 3H, —OCH$_3$). GC/MS m/z 350(M$^+$+1, 11.00). 349(M$^-$, 65.00), 348(M$^-$–1, 100.00), 332(18.50), 303(10.00), 207(18.50). Found: C, 53.01; H, 3.94; N, 10.88. $C_1$—$NH_{14}F_3N_3O_2HCl$ requires C. 52.98; H, 3.90: N, 10.91%.

-continued

| No | Name | Structure | Formula | MW |
|---|---|---|---|---|

4-(4'-Flurophenyl)-amino-6,7-dimethoxyquinazoline(HI-P224) The yield 88.69%; m.p. 254.0–255.0 0° C. $^1$H NMr (DMSO-d$_6$): δ 11.16(s, 1H, —HN), 8.67(s, 1H, 2-H), 8.09(s, 1H, 5-H), 7.13(s, 1H, 8-H), 7.51–6/94(m, 4H, 2',3', 5',6'-H)O, 3.80(s, 3H, —OCH$_3$), 3.79(s, 3H, —OCH$_3$). UV(MeOH): 206.0, 226.0, 251.0, 333.0, 343 nm.. IR(KBr)υ$_{max}$: 3437, 3211, 2619, 1637, 1580, 1500, 1448, 1281 cm$^{-1}$. GC/MS m/z (300(M$^+$+1, 8.00), 299(M$^-$, 68.00), 398(M$^-$1, 100.00), 282(21.60), 253(25.00), 207(80.00),. Found: C, 57.25; H, 4.58; N, 12.42. C$_{16}$H$_{14}$FN$_3$O$_2$.HCl requires C, 57.31; H, 4.48; N, 12.54%.

4-(2'-Trifluoromethylphenyl)-amino-6,7-dimethoxyquinazoline(HI-P228). The yield 83.57%; m.p. 242.0–245.0 0° C. $^1$H NMR(DMSO-d$_6$): δ 11.58(s, 1H, —HN), o8.76(s, 1H, 2-H), 8.25(s, 1H, 5-H), 7.95–7.62(m, 4H, 3', 4', 5', 6'-H), 7.38(s, 1H, 8-H), 4.01(s, 3H, —OCH$_3$), 3.00(s, 3H, —OCH$_3$). GC/MS m/z 350(M$^-$+1, 8.50), 349(M$^-$, 32.00), 348(M$^+$-1, 31.50), 328(1850), 207(5.0)I, 280(M$^+$—CF$_3$, 100.00), 264(18.50), 207(32.50). Found: C, 52.71; H, 4.26; N, 10.91%.

4-[4'-benzenesulfanilylfluoride]-amino-6,7-dimethoxyquinazoline (HI-P232) Yield 84.02%; m.p. 228.0–230.0 0° C. $^1$H NMR(DMSO-d$_6$): δ 11.62(s, 1H, —HN), 8.78(s, 1H, 2-H), 8.29(s, 1H, 5-H), 8.12–8.02(m, 4H, 2'',3'',5'',6''-H), 7.21(s, 1H, 8-H), 3.86(s, 3H, —OCH$_3$), 3.81(s, 3H, —OCH$_3$). UV(MeOH): 208.0, 215.0, 253.0, 278.0, 338.0 nm.. IR(KBr)υ$_{max}$: 3440, 3277, 2571, 1635, 1580, 1516, 1435, 1209 cm$^{-1}$. GC/MS m/z: 281(43.00), 253(12.00), 207(100.00). Found: C, 48.13; H, 3.73; N, 10.53. C$_{16}$H$_{14}$FN$_3$O$_4$S. HCl requires: C, 48.12; H, 3.76; N, 10.53%.

4-(2'-Fluorophenyl)-amino-6,7-dimethoxyquinazoline(HI-P264) Yield 73.58%; m.p. 233.0–235.0 0° C. $^1$H NMR (DMSO-d$_6$): δ 11.69(d, 1H, —NH), 8.82(s, 1H, 2-H), 8.37(s, 1H, k 50H), 7.59–7.32(m, 4H 3', 4'5', 6'-H), 7.41(s, 1H, 8H)O, 4.02(s, 3H, —OCH$_3$), 4.01(s, 3H, —OCH$_3$). UV(MeOH): 204.0, 226.0, 248.0, 330.0 nm. IR(KBrυ$_{max}$: 3454, 3032, 2638, 1630, 1589, 1514, 1430, 1291 cm$^{-1}$. GC/MS m/z 300(M$^+$=1, 7.00), 299(M$^-$, 38.00), 298(M$^-$1, 22.00), 280(M$^-$F, 100.00), 264(15.00), 207(35.00). Found: C, 57.12; H, 4.57; N, 12.45. C$_{16}$H$_{14}$FN$_3$O$_2$.HCl requires: C, 57.31; H, 4.48; N, 12.54%.

4-{4'-[2''-(4'''-Aminophenyl)-hexafluoropropyl]phenyl}amino-6,7-dimethoxyquinazoline(HI-P352) Yield, 80.41%, m.p. 280.0–282.0 0° C. $^1$H NMR(DMSO-d$_6$): δ 11.87(s, 1H, —NH), 8.91(s, 1H, 2-H)I, 8.55–7.18(m, 10H, 5, 8, 2', 3', 5', 6', 2''', 3''', 5''', 6'''-H), 4.05(s, 3H, —OCH$_3$), 4.00(s, 3H, —OCH$_3$). $^{19}$F NMR(DMSO-d$_6$): 128.76. Found: C, 50.33; H, 3.87; N, 9.57. C$_{25}$H$_{20}$F$_6$N$_4$O$_2$.2HCl requires: C, 50.50; H, 3.70; N, 9.42%

4-{3'-[2''-(3'''-Aminophenyl)-hexafluoropropyl]phenyl}-amino-6,7-dimethoxyquinazoline(HI-P353) Yield, 83.11%,. m.p. 292.0–284.0 0° C. $^1$H NMR(DMSO-d$_6$): δ 11.68(s, 1H, —NH), 8.81(s, 1H, 2-H), 8.44–7.09(m, 10H, 5, 8, 2', 4', 5', 6', 2''', 4''', 5''', 6'''-H), 4.00(s, 3H, —OCH$_3$), 3.97(s, 3H, —OCH$_3$). $^{19}$F NMR(DMSO-d$_6$): 129.21. Found: C, 53.96: H, 3.93; N, 9.77. C$_{25}$H$_{20}$F$_6$N$_4$O$_2$.HCl requires: C. 53.76: H, 3.76: N, 10.03%

4-(3'-Trifluoromethoxylphenyl)-amino-6,7-dimethoxyquinazoline (HI-P364) Yield. 83.25%. m.p. 233.0–235.0 0° C. $^1$H NMR(DMSO-d$_6$): δ 11.65(s, 1H, —NH), 8.88(s, 1H, 2-H), 8.41(s, 1H, 5-H), 7.86–7.29(m, 4H, 2', 4', 5', 6'-H). 7.36(s, 1H, 8-H), 4.02(s, 3H, —OCH$_3$). 3.98(s, 3H, —OCH$_3$). $^{19}$F NMR(DMSO-d$_6$): 135.37. GC/MS m/z: 366(M$^+$+1, 11.0), 365(M$^+$, 67.0), 364(M$^+$-1, 100.0). Found: C, 50.93; H, 3.75; N, 10.61. C$_{17}$H$_{14}$F$_3$N$_3$O$_3$.HCl requires: C, 50.97; H, 3.74; N, 10.47%.

4-(2'-Trifluoromethoxylphenyl)-amino-6,7-dimethoxyquinazoline (HI-P365) Yield. 77.85%. m.p. 235.0–237.0 0° C. $^1$H NMR(DMSO-d$_6$): δ 11.68(s, 1H, —NH), 8.80(s, 1H, 2-H), 8.32(s, 1H, 5-H), 7.64–7.53(m, 4H, 3', 4', 5', 6'-H). 7.40(s, 1H, 8-H), 3.99(s, 6H, —OCH$_3$). $^{19}$F NMR(DMSO-d$_6$): 135.71. GC/MS m/z: 366(M$^-$+1, 2.0), 365 (M$^+$, 15.0), 364(M$^+$-1, 4.0), 281(21.0), 280(M$^-$—OCF$_3$ 100). Found: C, 50.83; H, 3.79; N, 10.52. C$_1$_H$_{14}$F$_3$N$_3$O$_3$.HCl requires: C, 50.87; H, 3.74; N, 10.47%.

4-(3',5'-Ditrifluoromethylphenyl)-amno-6,7-dimethoxyquinazoline (HI-P366) Yield. 82.88% m.p. 270.0–272.0 0° C. $^1$H NMR(DMSO-d$_6$): δ 11.87(s, 1H, —NH), 8.97(s, 1H, 2-H), 8.60)s, 2H, 2', 6'-H), 8.43(s, 1H, 5-H), 7.98(s, 1H, 4'-H), 7.35(s, 1H, 8-H), 4.03(s, 3H, —OCH$_3$), 3.99(s, 3H, —OCH$_3$). $^{19}$F NMR(DMSO-d$_6$): XX GC/MS m/z: 418(M$^-$+1, 19.0), 417(M$^-$, 100.0), 416(M$^-$-1, 73.0), 398(M$^-$—F, 16.0), 398(M$^-$—F, 16.0), 348(M$^-$—CF$_3$, 16.0). Found: C, 47.78; H, 3.20; N, 9.26. C$_{18}$H$_{13}$F$_6$N$_3$O$_2$.HCl requires: C, 47.68; H, 3.09; N, 9.27%.

4-(4'-Hydroxyl-3'-fluorophenyl)-amino-6,7-dimethoxyquinazoline (HI-P369) Yield. 84.28%. m.p. 268.0–270.0 0° C. $^1$H NMR(DMSO-d$_6$: δ 11.36(s, 1H, —NH), 10.13(s, 1H, —OH), 8.80(s, 1H, 2-H), 8.30(s, 1H, 5-H), 7.60–7.02 (m, 3H, 2', 5', 6'-H), 7.31(s, 1H, 8-H), 3.99(s, 3H, —OCH$_3$), 3.97(s, 3H, —OCH$_3$). $^{19}$F NMR(DMSO-d$_6$): δ 57.38. Found: C, 54.90: H, 4.28; N, 11.91. C$_{16}$H$_{14}$FN$_3$O$_3$.HCl requires C, 54.70; H, 4.27; N, 11.97%.

4-(4'-Hydroxyl-3',5'-difluorophenyl)-amino6,7-dimethoxy-quinazoline (HI-P408) Yield. 83.15%, m.p.228.0–230.0 0° C. $^1$H NMR(DMSO-d$_6$): δ 11.46(s, 1H, —NH), 10.39(s, 1H, 2-H), 8.36(s, 1H, 5-H), 7.56, 7.54(s, s, 2H, 2', 6'-H), 7.33(s, 1H, 8-H), 4.00)s, 3H, —OCH$_3$), 3.98(s, 3H, —OCH$_3$). $^{19}$F NMR-DMSO-d$_6$ : δ 60.25, 60.22. Found: C, 52.04; H, 4.17; N, 11.10. C$_{16}$H$_{13}$F$_2$N$_3$O$_3$.HCl. requires C, 52.03; H, 3.79; N, 11.38%.

Example 7

Anti-Tumor Activities of Specific Quinazoline Compounds

The cytotoxicity of the substituted quinazoline derivative compounds against a variety of human tumor cells was evaluated. The relative importance of particular substituent groups on the compounds was also studied. The substituted quinazoline derivative compounds, prepared as described above, were tested, along with DMSO as a control.

Cytotoxicity Assay

The cytotoxicity assay of various compounds against human tumor cell lines was performed using the MTT (3-[4,5-dimethylthiazol-2-yl]-2,5-diphenyl tetrazolium bromide) assay (Boehringer Mannheim Corp., Indianapolis, Ind.). Briefly, exponentially growing tumor cells were seeded into a 96-well plate at a density of 2.5×10$^4$ cells/well and incubated for 36 hours at 37° C. prior to drug exposure. On the day of treatment, culture medium was carefully aspirated from the wells and replaced with fresh medium containing the quinazoline compounds at concentrations ranging from 0.1 to 250 μM. Triplicate wells were used for each treatment.

Human cell lines were obtained from American Type Culture Collection (Rockville, Md.) and maintained as a continuous cell line in Dulbecco's modified Eagles' medium supplemented with 10% fetal bovine serum and antibiotics. Cells used in this study include human leukemia cells (NALM-6 and MOLT-3), human breast cancer cells (BR20), human prostate cancer cells (PC3), and human brain tumor cells (U373).

The cells were incubated with the various compounds for 24–36 hours at 37° C. in a humidified 5% CO$_2$ atmosphere. To each well, 10 μl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10%

SDS in 0.01 M HCl. The absorbance of each well was measured in a microplate reader (Labsystems) at 540 nm and a reference wavelength of 690 nm. To translate the $OD_{540}$ values into the number of live cells in each well, the $OD_{540}$ values were compared to those on standard OD 540—versus—cell number curves generated for each cell line. The percent survival was calculated using the formula:

$$\% \text{ Survival} = \frac{\text{live cell number [test]}}{\text{live cell number [control]}} \times 100$$

The $IC_{50}$ values were calculated by non-linear regression analysis.

Detection of Apoptosis

The demonstration of apoptosis was performed by the in situ nick-end-labeling method using ApopTag in situ detection kit (Oncor, Gaithersburg, Md.) according to the manufacturer's recommendations. Exponentially growing cells were seeded in 6-well tissue culture plates at a density of $50 \times 10^4$ cells/well and cultured for 36 hours at 37° C. in a humidified 5% $CO_2$ atmosphere. The supernatant culture medium was carefully aspirated and replaced with fresh medium containing unconjugated EGF or EGF-P154 at a concentration of 10, 25, or 50 μg/ml. After a 36 hour incubation at 37° C. in a humidified 5% $CO_2$ incubator, the supernatants were carefully aspirated and the cells were treated for 1–2 minutes with 0.1% trypsin. The detached cells were collected into a 15 ml centrifuge tube, washed with medium and pelleted by centrifugation at 1000 rpm for 5 minutes. Cells were resuspended in 50 μl of PBS, transferred to poly-L-lysine coated coverslips and allowed to attach for 15 minutes. The cells were washed once with PBS and incubated with equilibration buffer for 10 minutes at room temperature.

After removal of the equilibration buffer, cells were incubated for 1 hour at 37° C. with the reaction mixture containing terminal deoxynucleotidyl transferase (TdT) and digoxigenin-11-UTP for labeling of exposed 3'-hydroxyl ends of fragmented nuclear DNA. The cells were washed with PBS and incubated with anti-digoxigenin antibody conjugated to FITC for 1 hour at room temperature to detect the incorporated dUTP. After washing the cells with PBS, the coverslips were mounted onto slides with Vectashield containing propidium iodide (Vector Labs, Burlingame, Calif.) and viewed with a confocal laser scanning microscope. Non-apoptotic cells do not incorporate significant amounts of dUTP due to lack of exposed 3-hydroxyl ends, and consequently have much less fluorescence than apoptotic cells which have an abundance of exposed 3'-hydroxyl ends. In control reactions, the TdT enzyme was omitted from the reaction mixture.

Results

The cytotoxicity results for each tested group of compounds is shown in Tables 1–5 below:

TABLE 1

Cytotoxic Activity of Bromo Substituted Quinazoline Compounds against Leukemic (NALM-6 & MOLT-3) and Breast Cancer (BT-20)

| Drug | NALM-6 IC50 (μM) | MOLT-3 IC50 (μM) | BT20 IC50 (μM) |
|---|---|---|---|
| HI-P79 | 142.1 | 194.9 | 201.5 |
| HI-P88 | >250 | >250 | >250 |
| HI-P97 | >250 | >250 | 26.1 |
| HI-P111 | 200.6 | >250 | >250 |
| HI-P154 | 12.5 | 9.1 | >250 |
| HI-P160 | 135.2 | 240.7 | 25.5 |
| HI-P164 | >250 | >250 | 39.2 |
| HI-P190 | >250 | >250 | >250 |
| HI-P210 | >250 | >250 | >250 |
| HI-P211 | >250 | >250 | >250 |
| HI-P212 | 52.7 | 54.5 | >250 |
| HI-P214 | >250 | >250 | >250 |
| HI-P222 | 34.0 | 48.3 | >250 |
| HI-P234 | >250 | >250 | >250 |
| HI-P241 | >250 | >250 | >250 |
| HI-P258 | >250 | >250 | >250 |
| HI-P260 | 32.4 | 51.3 | 82.1 |
| HI-P261 | 72.6 | 148.5 | 218.6 |
| HI-P262 | >250 | >250 | >250 |

TABLE 2

Cytotoxic Activity of Chloro Substituted Quinazoline Compounds against Leukemic (NALM-6 & MOLT-3) and Breast Cancer (BT-20)

| Drug | NALM-6 IC50 (μm) | MOLT-3 IC50 (μm) | BT20 IC50 (μm) |
|---|---|---|---|
| HI-P87 | 95.9 | >104.6 | >250 |
| HI-P93 | >250 | >250 | >250 |
| HI-P189 | >250 | >250 | >250 |
| HI-P197 | 39.3 | 68.0 | 136.9 |
| HI-P239 | 29.6 | 28.7 | 25.7 |
| HI-P246 | >250 | >250 | >250 |
| HI-P268 | 215.2 | 227.4 | 121.5 |
| HI-P269 | >250 | >250 | >250 |
| HI-P415 | 67.9 | >250 | 38.1 |

TABLE 3

Cytotoxic Activity of Iodide Substituted Quinazoline Compounds against Leukemic (NALM-6 & MOLT-3), Breast Cancer (BT-20) and Brain Tumor (U373) cells

| Drug | NALM-6 IC50 (μM) | MOLT-3 IC50 (μM) | BT20 IC50 (μM) | U373 IC50 (μM) |
|---|---|---|---|---|
| HI-P270 | >250 | 78.9 | >250 | >250 |
| HI-P271 | 6.1 | 9.6 | >250 | >250 |
| HI-P294 | >250 | >250 | >250 | >250 |
| HI-P299 | 15.4 | 60.1 | >250 | >250 |
| HI-P300 | 58.0 | 59.1 | 72.6 | 116.2 |

TABLE 4

Cytotoxic Activity of OH Substituted Quinazokline Compounds against Leukemic (NALM-6 & MOLT-3), Breast Cancer (BT-20) and Brain Tumor (U373) cells

| Drug | NALM-6 IC50 (µM) | MOLT-3 IC50 (µM) | BT20 IC50 (µM) | U373 IC50 (µM) |
|---|---|---|---|---|
| HI-P93 | >250 | >250 | >250 | >250 |
| HI-P97 | >250 | >250 | 26.1 | 161.2 |
| HI-P131 | 32.1 | 38.6 | >250 | >250 |
| HI-P154 | 12.5 | 9.1 | >250 | 167.4 |
| HI-P189 | >250 | >250 | >250 | >250 |
| HI-P190 | >250 | >250 | >250 | >250 |
| HI-P192 | >250 | >250 | >250 | >250 |
| HI-P197 | 68.5 | 63.8 | 71.5 | >250 |
| HI-P294 | >250 | >250 | >250 | >250 |
| HI-P299 | 66.3 | 51.2 | >250 | >250 |

TABLE 5

Cytotoxic activity of fluoro-substituted dimethoxy quinazolines on cancer cells.

| Compound | NALM-6 IC50 (µM) | MOLT-3 IC50 (µM) | U373 IC50 (µM) | BT20 IC50 (µM) | PC3 IC50 (µM) |
|---|---|---|---|---|---|
| HI-P144 | 28.1 ± 2.6 | 24.9 ± 3.7 | 49.5 ± 11.3 | 63.4 ± 5.5 | >250 |
| HI-P214 | >250 | >250 | >250 | >250 | >250 |
| HI-P218 | 37.0 ± 5.8 | 33.2 ± 3.3 | 29.9 ± 7.3 | 37.62 ± 5.2 | 126.1 ± 5.8 |
| HI-P219 | 22.3 ± 3.0 | 41.3 ± 4.4 | 83.6 ± 6.5 | 44.2 ± 10.9 | 58.3 ± 3.2 |
| HI-P221 | 100.5 ± 4.8 | 98.73 ± 3.8 | 28.8 ± 12.7 | 30.67 ± 7.9 | >250 |
| HI-P223 | 39.5 ± 8.0 | 40.8 ± 15.1 | 32.1 ± 3.9 | 27.56 ± 8.6 | >250 |
| HI-P224 | 20.15 ± 8.1 | 23.3 ± 7.7 | 22.4 ± 5.9 | 58.33 ± 5.8 | >250 |
| HI-P228 | 57.3 ± 24.8 | 237.1 ± 4.8 | >250 | >250 | >250 |
| HI-P232 | 41.4 ± 6.9 | 43.6 ± 2.3 | 207.7 ± 18.1 | 70.54 ± 8.2 | 88.9 ± 17.2 |
| HI-P264 | 47.0 ± 19.5 | 70.9 ± 17.3 | 53.3 ± 6.7 | 33.33 ± 7.5 | >250 |
| HI-P352 | 7.1 ± 1.8 | 21.8 ± 1.7 | 65.5 ± 11.2 | 50.3 ± 14.8 | 72.6 ± 2.5 |
| HI-P353 | 6.1 ± 1.4 | 17.4 ± 1.5 | 14.5 ± 7.6 | 14.1 ± 3.3 | 64.9 ± 11.9 |
| HI-P364 | 7.9 ± 1.9 | 25.3 ± 9.1 | 27.7 ± 1.2 | 40.1 ± 8.6 | >250 |
| HI-P365 | 86.5 ± 3.4 | 110.7 ± 7.5 | >250 | >250 | >250 |
| HI-P366 | 52.8 ± 14.0 | 137.2 ± 10.3 | 55.5 ± 13.2 | 61.7 ± 12.1 | >250 |
| HI-P369 | >250 | >250 | >250 | >250 | >250 |
| HI-P408 | 116.3 ± 17.8 | 228.5 ± 20.8 | >250 | >250 | >250 |

The compounds were tested for activity against various cancer cells. For example, NALM-6 cells were incubated with HI-P144, HI-P214, HI-P221, HI-P224,HI-P258, HI-P 264, HI-P218, HI-P223, HI-P228, HI-P366, HI-P367, HI-P219, HI-P352, HI-P353, HI-P 364 or HI-P365 for 24 hours in 96-well plates and cell survival was determined by MTT assay. The data points represent the means (±SE) values from 3 independent experiments.

BT-20 breast cancer cells were incubated with HI-P144, HI-214, HI-P221, HI-P224, HI-P258, HI-P264, HI-P218, HI-P223, HI-P228, HI-P366, HI-P367, HI-P219, HI-P352, HI-P353, HI-P364, or HI-P365 for 24 hours in 96-well plates and cell survival was determined by MTT assay. The data points represent the mean (±SE) values from 3 independent experiments.

Figure 3A:
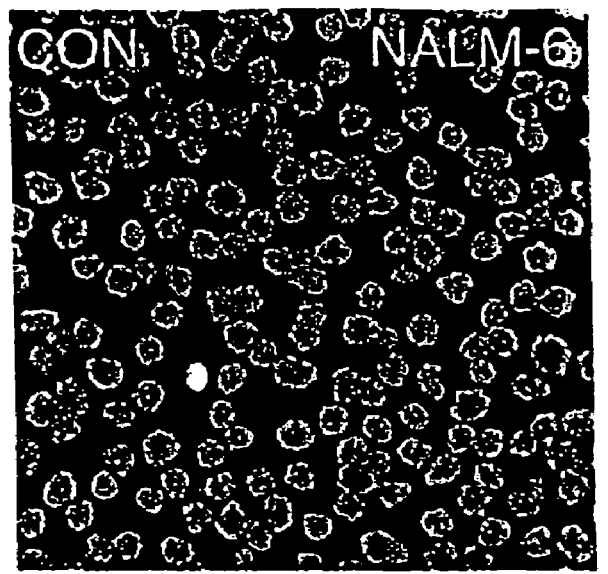
FIGS. 3A–3F are photographs showing induction of apoptosis in cancer cells by F-dmQ.
Figure 3B:
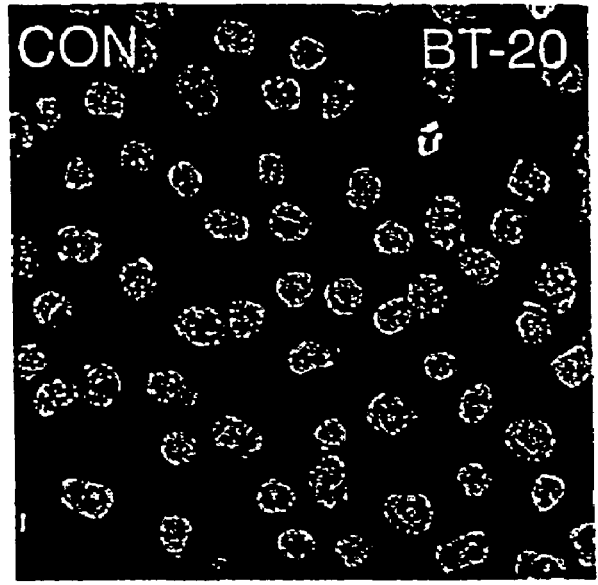
Figure 3C:
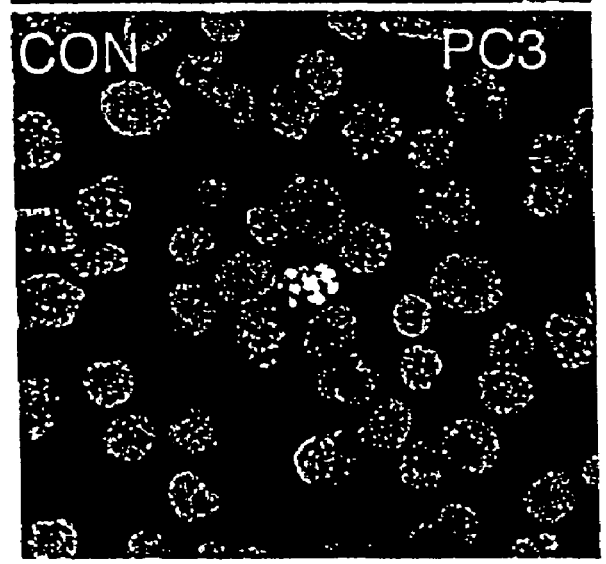
Figure 3D:
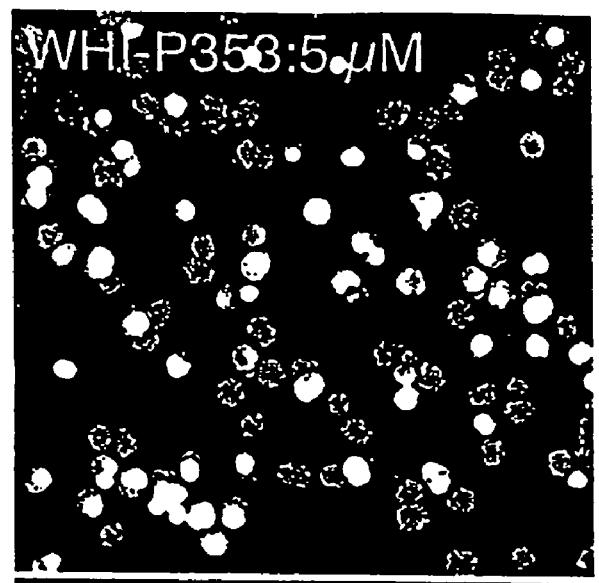
Figure 3E:
Figure 3F:
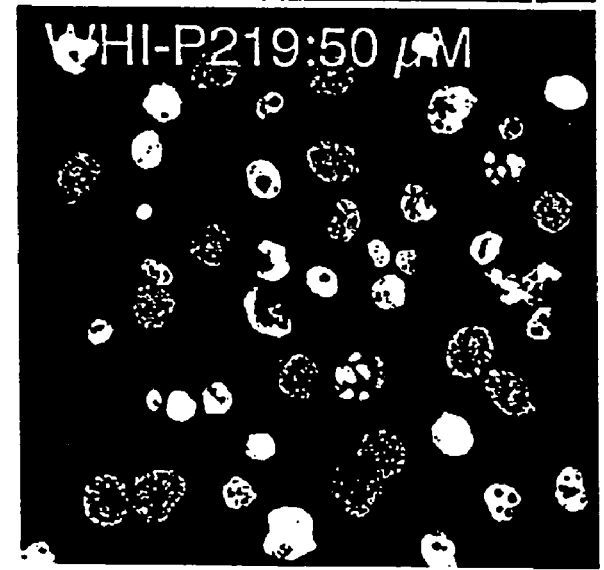
Figure 4:
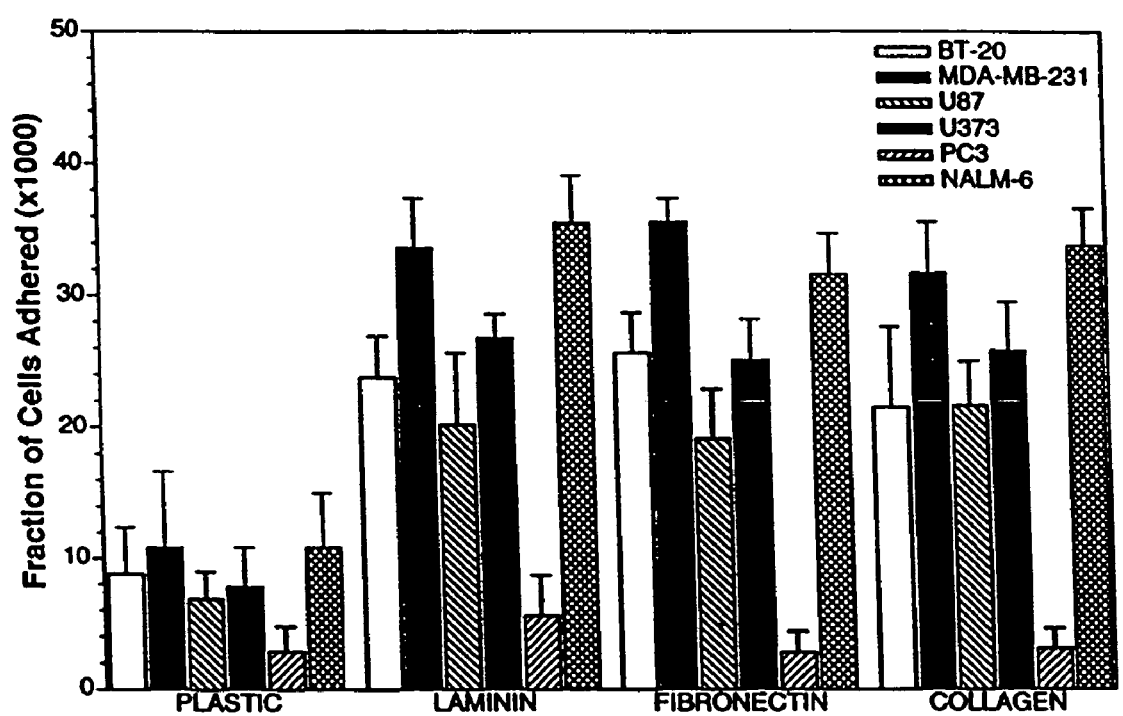
FIG. 4 is a bar graph showing adhesive properties of various cancer cells to extraccellular matrix proteins.
Figure 5D:
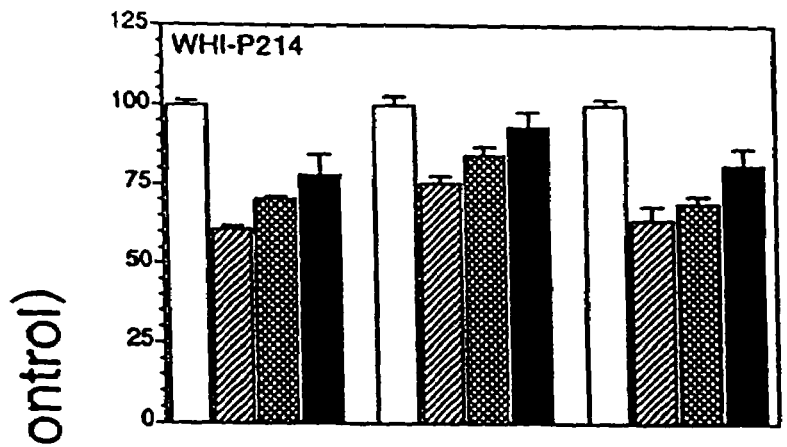
Figure 5E:
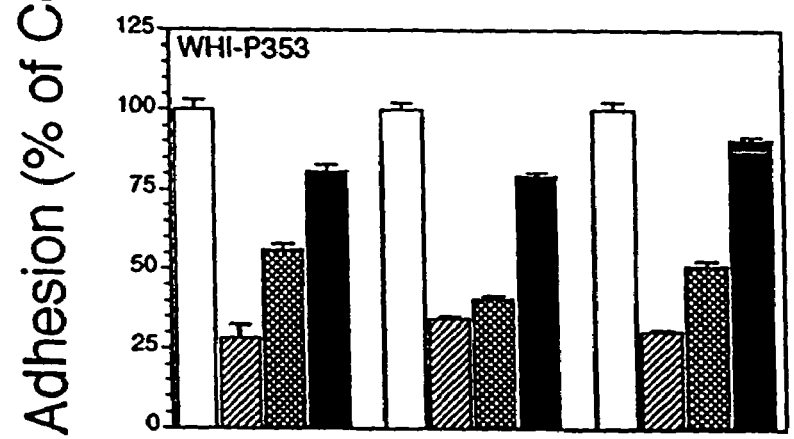
Figure 5F:
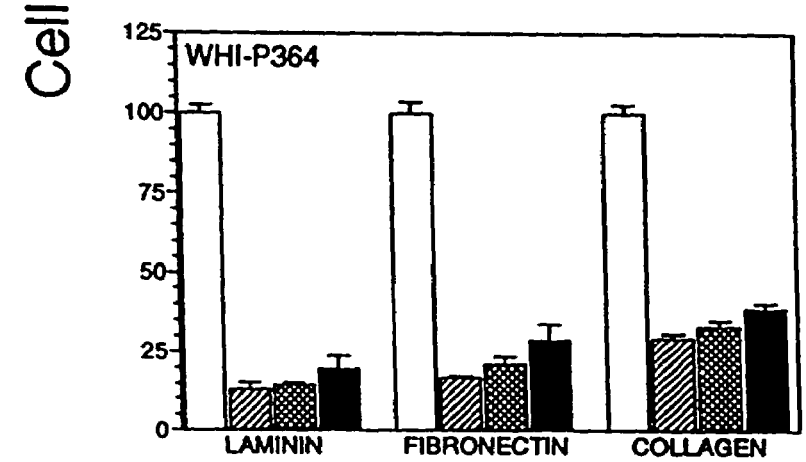
Figure 7A:
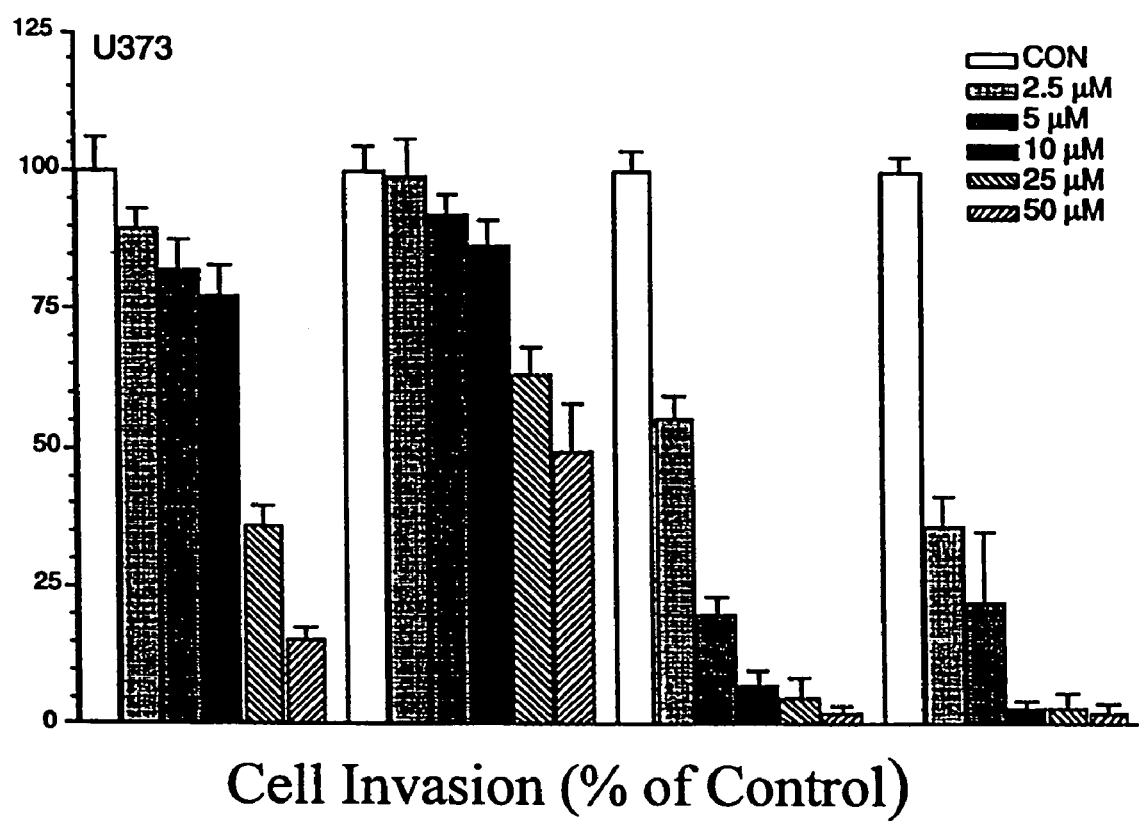
FIGS. 7A and 7B are bar graphs showing the anti-invasive activity of fluoro-substituted quinazoline compounds (F-dmQ) against glioblastoma U373 and breast cancer MDA-MB-231 cells.
Figure 7B:
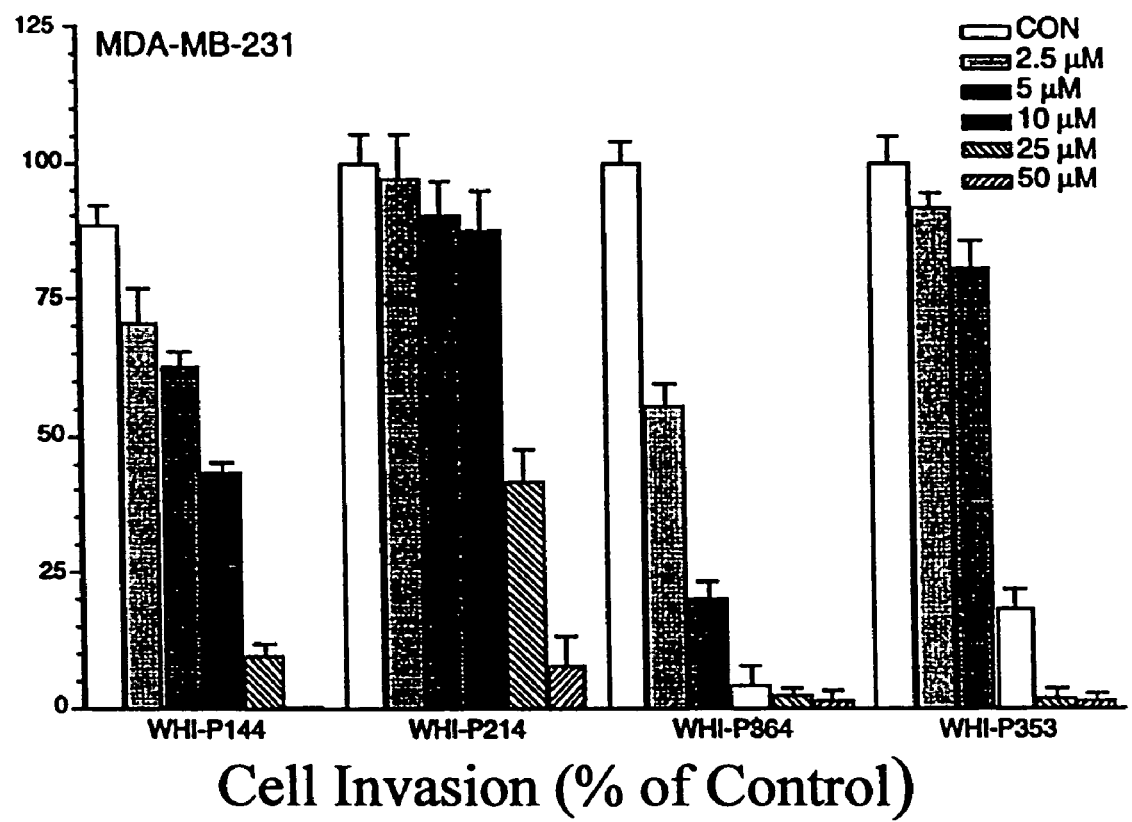
Figure 8A:
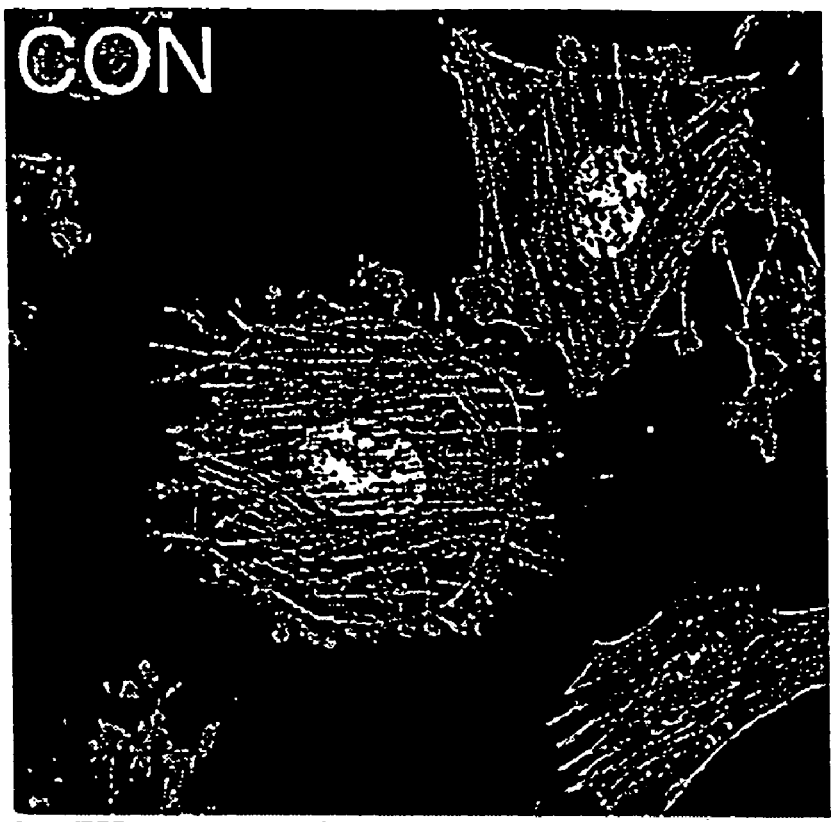
FIGS. 8A–8D are photographs showing depolymerizaton of actin stress fibers and microtubules by HI-P353.
Figure 8B:
Figure 8C:
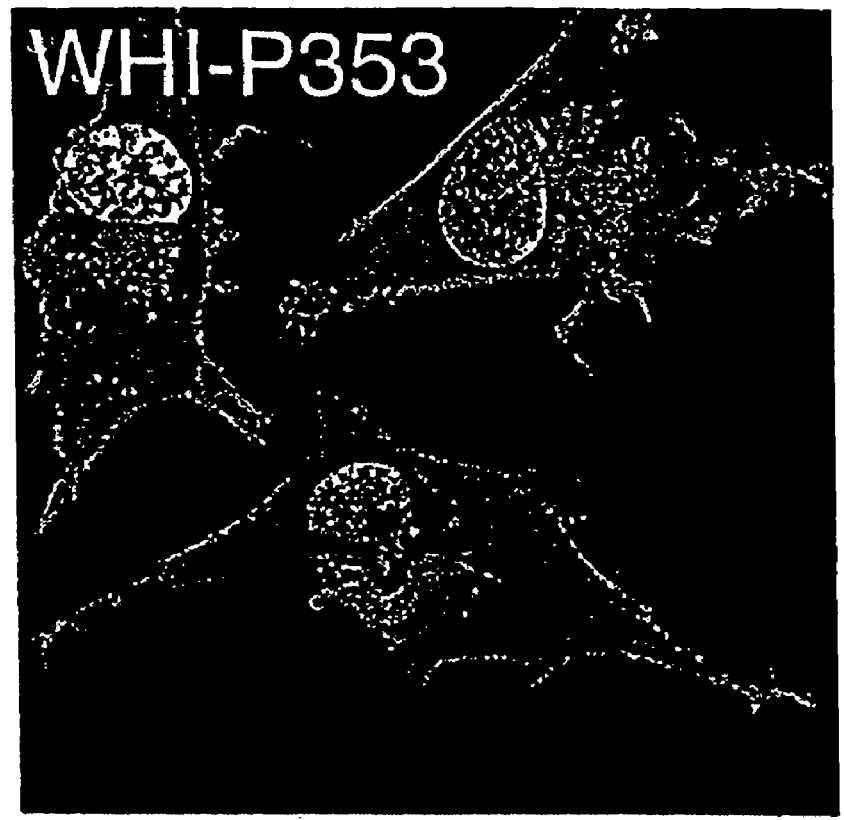
Figure 8D:
Figure 9A:
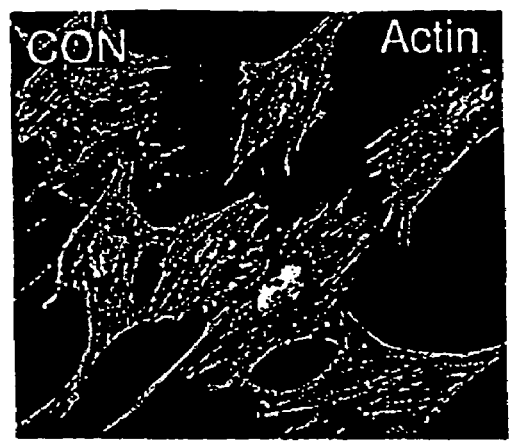
FIGS. 9A–9H are photographs showing inhibition of actin stress fiber formation in glioblastoma cells by HI-P154.
Figure 9B:
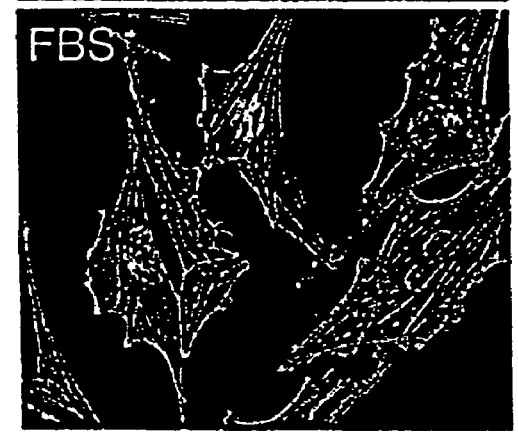
Figure 9C:
Figure 9D:
Figure 9E:
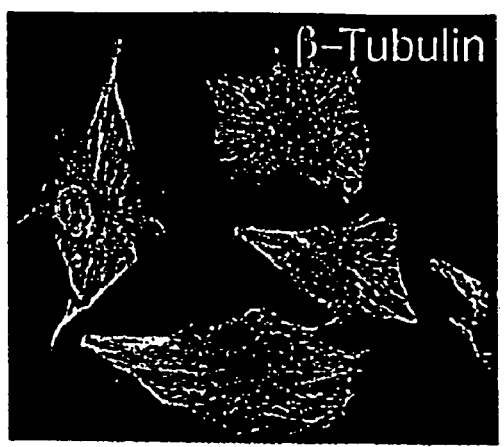
Figure 9F:
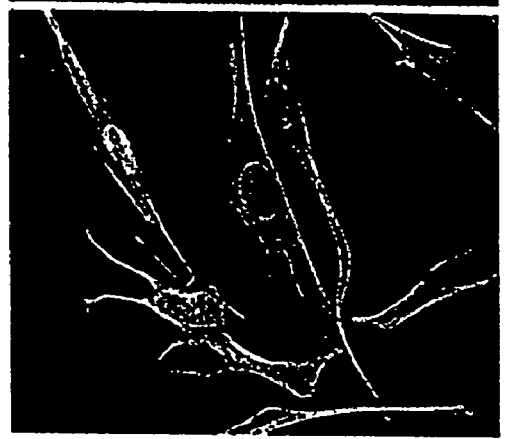
Figure 9G:
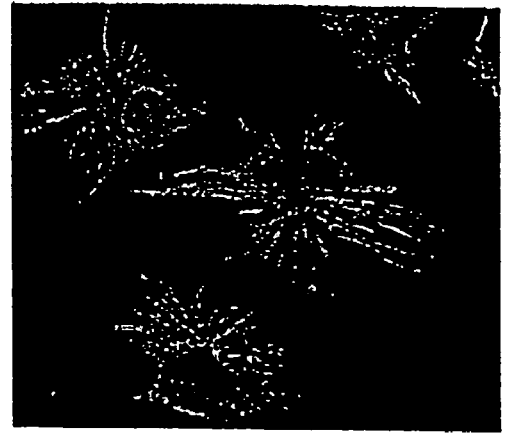
Figure 9H:

Apoptosis was induced by the compounds. The cells were incubated with HI-P353 or HI-P219 for 24 hours, fixed, permeabilized, and visualized for DNA degradation in a TUNEL assay using digoxigenin-UTP-labeling kit. In the color photographs, red fluorescence represents nuclei stained with propidium iodide. Green or yellow (i.e., superimposed red plus green) represents the apoptotic nuclei. Shown are control NALM-6 (FIG. 3A) and BT-20 (FIG. 3B) cells; HI-P353 treated NALM (FIG. 3O) and BT-20 cells (FIG. 3E); and control (FIG. 3C) and HI-P219 treated PC3 cells (FIG. 3F).

Example 8

Pharmacokinetic Studies

In pharmacokinetic studies, mice were injected either intravenously (i.v.) via the tail vein or intraperitoneally (i.p.) with a bolus dose of 300 µg/mouse (~12.5 mg/kg=34 µmols/kg) of HI-P131. Blood samples were obtained from the ocular venous plexus by retroorbital venupuncture prior to and at 3 minutes, 5 minutes, 10 minutes, 15 minutes, 30 minutes, 45 minutes and 1 hour, 2 hours, 4 hours, and 8 hours after administration of HI-P 131. All collected blood samples were heparinized and centrifuged at 7,000 xg for 10 minutes in a microcentrifuge to obtain plasma. The plasma samples were stored at −20° C. until analysis. Aliquots of plasma were used for extraction and HPLC analysis. Pharmacokinetic modeling and pharmacokinetic parameter calculations were carried out using the pharmacokinetics software, WinNonline Program, Version 1.1. (Scientific Consulting Inc., Cary, N.C.). Concentration data were weighted by 1/concentration. An appropriate pharmacokinetic model was chosen on the basis of lowest weighted squared residuals, lowest Schwartz criterion (SC), lowest Akaike's Information Criterion (AIC) value, lowest standard errors of the fitted parameters, and dispersion of the residuals. The elimination half-life was estimated by linear regression analysis of the terminal phase of the plasma concentration profile. The area under the concentration time curve (AUC) was calculated by the trapezoidal rule between first (0 h) and last sampling time plus C/k, where C is the concentration of last sampling and k is the elimination rate constant. Systemic clearance (CL) was determined by dividing the dose by the AUC. The apparent volume of distribution at steady-state was calculated using the following equation, $V_{ss}$=Dose·AUMC/(AUC)$^2$. Bioavailability (F) was estimated using the equation F(%)=AUC$_{ip}$×Dose$_{iv}$/AUC$_{iv}$×Dose$_{ip}$.

HPLC Analysis of Plasma HI-P131 Levels

A highly sensitive quantitative HPLC detection method (Chen et al., 1998, *J. Chromatography B* (*Biomedical sci-* ences), in press) was used to determine the pharmocokinetics of HI-P131. In brief, the HPLC system consisted of a Hewlett Packard (HP) series 1100 equipped with an automated Electronic degasser, a quaternary pump, an autosampler, an automatic thermostatic column compartment, diode array detector and a computer with a Chemstation software program for data analysis. A 250×4 mm Lichrospher 100, RP-18 (5 µm) analytical column and a 4×4 mm Lichrospher 100, RP-18 (5 µm) guard column were obtained from Hewlett Packard Inc. (San Fernando, Calif.). Acetonitrile/water containing 0.1% of trifluoroacetic acid (TFA) and 0.1% triethylamine (TEA) (28:72, v/v) was used as the mobile phase. The wavelength of detection was set at 340 nm. Peak width, response time and slit were set at >0.03 minutes, 0.5 seconds and 8 nm, respectively.

For determination of HI-P131 levels, 10 µL of internal standard HI-P154 (50 µM) was added to a 100 µL plasma sample. For extraction, 7 ml chloroform was then added to the plasma sample, and the mixture was vortexed thoroughly for 3 minutes. Following centrifugation (300×g, 5 minutes), the aqueous layer was frozen using acetone/dry ice and the organic phase was transferred into a clean test tube. The chloroform extracts were dried under a slow steady stream of nitrogen. The residue was reconstituted in 100 µL of methanol: water (9:1) and 50 µL aliquot of this solution was used for HPLC analysis. Under the described chromatographic separation conditions, the retention times for HI-P131 and HI-P154 were 5.1 minutes and 9.5 minutes, respectively. At the retention time, HI-P131 and its internal standard HI-P154 were eluted without any interference peaks from the blank plasma.

HI-P131 was not toxic to mice at intraperitoneal single bolus doses ranging from 0.5 mg/kg to 250 mg/kg. None of the 50 mice treated with HI-P131 experienced side effects or died of toxicity during the 30 day observation period. In particular, we observed no hematologic side effects such as neutropenia, lymphopenia, or anemia at the tested dose levels. No histopathologic lesions were found in the organs of HI-P131 treated mice that were selectively killed at 30 days and there was no bone marrow hypoplasia or lymphoid cell depletion in spleen and lymph nodes. Thus, the maximum tolerated dose (MlD) of HI-P131 was not reached at 250 mg/kg. We next examined the pharmacokinetic features of HI-P131 in mice. A two-compartment pharmacokinetic model was fit to the pharmacokinetics data obtained following the intravenous (i.v.) or intraperitoneal (i.p.) administration of a single non-toxic 12.5 mg/kg bolus dose of HI-P131. The estimated maximum plasma concentrations ($C_{max}$) of HI-P131 were 85.6 µM after i.v. administration.

Example 9

Antitumor Activity of Quinazolines In Vivo

To test the anti-tumor activity of quinazolines in vivo, cancer cells were implanted and grown in mice in the presence of quinazoline.

Inhibition of Breast Cancer Cells

The left hind legs of CB.17 SCID mice were inoculated subcutaneously with $0.75 \times 10^6$ MDA-MB-231 human breast cancer cells in 0.1 ml PBS. Twenty-four hours after inoculation, the mice were treated with HI-P353 (10 mg/kg/day×5 days/week, N=7), or HI-P 364 (10 mg/kg/day×5 days/week, N=8), or vehicle (50% DMSO in PBS, N=7) for four weeks. The mice were monitored daily for health status and tumor growth. Measurements were taken on the tumors 3 times a week using a Vernier caliper. Tumor volumes were calculated using the following formula: (width)²×(length/2). Comparisons of the outcomes of the three groups were done using the log-rank test.

Figure 10A:
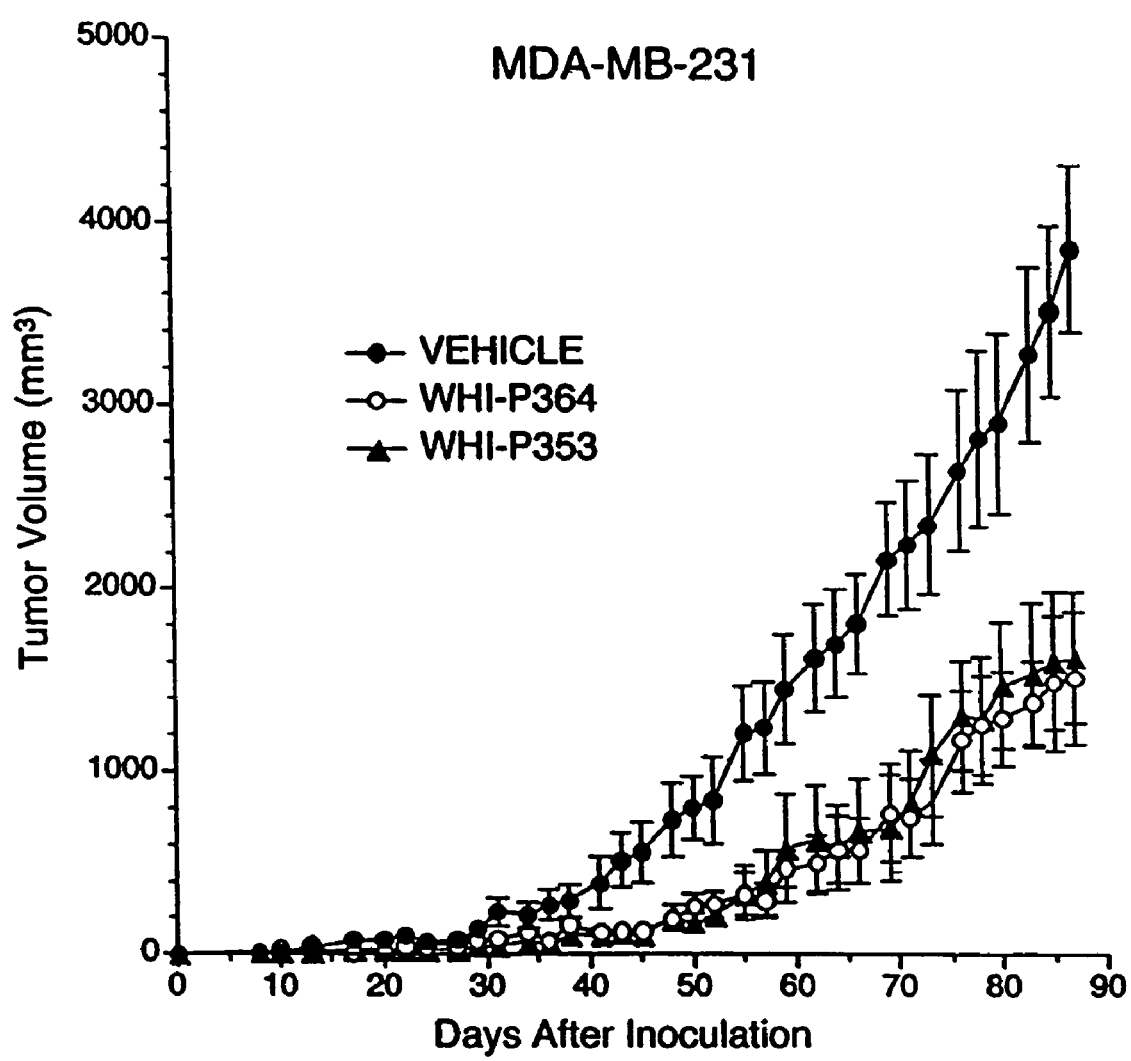
FIGS. 10A–10C are graphs showing the inhibition of cancer cell growth in vivo by the quinazolines of the invention.

The data are shown in FIG. 10A, and demonstrate that treatment of animals with the quinazolines of the invention (HI-P353 and HI-P364) inhibited the growth of breast cancer cell tumors as compared with untreated controls.

Inhibition of Brain Tumor Cells

An analogous experiment was done implanting brain tumor cells into mice. The right hind legs of CB.17 SCID mice were inoculated subcutaneously with $1 \times 10^6$ of U373 human glioblastoma cells in 0.1 ml of PBS. Twenty four hours after inoculation, mice were treated with HI-P353 (10 mg/kg/day×5 days/week, N=7), or HI-P364 (10 mg/kg/day×5 days/week, N=8), or vehicle (50% DMSO in PBS, N=7) for four weeks. Mice were monitored daily for health status and tumor growth. Tumors were measured 3 times a week using a Vernier caliper. Tumor volumes were calculated using the following formula: (width)²×(length/2). Comparisons of outcome between groups were done using the log-rank test.

Figure 10B:
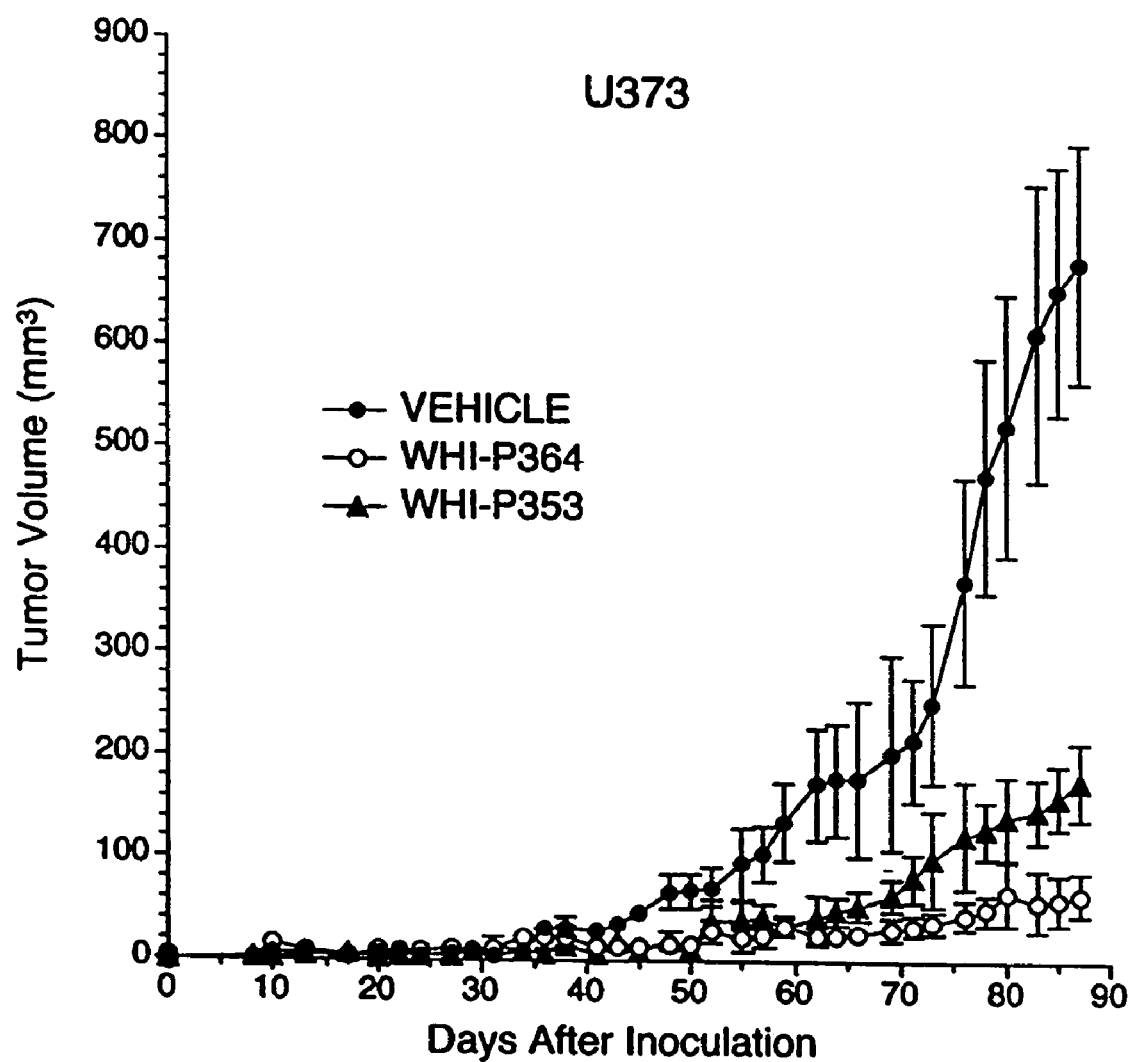

The data are shown in FIG. 10B and demonstrate that treatment of animals with the quinazolines of the invention (HI-P353 and HI-P364) inhibited the growth of brain tumors as compared with untreated controls.

Inhibition of Intracranial Brain Tumors

The anti-tumor activity of the quinazolines of the invention was also studied with intracranial tumors. Nude mice were first anesthetized with Avertin. Under aseptic conditions in a laminar flow hood, a small hole was drilled at 2 mm to the right of the midline and 2 mm posterior to the bregma. An amount of $4 \times 10^5$ U87 glioblastoma cells in 10 µL of PBS were intracranially implanted using a Hamilton syringe into the right cerebral hemisphere of mice and a stereotaxic apparatus according to the method described in Huang, H. J. S. et al., *J. Biol. Chem.* 272:2927–2935, 1997.

Twenty-four hours after inoculation, mice were treated with HI-P353 (20 mg/kg/day× 10 days, n=10), HI-P364 (20 mg/kg/day×10 days, n=10), or vehicle (50% DMSO in PBS, n=10). The mice were monitored twice daily for health status.

Figure 10C:
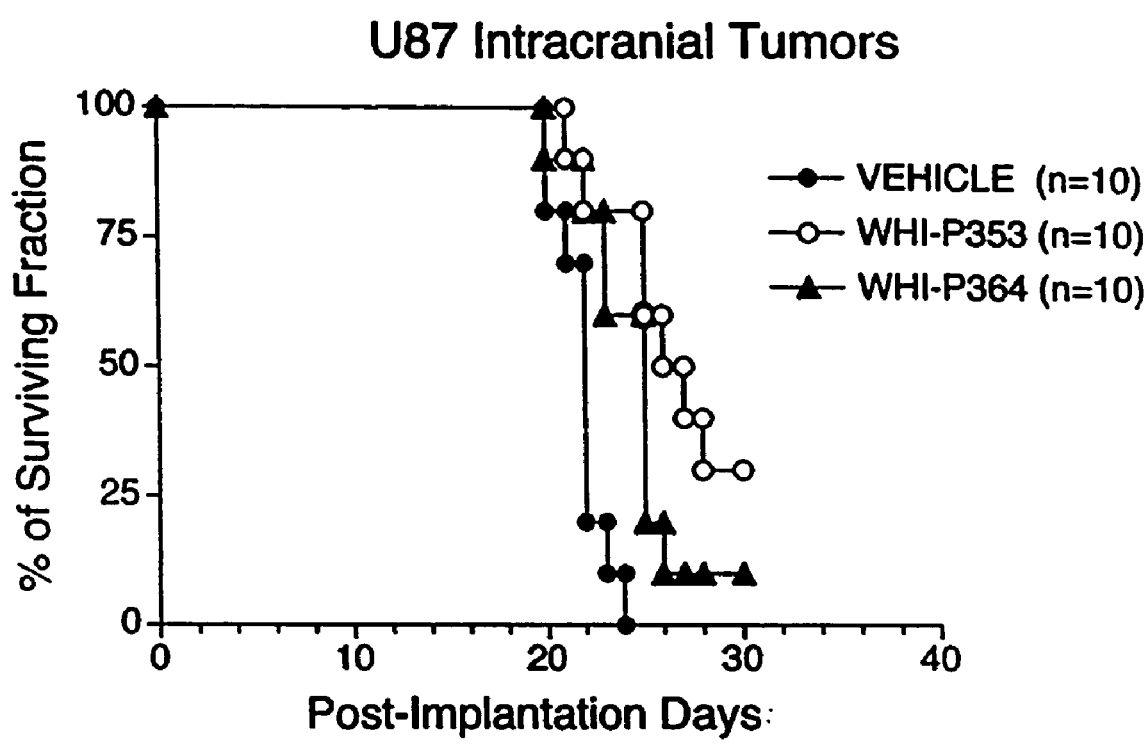

FIG. 10C shows the survival rate of mice inflicted with intracranial tumors. Treatment of mice with quinazolines (HI-P353 and HI-P364) resulted in prolonged survival as compared with mice treated with vehicle alone.

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A compound according to formula V

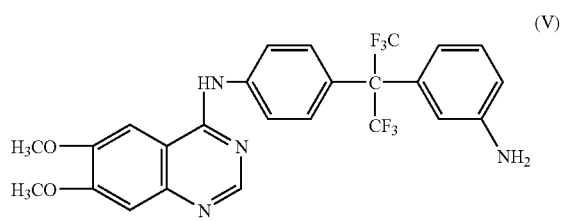

or a pharmaceutically acceptable salt thereof.

2. A composition comprising:
    a therapeutically effective amount of a compound of formula V

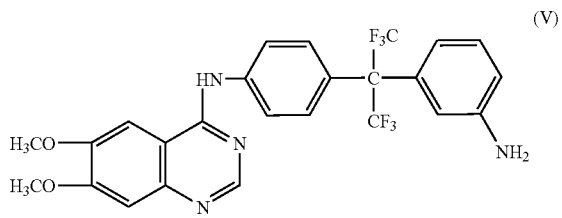

or a pharmaceutically acceptable salt thereof, and at least one pharmaceutically acceptable excipient or diluent.

3. A method of treating leukemia in a subject comprising administering to said subject a compound of formula V

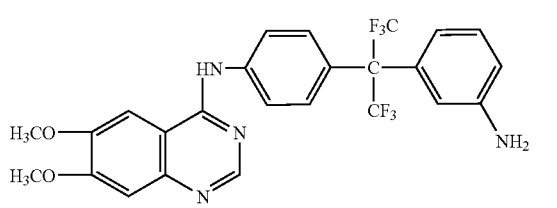

or a pharmaceutically acceptable salt thereof, in an amount effective for inducing apoptosis of leukemia cells.

4. A method of treating breast tumors in a subject comprising administering to said subject a compound of formula V

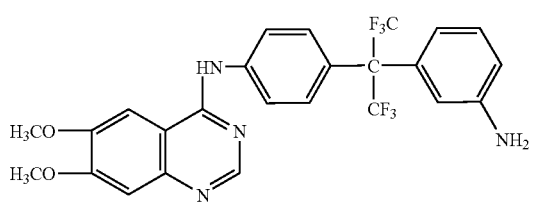

or a pharmaceutically acceptable salt thereof, in an amount effective for inducing apoptosis of breast tumor cells.

5. A method of treating multi-drug resistant leukemia in a subject comprising administering to said subject a compound of formula V

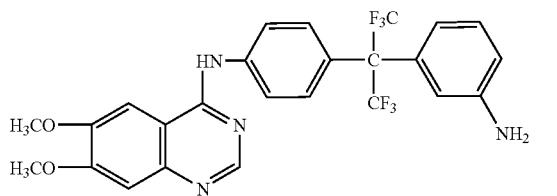

or a pharmaceutically acceptable salt thereof, in an amount effective for inducing apoptosis of multi-drug resistant leukemia cells.

6. A method of treating leukemia in a subject comprising administering to said subject a compound of formula I

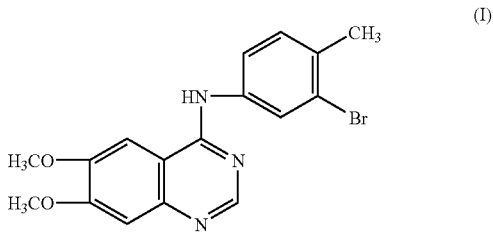

or a pharmaceutically acceptable salt thereof, in an amount effective for inducing apoptosis of leukemia cells.

7. A method of treating breast tumors in a subject comprising administering to said subject a compound of formula I

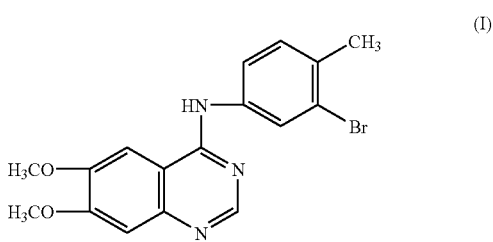

or a pharmaceutically acceptable salt thereof, in an amount effective for inducing apoptosis of breast tumor cells.

8. A method of treating multi-drug resistant leukemia in a subject comprising administering to said subject a compound of formula I

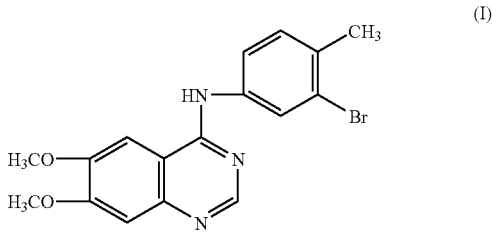

or a pharmaceutically acceptable salt thereof, in an amount effective for inducing apoptosis of multi-drug resistant leukemia cells.

9. A method of treating leukemia in a subject comprising administering to said subject a compound of formula II

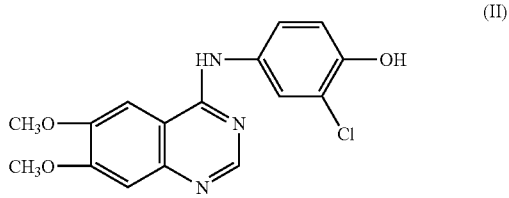

or a pharmaceutically acceptable salt thereof, in an amount effective for inducing apoptosis of leukemia cells.

10. A method of treating breast tumors in a subject comprising administering to said subject a compound of formula II

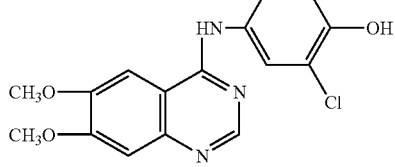
(II)

or a pharmaceutically acceptable salt thereof, in an amount effective for inducing apoptosis of breast tumor cells.

11. A method of treating multi-drug resistant leukemia in a subject comprising administering to said subject a compound of formula II

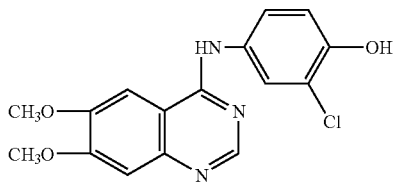
(II)

or a pharmaceutically acceptable salt thereof, in an amount effective for inducing apoptosis of multi-drug resistant leukemia cells.

* * * * *